(12) United States Patent
Kawabata et al.

(10) Patent No.: US 6,723,859 B2
(45) Date of Patent: Apr. 20, 2004

(54) CHROMENE COMPOUND

(75) Inventors: Yuichiro Kawabata, Tokuyama (JP); Yasuko Takeda, Tokuyama (JP); Junji Momoda, Tokuyama (JP); Hironobu Nagoh, Tokuyama (JP); Shinobu Izumi, Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 1 day.

(21) Appl. No.: 09/958,843

(22) PCT Filed: Dec. 22, 2000

(86) PCT No.: PCT/JP00/09419

§ 371 (c)(1),
(2), (4) Date: Oct. 15, 2001

(87) PCT Pub. No.: WO01/60811

PCT Pub. Date: Aug. 23, 2001

(65) Prior Publication Data

US 2003/0096117 A1 May 22, 2003

(30) Foreign Application Priority Data

Feb. 21, 2000 (JP) ........................................ 2000-042682

(51) Int. Cl.⁷ .............................................. C07D 493/20
(52) U.S. Cl. ...................................... 549/332; 549/330
(58) Field of Search ................................. 549/330, 332, 549/345, 428; 544/70, 150; 546/94

(56) References Cited

U.S. PATENT DOCUMENTS 4,440,672 A * 4/1984 Chu ........................... 252/586
6,225,466 B1 * 5/2001 Mann et al. .................. 544/70

FOREIGN PATENT DOCUMENTS

DE          199 027 71 A1 *  2/1999

* cited by examiner

*Primary Examiner*—Taofiq Solola
(74) *Attorney, Agent, or Firm*—Sherman & Shalloway

(57) ABSTRACT

Novel chromene compounds having various substituents to exhibit a high color-developing sensitivity and a high density even when dispersed in a high-molecular matrix, and exhibiting a large fading rate, less color when deteriorated, and excellent light resistance in the photochromic properties; photochromic materials containing the chromene compounds; and use thereof.

12 Claims, 1 Drawing Sheet

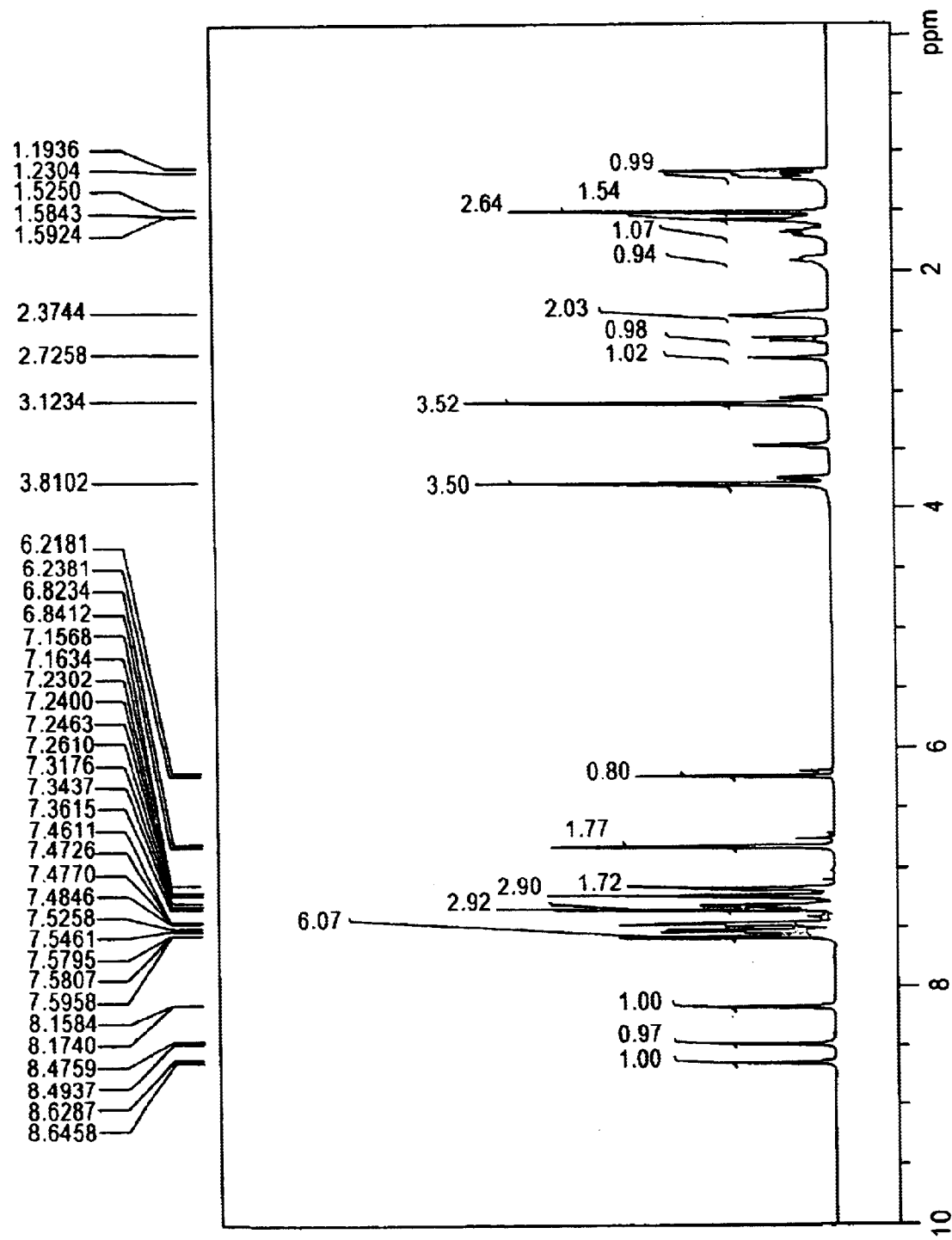

CHROMENE COMPOUND

TECHNICAL FIELD

The present invention relates to novel chromene compounds and the use of the chromene compounds.

BACKGROUND ART

Photochromism is a reversible action of a compound which quickly changes its color when it is irradiated with light containing ultraviolet rays and resumes its initial color when it is no longer irradiated with light but is placed in a dark place. The compound having this property is called photochromic compound. Various compounds have so far been synthesized. Among these photochromic compounds, the chromene compounds exhibit good light resistance and develop colors of a wide variety of tones such as yellow color to blue color, and have been vigorously studied in recent years. Some of the chromene compounds that are developed have already been put into practice as photochromic materials for organic photochromic lenses.

The organic photochromic lens stands for a lens that develops color in an environment where it is irradiated with ultraviolet rays such as outdoors and can be used as sunglasses, and loses its color and returns to its colorless or slightly tinted state in an environment where it is irradiated with weak ultraviolet rays, such as indoors. The organic photochromic lens must satisfy such requirements that it develops a color quickly and densely upon the irradiation with ultraviolet rays and quickly loses color upon the interruption of ultraviolet rays, that it is not colored after faded, and that it exhibits excellent light resistance.

Some chromene compounds found so far exhibit excellent photochromic properties, such as quick color developing/fading rate and a high color density in a solution. When dispersed in a high-molecular matrix such as a plastic material, however, the chromene compound fails to exhibit its intrinsic excellent photochromic properties to a sufficient degree arousing such problems as decreased color density, decreased fading rate and decreased light resistance. These problems appear conspicuously when the chromene compound is dispersed in a rigid high-molecular matrix, deteriorating the fading rate to a conspicuous degree. No method for effectively solving the above problems has been known, and no chromene compound has, either, been known which can be dispersed in a plastic lens that must have a large strength and a hardness to exhibit photochromic properties to a sufficient degree.

For example, the specification of PCT Patent Application WO96/14596 discloses a chromene compound represented by the following formula (A),

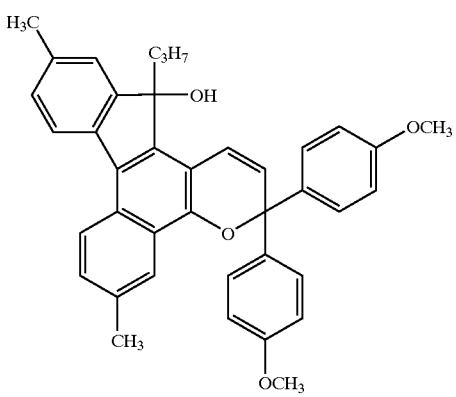

(A)

When dispersed in a high molecular matrix, however, the above chromene compound exhibits a low color-developing sensitivity, a low fading rate, and is colored (also called coloring upon deterioration) even in a state of not irradiated with light when it is used as, for example, a photochromic material for extended periods of time and, further, develops color of a decreased density when irradiated with light.

The specification of PCT Patent Application WO97/48762 discloses a chromene compound represented by the following formula (B),

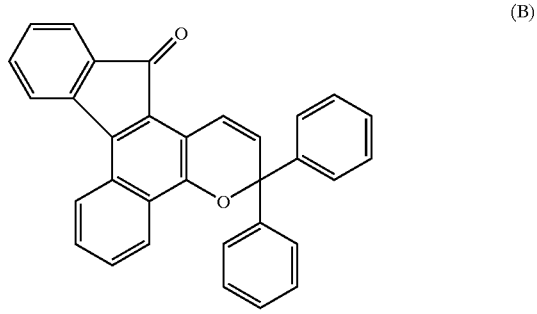

(B)

However, this chromene compound, too, has a problem of slow fading rate when it is dispersed in a high-molecular matrix.

Further, German Application Publication DE19902771A1 discloses a chromene compound represented by the following formula (C),

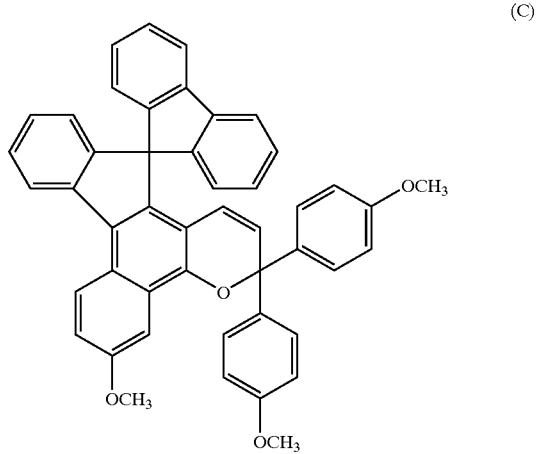

(C)

When dispersed in a high-molecular matrix, however, the above chromene compound exhibits a fading rate which is not of a satisfactory level.

U.S. Pat. No. 6,113,814 discloses a chromene compound represented by the following formula (D),

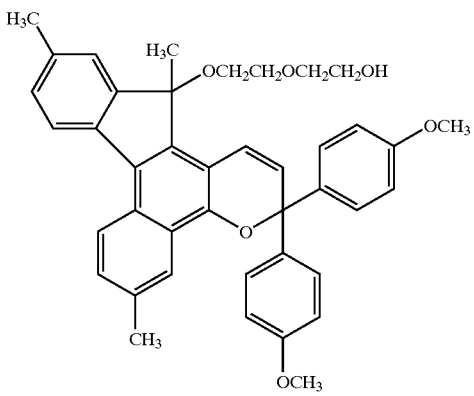

(D)

having a polyalkyleneoxy group with a polymerizable group bonded to one terminal thereof so as to be copolymerizable with a monomer that serves as a high-molecular matrix. This compound, however, has a problem of slow fading rate when it is copolymerized with a monomer that imparts a high hardness or is dispersed in a high-molecular matrix having a high hardness.

DISCLOSURE OF THE INVENTION

It is therefore an object of the present invention to provide a chromene compound which, when dispersed in a high-molecular matrix, exhibits further improved photochromic properties, a high color-developing sensitivity, a high fading rate, less color upon deterioration, and permits photochromic properties to be deteriorated little that is represented by a drop in the color density, i.e., exhibits photochromic properties maintaining excellent light resistance.

The present inventors have conducted keen study in an effort to develop a chromene compound that exhibits excellent photochromic properties in a high molecular matrix. As a result, the inventors have discovered a novel chromene compound which exhibits a high color-developing sensitivity and a high color density even when it is dispersed in a high-molecular matrix, and exhibits a high fading date, less color upon deterioration and exhibits photochromic properties maintaining excellent light resistance, and have completed the present invention.

That is, the present invention is concerned with a chromene compound represented by the following general formula (1),

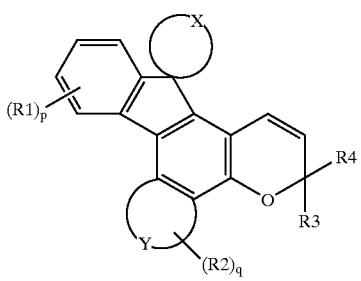

(1)

wherein a group represented by the following formula (2),

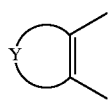

(2)

is an aromatic hydrocarbon group or an unsaturated heterocyclic group;

$R^1$ is a hydroxyl group, an alkyl group, a trifluoromethyl group, an alkoxy group, an alkoxycarbonyl group, a carboxyl group, an alkoxymethyl group, a hydroxymethyl group, an aralkoxy group, an amino group, a substituted amino group, a cyano group, a nitro group, a halogen atom, an aralkyl group, a substituted or unsubstituted aryl group, a substituted or unsubstituted heteroaryl group, a substituted or unsubstituted heterocyclic group having a nitrogen atom as a hetero atom and in which the nitrogen atom and an indene ring are coupled together, or a condensed heterocyclic group in which the heterocyclic group is condensed with an aromatic hydrocarbon ring or an aromatic heterocyclic ring, and p is an integer of 0 to 3;

$R^2$ is a hydroxyl group, an alkyl group, a trifluoromethyl group, an alkoxy group, an alkoxycarbonyl group, a carboxyl group, an alkoxymethyl group, a hydroxymethyl group, an aralkoxy group, an amino group, a substituted amino group, a cyano group, a nitro group, a halogen atom, an aralkyl group, a substituted or unsubstituted aryl group, a substituted or unsubstituted heteroaryl group, a substituted or unsubstituted heterocyclic group having a nitrogen atom as a hetero atom and in which the nitrogen atom and a ring of the group represented by the above formula (2) are bonded together, or a condensed heterocyclic group in which the heterocyclic group is condensed with an aromatic hydrocarbon ring or an aromatic heterocyclic ring, and q is an integer of 0 to 3;

$R^3$ and $R^4$ are, independently from each other, a group represented by the following formula (3),

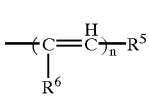

(3)

wherein $R^5$ is a substituted or unsubstituted aryl group, or a substituted or unsubstituted heteroaryl group, $R^6$ is a hydrogen atom, an alkyl group or a halogen atom, and n is an integer of 1 to 3, a group represented by the following formula (4)

(4)

wherein $R^7$ is a substituted or unsubstituted aryl group, or a substituted or unsubstituted heteroaryl group, and m is an integer of 1 to 3, a substituted or unsubstituted aryl group, a substituted or unsubstituted heteroaryl group, or an alkyl group, or $R^3$ and $R^4$ together may constitute an aliphatic hydrocarbon ring or an aromatic hydrocarbon ring; and a cyclic group spiro-bonded to the first position of an indene ring represented by the following formula (5),

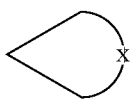
(5)

is an aliphatic hydrocarbon cyclic group which is an unsubstituted monocyclic ring having 7 to 20 carbon atoms in the ring, an aliphatic hydrocarbon cyclic group which is a monocyclic ring having 4 to 20 carbon atoms in the ring and has at least one substituent selected from alkyl group, alkoxy group, amino group, substituted amino group, substituted or unsubstituted aralkyl group and substituted or unsubstituted aryl group, a crosslinked cyclic spiro-cyclic aliphatic hydrocarbon cyclic group which may have at least one substituent selected from the group consisting of alkyl group, alkoxy group, amino group, substituted amino group, substituted or unsubstituted aralkyl group and substituted or unsubstituted aryl group, or a substituted or unsubstituted cyclic group having 4 to 20 carbon atoms in the ring, the cyclic group having at least any one of the following groups in a number of 1 or 2 or more (but not containing two oxy groups),

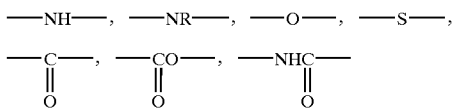

wherein R is an alkyl group, a substituted or unsubstituted aryl group, a substituted or unsubstituted aralkyl group, a carboxyl group or an alkoxycarbonyl group.

The chromene compound according to the present invention has, in the molecules thereof, no polyalkyleneoxy group with a polymerizable group bonded at one terminal thereof. Therefore, when the chromene compound is mixed with, for example, a monomer to be polymerized so as to be dispersed in a high-molecular matrix of a high hardness, the molecular motion is suppressed little, and the isomerization takes place smoothly without causing the fading rate to be greatly decreased.

Among the above-mentioned chromene compounds of the present invention, a high fading rate is exhibited by the chromene compound in which a cyclic group spiro-bonded to a first position of the indene ring represented by the above formula (5) is ① an aliphatic hydrocarbon cyclic group which is an unsubstituted monocyclic ring having 7 to 15 carbon atoms in the ring, ② an aliphatic hydrocarbon cyclic group which is a monocyclic ring having 4 to 15 carbon atoms in the ring and having at least one substituent selected from alkyl group, alkoxy group, amino group, substituted amino group, substituted or unsubstituted aralkyl group and substituted or unsubstituted aryl group, and, particularly, the one having a substituent at the β-position of spiro carbon, and ③ a bicyclic group or a tricyclic group having 4 to 15 carbon atoms in the ring which may have at least one substituent selected from the group consisting of alkyl group, alkoxy group, amino group, substituted amino group, substituted or unsubstituted aralkyl group and substituted or unsubstituted aryl group, or ④ a substituted or unsubstituted cyclic group having 4 to 15 carbon atoms in the ring, the cyclic group having one or two of at least one kind of group selected from the group consisting of —NH— group, —NR— group (where R is an alkyl group, a substituted or unsubstituted aryl group, substituted or unsubstituted aralkyl group, a carboxyl group or an alkoxycarbonyl group), —S— group, —O— group, —C(=O)— group, —C(=O)O— group and —NHC(=O)— group (but not containing two oxy groups).

Another invention is concerned with a photochromic material containing the above chromene compound of the present invention. Among the photochromic materials, those containing an ultraviolet-ray stabilizer exhibit a particularly high light resistance.

The chromene compound of the present invention or the photochromic material of the present invention exhibits excellent photochromic properties even when it is dispersed in a high-molecular matrix and, particularly, in a high-molecular matrix having a high hardness, and can, hence, be favorably used as a photochromic optical material. Therefore, the photochromic optical material containing the chromene compound of the present invention in the high-molecular matrix and, particularly, the one in which the high-molecular matrix has a Rockwell hardness of 80 to 120, is useful as an optical material such as plastic photochromic spectacle lenses that require a mechanical strength.

Such an optical material can be obtained by polymerization-curing, for example, a polymerizable monomer and a photochromic curable composition of the present invention containing a photochromic material of the present invention.

Further, the photochromic material of the present invention exhibits a high color density and a high light resistance and, hence, exhibits excellent photochromic properties even when it is dispersed in a high molecular matrix having a small thickness, such as a film. For example, a layer containing the photochromic material of the present invention is laminated on at least one surface of the lens to obtain an excellent photochromic lens.

BRIEF DESCRIPTION OF DRAWING

The drawing is a proton nuclear magnetic resonance spectrum of a compound of Example 1.

BEST MODE FOR CARRYING OUT THE INVENTION

In the above-mentioned general formula (1), the group represented by the following formula (2),

(2)

is an aromatic hydrocarbon group or an unsaturated heterocyclic group.

Though there is no particular limitation, the above aromatic hydrocarbon group is preferably the one having 6 to 18 carbon atoms. Preferred examples of the aromatic hydrocarbon group include phenylene group, naphthylene group, phenanthrene group, tolylene group, and xylene having one benzene ring or a condensed ring of 2 to 4 benzene rings.

There is no particular limitation on the unsaturated heterocyclic group. Preferably, however, the unsaturated heterocyclic group is a 5-membered ring, a 6-membered ring including an oxygen atom, a sulfur atom or a nitrogen atom, or a heterocyclic group thereof condensed with a benzene ring. Preferred examples of the unsaturated heterocyclic group include nitrogen-containing heterocyclic groups such as pyridylene group, quinolylene group, pyrrolylene group and indolylene group, oxygen-containing heterocyclic groups such as furylene group and benzofurylene group, and sulfur-containing heterocyclic groups such as thienylene group and benzothienylene group.

In the aromatic hydrocarbon group and in the unsaturated heterocyclic group, further, 1 to 3 hydrogen atoms may be substituted by $R^2$. Here, $R^2$ is a hydroxyl group, an alkyl group, a trifluoromethyl group, an alkoxy group, an alkoxycarbonyl group, a carboxyl group, an alkoxymethyl group, a hydroxymethyl group, an aralkoxy group, an amino group, a substituted amino group, a cyano group, a nitro group, a halogen atom, an aralkyl group, a substituted or unsubstituted aryl group, a substituted or unsubstituted heteroaryl group, a substituted or unsubstituted heterocyclic group having a nitrogen atom as a hetero atom and in which the nitrogen atom and a ring of the group represented by the above formula (2) are bonded together, or a condensed heterocyclic group in which the heterocyclic group is condensed with an aromatic hydrocarbon ring or an aromatic heterocyclic ring.

Described below are the groups other than the hydroxyl group, trifluoromethyl group, carboxyl group, hydroxymethyl group, amino group, cyano group and nitro group of which the structures have been known.

Though there is no particular limitation, it is desired that the alkyl group $R^2$ is generally the one having 1 to 4 carbon atoms. Preferred examples of the alkyl group include methyl group, ethyl group, n-propyl group, isopropyl group, n-butyl group, sec-butyl group and t-butyl group.

Though there is no particular limitation, the alkoxy group is generally the one having 1 to 5 carbon atoms. Preferred examples of the alkoxy group include methoxy group, ethoxy group, n-propoxy group, isopropoxy group, n-butoxy group, sec-butoxy group and t-butoxy group.

Though there is no particular limitation, the alkoxycarbonyl group is usually the one having 2 to 6 carbon atoms. Preferred examples of the alkoxycarbonyl group include methoxycarbonyl group, ethoxycarbonyl group, n-propoxycarbonyl group, isopropoxycarbonyl group, n-butoxycarbonyl group, sec-butoxycarbonyl group and t-butoxycarbonyl group.

Though there is no particular limitation, the alkoxymethyl group is usually the one having 2 to 6 carbon atoms. Preferred examples of the alkoxymethyl group include methoxymethyl group, ethoxymethyl group, n-propoxymethyl group, isopropoxymethyl group, n-butoxymethyl group, sec-butoxymethyl group and t-butoxymethyl group.

Though there is no particular limitation, the aralkoxy group is preferably the one having 6 to 10 carbon atoms. Preferred examples of the aralkoxy group include phenoxy group and naphthoxy group.

Though there is no particular limitation, the substituted amino group is preferably the one having alkyl group or aryl group as substituent, such as alkylamino group, dialkylamino group, arylamino group and diarylamino group. Preferred examples of the substituted amino group include methylamino group, ethylamino group, phenylamino group, dimethylamino group, diethylamino group and diphenylamino group.

As the halogen atom, there can be exemplified fluorine atom, chlorine atom, bromine atom or iodine atom.

Though there is no particular limitation, the aralkyl group is preferably the one having 7 to 11 carbon atoms. Preferred examples of the aralkyl group include benzyl group, phenylethyl group, phenylpropyl group and phenylbutyl group.

Though there is no particular limitation, the unsubstituted aryl group is the one having 6 to 10 carbon atoms. Preferred examples of the unsubstituted aryl group include phenyl group and naphthyl group.

The substituted aryl group may be the one in which at least one of the hydrogen atoms in the unsubstituted aryl group is substituted by a substituent. Like the above, the substituent in this case will be a hydroxyl group, an alkyl group, a trifluoromethyl group, an alkoxy group, an aralkoxy group, an alkoxycarbonyl group, a carboxyl group, an alkoxymethyl group, a hydroxymethyl group, an amino group, a substituted amino group, a cyano group, a nitro group, a halogen atom, an aryl group or an aralkyl group, as well as a heteroaryl group, a substituted or unsubstituted heterocyclic group having a nitrogen atom as a hetero atom and in which the nitrogen atom is bonded to the aryl group, a condensed heterocyclic group in which the heterocyclic group is condensed with an aromatic hydrocarbon ring or an aromatic heterocyclic ring {same as the substituted or unsubstituted heterocyclic group that will be described later having a nitrogen atom as a hetero atom and in which the nitrogen is bonded to a ring of the group represented by the above formula (2), except that the ring that is bonded is a ring of the aryl group, or is the same as the condensed heterocyclic group in which the heterocyclic group is condensed with an aromatic hydrocarbon ring or an aromatic heterocyclic ring; this also holds true in the following description irrespective of the ring or the group that is bonded}.

Though there is no particular limitation, the unsubstituted heteroaryl group is the one having 4 to 12 carbon atoms. Concrete examples include thienyl group, furyl group, pyrrolinyl group, pyridyl group, benzothienyl group, benzofuranyl group and benzopyrrolinyl group.

As the substituted heteroaryl group, there can be exemplified the one in which at least hydrogen atom of the unsubstituted heteroaryl group is substituted by a substituent. The substituent in this case may be the same substituent for the above-mentioned substituted aryl group.

There is no particular limitation on the substituted or unsubstituted heterocyclic group having the nitrogen atom as a hetero atom and in which the nitrogen atom is boned to a ring of the group represented by the above formula (2), or on the condensed heterocyclic group in which the heterocyclic group is condensed with an aromatic hydrocarbon ring or with an aromatic heterocyclic ring. It is, however, desired that the heterocyclic group is constituted by 2 to 10 carbon atoms and, particularly, by 2 to 6 carbon atoms. The heretocyclic ring may contain a hetero atom in addition to the nitrogen atom bonded to the ring of the group represented by the above formula (2). Though there is no particular limitation on the hetero atom, it is desired to use an oxygen atom, a sulfur atom or a nitrogen atom. As the substituent of the group, there can be exemplified the substituents same as those for the above-mentioned substituted aryl group.

Described below are concrete examples of the substituted or unsubstituted heterocyclic group having a nitrogen as a hetero atom and in which the nitrogen atom is bonded to a ring of the group represented by the above formula (2), or concrete examples of the condensed heterocyclic group in which the heterocyclic group is condensed with an aromatic hydrocarbon ring or an aromatic heterocyclic ring. That is, the examples are morpholino group, piperidino group, hexamethyleneimino group, thiomorpholino group, pyrrolyl group, tetrahydroquinolyl group, carbazole group, indole group, pyrrolidinyl group, piperadino group, N-methylpiperadino group and indolinyl group.

q is an integer of 0 to 3 and represents the number of the substituents $R^2$. There is no limitation on the position to where $R^2$ is bonded and there is no limitation, either, on the total number of the positions. However, it is desired that the number of the positions is not larger than 2. When q is 2 or 3, the substituents $R^2$ may be different from each other.

In the above-mentioned general formula (1), $R^1$ is a hydroxyl group, an alkyl group, a trifluoromethyl group, an alkoxy group, an aralkoxy group, an alkoxycarbonyl group, a carboxyl group, an alkoxymethyl group, a hydroxymethyl group, an amino group, a substituted amino group, a cyano group, a nitro group, a halogen atom, an aralkyl group, a substituted or unsubstituted aryl group, a substituted or unsubstituted heteroaryl group, a substituted or unsubstituted heterocyclic group having a nitrogen atom as a hetero atom and in which the nitrogen atom is bonded to an indene ring, or a condensed heterocyclic group in which the heterocyclic group is condensed with an aromatic hydrocarbon ring or an aromatic heterocyclic ring. As the groups, there can be exemplified those represented by $R^2$.

p which represents the number of the substituents $R^1$ is an integer of 0 to 3. There is no limitation on the position to where $R^1$ is bonded and there is no limitation, either, on the total number of the positions. However, it is desired that the number of the positions is not larger than 2. When p is 2 or 3, the substituents $R^1$ may be different from each other.

In the above-mentioned general formula (1), $R^3$ and $R^4$ are, independently from each other, a group represented by the following formula (3),

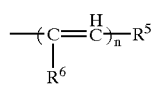
(3)

wherein $R^5$ is a substituted or unsubstituted aryl group, or a substituted or unsubstituted heteroaryl group, $R^6$ is a hydrogen atom, an alkyl group or a halogen atom, and n is an integer of 1 to 3, a group represented by the following formula (4),

(4)

wherein $R^7$ is a substituted or unsubstituted aryl group, or a substituted or unsubstituted heteroaryl group, and m is an integer of 1 to 3, a substituted or unsubstituted aryl group, a substituted or unsubstituted heteroaryl group, or an alkyl group.

Further, not being limited thereto only, $R^3$ and $R^4$ together may constitute an aliphatic hydrocarbon ring or an aromatic hydrocarbon ring.

In the above formula (3), $R^5$ is a substituted or unsubstituted aryl group, or a substituted or unsubstituted heteroaryl group. As the substituted or unsubstituted aryl group, there can be exemplified the groups same as those substituted or unsubstituted aryl groups denoted by $R^1$ and $R^2$.

In the substituted aryl group, there is no particular limitation on the position to where the substituent is bonded and there is no particular limitation, either, on the total number of the positions. When the aryl group is a phenyl group, however, the third position or the fourth position is preferred and, when the aryl group is a naphthyl group, the fourth position or the sixth position is preferred.

Though there is no particular limitation, it is desired that the unsubstituted heteroaryl group is the one having 4 to 12 carbon atoms. Concrete examples include thienyl group, furyl group, pyrrolinyl group, pyridyl group, benzothienyl group, benzofuranyl group and benzopyrrolinyl group. As the substituted heteroaryl group, further, there can be exemplified those in which one or two or more hydrogen atoms of the unsubstituted heteroaryl group are substituted by the groups same as the substituents in the substituted aryl group of $R^1$ or $R^2$. There is no particular limitation on the position to where these substituents are bonded and there is no particular limitation, either, on the total number thereof.

In the above formula (3), $R^6$ is a hydrogen atom, an alkyl group or a halogen atom. Preferred examples of the alkyl group include methyl group, ethyl group and propyl group. Concrete examples of the halogen atom include fluorine atom, chlorine atom, bromine atom and iodine atom.

In the above formula (3), n is an integer of 1 to 3. However, it is desired that n is 1 from the standpoint of obtaining the starting materials.

Concrete examples of the group represented by the above formula (3) include phenyl-ethylenyl group, (4-(N,N-dimethylamino)phenyl)-ethenyl group, (4-N,N-diethylamino)phenyl)-ethenyl group, (4-morpholinophenyl)-ethenyl group, (4-piperidinophenyl)-ethenyl group, (4-eurolidinophenyl)-ethenyl group, (4-methoxyphenyl)-ethenyl group, (4-methylphenyl)-ethenyl group, (2-(N,N-dimethylamino)phenyl)-ethenyl group, (2-methoxyphenyl)-ethenyl group, phenyl-1-methylethenyl group, (4-(N,N-dimethylamino)phenyl)-1-methylethenyl group, (4-methoxyphenyl)-1-methylethenyl group, phenyl-1-fluoroethenyl group, (4-(N,N-dimethylamino)phenyl)-1-fluoroethenyl group, 2-thienyl-ethenyl group, 2-furyl-ethenyl group, 2-(N-methyl) pyrrolinyl-ethenyl group, 2-benzothienyl-ethenyl group, 2-benzofuranyl-ethenyl group and 2-(N-methyl)indolyl-ethenyl group.

In the above formula (4), $R^7$ is a substituted or unsubstituted aryl group or a substituted or unsubstituted heteroaryl group. These groups are the same as those denoted by $R^5$.

In the above formula (4), there is no particular limitation on m which is an integer of 1 to 3. It is, however, desired that m is 1 from the standpoint of easily obtaining the starting materials.

Concrete examples of the group represented by the above formula (4) include phenyl-ethylinyl group, (4-(N,N-dimethylamino)phenyl)-ethenyl group, (4-(N,N-diethylamino)phenyl)-ethenyl group, (4-morpholinophenyl)-ethenyl group, (4-piperidinophenyl)-ethenyl group, (4-eurolidinophenyl)-ethenyl group, (4-methoxyphenyl)-ethenyl group, (4-methylphenyl)-ethenyl group, (2-(N,N-dimethylamino)phenyl)-ethenyl group, (2-methoxyphenyl)-ethenyl group, 2-thienyl-ethenyl group, 2-furyl-ethenyl group, 2-(N-methyl)pyrrolinyl-ethenyl group, 2-benzothienyl-ethyl group, 2-benzofuranyl-ethenyl group and 2-(N-methyl)indolyl-ethenyl group.

Further, the substituted or unsubstituted aryl group or the substituted or unsubstituted heteroaryl group represented by $R^3$ and $R^4$ are the same as the groups represented by $R^6$.

The alkyl groups represented by $R^3$ and $R^4$ are the same as those represented by $R^1$.

There is no particular limitation on the aliphatic hydrocarbon ring formed by $R^3$ and $R^4$ together. However, preferred examples of the ring include adamantilidene ring, bicyclononylidene ring, and norbornylidene ring.

There is no particular limitation on the aromatic hydrocarbon ring formed by $R^3$ and $R^4$ together. However, a fluorene ring can be exemplified as a preferred ring.

Here, it is desired that at least either $R^3$ or $R^4$ is a substituted or unsubstituted aryl group or substituted or unsubstituted heteroaryl group, or a group having those groups.

It is further particularly desired that at least one of $R^3$ and $R^4$ is a group described in any one of (i) to (ix) below; i.e., (i) a substituted aryl group or a substituted heteroaryl group having a substituted amino group as a substituent;

(ii) a substituted aryl group or a substituted heteroaryl group having, as a substituent, a substituted or unsubstituted heterocyclic group with a nitrogen atom as a hetero atom and in which the nitrogen atom is bonded to the aryl group or the heteroaryl group;

(iii) a substituted aryl group or a substituted heteroaryl group having, as a substituent, a condensed heterocyclic group in which the substituted or unsubstituted heterocyclic group of (ii) above is condensed with an aromatic hydrocarbon ring or an aromatic heterocyclic ring;

(iv) a group represented by the formula (3) in which $R^5$ is a substituted aryl group or a substituted heteroaryl group having a substituted amino group as a substituent;

(v) a group represented by the formula (3) in which $R^5$ is a substituted aryl group or a substituted heteroaryl group having, as a substituent, a substituted or unsubstituted heterocyclic group with a nitrogen atom as a hetero atom and in which the nitrogen atom is bonded to the aryl group or to the heteroaryl group;

(vi) a group represented by the formula (3) in which $R^5$ is a substituted aryl group or a substituted heteroaryl group having, as a substituent, a condensed heterocyclic group in which the substituted or unsubstituted heterocyclic group in (v) above is condensed with an aromatic hydrocarbon ring or an aromatic heterocyclic ring;

(vii) a group represented by the formula (4) in which $R^7$ is a substituted aryl group or a substituted heteroaryl group having a substituted amino group as a substituent;

(viii) a group represented by the formula (4) in which $R^7$ is a substituted aryl group or a substituted heteroaryl group having, as a substituent, a substituted or unsubstituted heterocyclic group that has a nitrogen atom as a hetero atom and in which the nitrogen atom is bonded to the aryl group or to the heteroaryl group; or (ix) a group represented by the formula (4) in which $R^7$ is a substituted aryl group or a substituted heteroaryl group having, as a substituent, a condensed heterocyclic group in which the substituted or unsubstituted heterocyclic group in (viii) above is condensed with an aromatic hydrocarbon ring or an aromatic heterocyclic ring.

In the substituted aryl groups in (i) to (iii) above, there is no particular limitation on the position at where the substituent is substituted and there is no limitation, either, on the total number of the positions. When the aryl group is a phenyl group, however, it is desired that the position of substitution is the third position or the fourth position and the number of the place is one. Preferred examples of the substituted aryl group include 4-(N,N-dimethylamino) phenyl group, 4-(N,N-diethylamino)phenyl group, 4-(N,N-di-n-propylamino)phenyl group, 4-(N,N-di-isopropylamino)phenyl group, 4-(N,N-di-n-butylamino) phenyl group, 4-(N,N-di-t-butylamino)phenyl group, 4-(N,N-diphenylamino)phenyl group, 4-morpholinophenyl group, 4-piperidinophenyl group, 3-(N,N-dimethylamino) phenyl group, 4-thiomorpholinophenyl group, and 4-piperidinophenyl group.

In the substituted heteroaryl groups in (i) to (iii) above, further, there is no particular limitation on the position to where the substituent is substituted and there is no limitation, either, on the total number of the positions. It is, however, desired that the number is 1. Preferred examples of the substituted heteroaryl group include 4-(N,N-dimethylamino)thienyl group, 4-(N,N-diethylamino)furyl group, 4-(N,N-diphenylamino)thienyl group, 4-morpholinopyrrolinyl group, 6-piperidinobenzothienyl group and 6-(N,N-dimethylamino)benzofuranyl group.

In the group represented by the formula (3) mentioned in (iv) to (vi) above, further, $R^5$ in the formula (3) is the same as the substituted aryl group or substituted heteroaryl group in (i) to (iii) above. Preferred examples of the group represented by the formula (3) include (4-(N,N-dimethylamino) phenyl)-ethenyl group, (4-(N,N-diethylamino)phenyl)-ethenyl group, (4-morpholinophenyl)-ethenyl group, (4-piperidinophenyl)-ethenyl group, (4-eurolidinophenyl)-ethenyl group, (2-(N,N-dimethylamino)phenyl)-ethenyl group, (4-(N,N-dimethylamino)phenyl)-1-methylethenyl group and (4-(N,N-dimethylamino)phenyl)-1-fluoroethenyl group.

In the group represented by the formula (4) in (vii) to (ix) above, further, $R^7$ in the formula (4) is the same as the substituted aryl group or the substituted heteroaryl group in (i) to (iii) above. Preferred examples of the group represented by the formula (4) include (4-(N,N-dimethylamino) phenyl)-ethenyl group, (4-(N,N-diethylamino)phenyl)-ethenyl group, (4-morpholinophenyl)-ethenyl group, (4-piperidinophenyl)-ethenyl group, (4-eurolidinophenyl)-ethenyl group, (2-(N,N-dimethylamino)phenyl)-ethenyl group, 2-(N-methyl)indolyl-ethenyl group, and (4-(N-methylpiperadino)phenyl)-ethenyl group.

In the above-mentioned general formula (1), the cyclic group represented by the following formula (5),

(5)

has at least one carbon atom (spiro carbon) as a spiro atom, the spiro carbon being a carbon atom at the first position of the indene ring of the above-mentioned formula (1) to form a spiro bond at this position.

In the above-mentioned general formula (1), the cyclic group represented by the following formula (5) is (a) an aliphatic hydrocarbon cyclic group which is an unsubstituted monocyclic ring having 7 to 20 carbon atoms in the ring, (b) an aliphatic hydrocarbon cyclic group which is a monocyclic ring having 4 to 20 carbon atoms in the ring and having at least one substituent selected from alkyl group, alkoxy group, amino group, substituted amino group, substituted or unsubstituted aralkyl group and substituted or unsubstituted aryl group, (c) a crosslinked cyclic or spiro-cyclic aliphatic hydrocarbon cyclic group which may have at least one substituent selected from the group consisting of alkyl group, alkoxy group, amino group, substituted amino group, substituted or unsubstituted aralkyl group and substituted or unsubstituted aryl group, or (d) a substituted or unsubstituted cyclic group having 4 to 20 carbon atoms in the ring, the cyclic group having any one of the following groups in a number of 1 or 2 or more (but not containing two oxy groups),

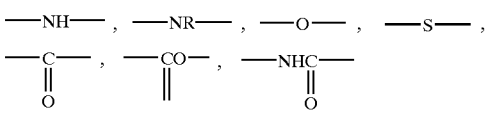

wherein R is an alkyl group, a substituted or unsubstituted aryl group, a substituted or unsubstituted aralkyl group, a carboxyl group or an alkoxycarbonyl group.

There is no particular limitation on the aliphatic hydrocarbon ring in the aliphatic hydrocarbon cyclic group that may have a substituent in (a) to (c) above. However, concrete examples of the aliphatic hydrocarbon ring include, as monocyclic groups, rings having 4 to 15 carbon atoms, such as cyclobutane ring, cyclopentane ring, cyclohexane ring, cycloheptane ring, cyclooctane ring, cyclononane ring, cyclodecane ring, cycloundecane ring, cyclododecane ring, cyclotridecane group, cyclopentadodecane group and 2,4,6-cyclopentatriene; include, as bicyclic rings, rings having 7 to 15 carbon atoms, such as bicyclo[2.2.1]heptane ring, bicyclo[2.2.2]octane ring, bicyclo[3.2.0]heptane ring, octahydro-pentalene ring, bicyclo[3.1.1]heptane ring, bicyclo[3.2.1]octane ring, bicyclo[3.3.1]nonane ring, bicyclo[3.3.2]decane ring, bicyclo[3.3.3]undecane ring, bicyclo[4.2.2]decane ring, bicyclo[4.3.2]undecane ring, bicyclo[4.3.3]dodecane ring, bicyclo[4.1.0]heptane ring, bicyclo[4.1.1]octane ring, bicyclo[4.2.1]nonane ring, bicyclo[4.2.0]octane ring, octahydroindene ring, bicyclo[4.3.1]dodecane ring, decahydro-naphthalene ring and dodecahydro-benzocyclononane ring; and include, as tricyclic rings, rings having 7 to 15 carbon atoms, such as tricycloheptane ring, adamantane ring, dodecahydro-phenalene ring, dodecahydro-cyclopentapantalene ring, dodecahydro-fluorene ring, tetradecahydro-anthracene ring, tricyclododecane ring and tricyclopentadecane ring. Here, the number of carbon atoms must be 7 to 20 in the ring of the aliphatic hydrocarbon cyclic group when it has no substituent. The fading rate becomes small when the number of carbon atoms is 4 to 6. The Spiro carbon that is spiro-bonded to the indene ring may exist at any position on the aliphatic hydrocarbon ring. Further, the groups represented by $R^1$ can be exemplified as alkyl group, alkoxy group, amino group, substituted amino group, substituted or unsubstituted aralkyl group, and substituted or unsubstituted aryl group that may be substituted for the aliphatic hydrocarbon ring. As the substituted or unsubstituted aryl group, there can be particularly preferably exemplified an aryl group having 6 to 10 carbon atoms, such as phenyl group or naphthyl group. There is no particular limitation on the position of substitution or on the total number of the substitutions. Among these cyclic groups, it is particularly desired, from the standpoint of improving the fading rate, to use ① an aliphatic hydrocarbon cyclic group which is an unsubsituted monocyclic ring having 7 to 15 carbon atoms in the ring, ② an aliphatic hydrocarbon cyclic group which is a monocyclic ring having 4 to 15 carbon atoms in the ring and having at least one substituent selected from alkyl group, alkoxy group, amino group, substituted amino group, substituted or unsubstituted aralkyl group and substituted or unsubstituted aryl group and, particularly, the one having a substituent at the β-position of the Spiro carbon, and ③ a bicyclic group or a tricyclic group having 4 to 15 carbon atoms in the ring and may have at least one substituent selected from the group consisting of alkyl group, alkoxy group, amino group, substituted amino group, substituted or unsubstituted aralkyl group and substituted or unsubstituted aryl group. Further, among the monocyclic rings having 7 to 15 carbon atoms of the rings of ① above, those having 7 to 10 carbon atoms are particularly preferably used since they work to improve the fading rate.

The substituted or unsubstituted cyclic group having 4 to 15 carbon atoms in the ring of (d) above is the one in which one or two or more and, preferably, one or two methylene groups constituting:

a cycloalkane nonocyclic ring having 4 to 15 carbon atoms (without including carbon atoms of the substituent), such as cyclobutane, cyclopentane, cyclohexane, cycloheptane, cyclooctane ring, cyclononane ring, cyclodecane ring, cycloundecane ring, cyclododecane ring, cyclotridecane group or cyclopentadodecane group;

a bicyclic ring having 4 to 15 carbon atoms (without including carbon atoms of the substituent), such as bycyclo[2.2.1]heptane ring, bicyclo[2.2.2]octane ring, bicyclo[3.2.0]heptane ring, octahydro-pentalene ring, bicyclo[3.1.1]heptane ring, bicyclo[3.2.1]octane ring, bicyclo[3.3.1]nonane ring, bicyclo[3.3.2]decane ring, bicyclo[3.3.3]undecane ring, bicyclo[4.2.2]decane ring, bicyclo[4.3.2]undecane ring, bicyclo[4.3.3]dodecane ring, bicyclo[4.1.0]heptane ring, bicyclo[4.1.1]octane ring, bicyclo[4.2.1]nonane ring, bicyclo[4.2.0]octane ring, octahydroindene ring, bicyclo[4.3.1]dodecane ring, decahydro-naphthalene ring or dodecahydro-benzocyclononane ring; or a tricyclic ring, such as tricycloheptane ring, adamantane ring, dodecahydro-phenalene ring, dodecahydro-cyclopentapentalene ring, dodecahydro-fluorene ring, tetradecahydro-anthracene ring, tricyclododecane ring or tricyclopentadecane ring;

are substituted by at least one group selected from the group consisting of imino group (—NH—), imino group (—NR—) in which the substituent R is an alkyl group, a substituted or unsubstituted aryl group, a substituted or unsubstituted aralkyl group, a carboxyl group or an alkoxycarbonyl group, oxy group (—O—), thio group (—S—), carbonyl group {—C(=O)—}, carbonyloxy group {—C(=O)—O—} and amido group {—NH—C(=O)—}. Here, however, the oxy groups are not contained in a number of two.

Among the cyclic groups of (d) above, there is preferably used a monocyclic group having 4 to 7 carbon atoms in the ring, a bicyclic group having 7 to 10 carbon atoms in the ring, and a tricyclic group having 10 to 13 carbon atoms in the ring from the standpoint of improving the fading rate and easy synthesis.

Concrete examples of the rings include oxygen-containing rings such as tetrahydrofuran ring and pyran ring; nitrogen-containing rings such as pyrrolidine ring, piperidine ring, morpholine ring, thiomorpholine ring, piperazine ring, and hexamethyleneimine ring; carbonyl-containing rings such as cyclopentanone ring and cyclohexanone ring; ester-containing rings or oxygen-containing/carbonyl-containing mixed rings such as butylolactone ring, tetrahydrofuranone ring and tetrahydropyranone ring; monocyclic rings such as amido-containing rings or nitrogen-containing/carbonyl-containing mixed spiro rings, like pyrrolidinone ring, piperidinone ring and oxohexamethyleneimine ring; bicyclic rings such as aza-bicyclo[2.2.2]octane ring, decahydro-cyclopentaazepin ring, 8-aza-bicyclo[3.2.1]octane ring, and octahydro-quinolizine; and tricyclic rings such as decahydro-pyrridinoquinoline ring and aza-tricycloundacane ring.

The hydrogen atom in the monocyclic ring may be substituted by a substituent. The substituent in this case may be alkyl group, alkoxy group, amino group, substituted amino group, substituted or unsubstituted aralkyl group, or substituted or unsubstituted aryl group. These groups are the same as those denoted by $R^1$.

From the standpoint of effects according to the present invention, it is desired that the chromene compound has a cyclic group represented by the above-mentioned formula (5) as described in (a) to (d), and is the one represented by the following formula (6),

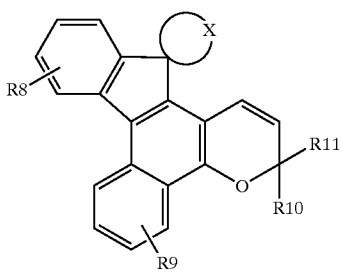

(6)

wherein $R^8$ and $R^9$ are, independently from each other, trifluoromethyl groups, alkyl groups, alkoxy groups, alkoxycarbonyl groups, carboxyl groups, alkoxymethyl groups, hydroxymethyl groups, aralkoxy groups, substituted amino groups, cyano groups, substituted or unsubstituted aryl groups, halogen atoms, aralkyl groups, substituted or unsubstituted heterocyclic groups having a nitrogen atom as a hetero atom and in which the nitrogen atom is bonded to an indene ring or to a naphthalene ring, or condensed heterocyclic groups in which the heterocyclic groups are condensed with an aromatic hydrocarbon ring or an aromatic heterocyclic ring, $R^{10}$ and $R^{11}$ are, independently from each other, substituted or unsubstituted aryl groups, or substituted or unsubstituted heteroaryl groups, and the cyclic group represented by the above-mentioned formula (5) is ① an aliphatic hydrocarbon cyclic group which is an unsubstituted monocyclic ring having 7 to 15 carbon atoms in the ring, ② an aliphatic hydrocarbon cyclic group which is a monocyclic ring having 4 to 15 carbon atoms in the ring and having at least one substituent selected from alkyl group, alkoxy group, amino group, substituted amino group, substituted or unsubstituted aralkyl group and substituted or unsubstituted aryl group and, particularly, the one having a substituent at the β-position of the spiro carbon, ③ a bicyclic group or a tricyclic group having 4 to 14 carbon atoms in the ring and which may have at least one substituent selected from the group consisting of alkyl group, alkoxy group, amino group, substituted amino group, substituted or unsubstituted aralkyl group and substituted or unsubstituted aryl group, or ④ a substituted or unsubstituted cyclic group having 4 to 15 carbon atoms in the ring, the cyclic group having one or two of at least one kind of group (but not containing two oxy groups) selected from the group consisting of —NH— group, —NR— group (wherein R is an alkyl group, a substituted or unsubstituted aryl group, a substituted or unsubstituted aralkyl group, a carboxyl group or an alkoxycarbonyl group), —S— group, —O— group, —C(=O)— group, —C(=O)O— group, and —NHC(=O)— group, and, particularly, $R^{10}$ is an aryl group or a heteroaryl group having an amino group as a substituent; an aryl group or a heteroaryl group having, as a substituent, a substituted or unsubstituted heterocyclic group having a nitrogen atom as a hetero atom and in which the nitrogen atom is bonded to an aryl group or to a heteroaryl group; or a substituted aryl group or a substituted heteroaryl group having, as a substituent, a condensed heterocyclic group in which a substituted or unsubstituted heterocyclic group is condensed with an aromatic hydrocarbon ring or an aromatic heterocyclic ring, the substituted or unsubstituted heterocyclic group having a nitrogen atom as a hetero atom and in which the nitrogen atom is bonded to the aryl group or to the heteroaryl group.

Concrete examples of the chromene compound are as described below.

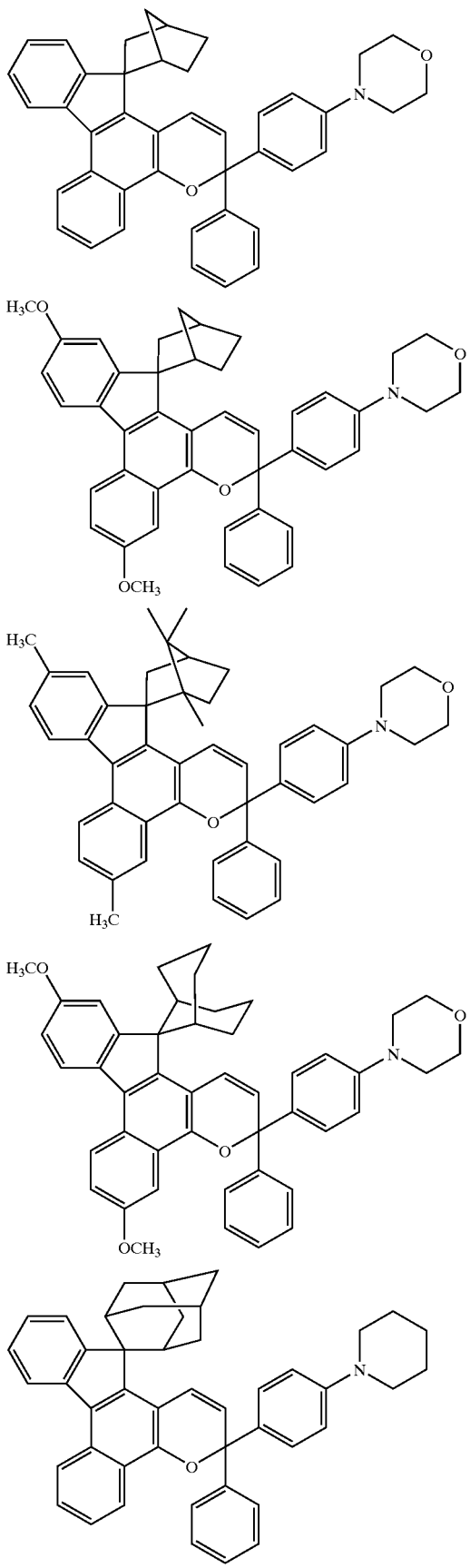

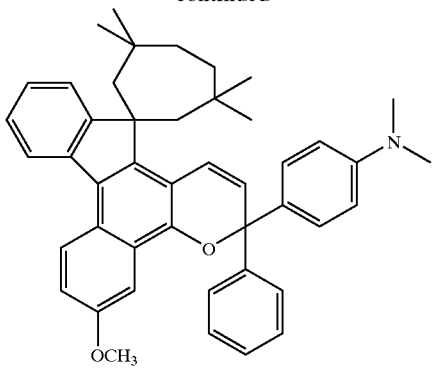

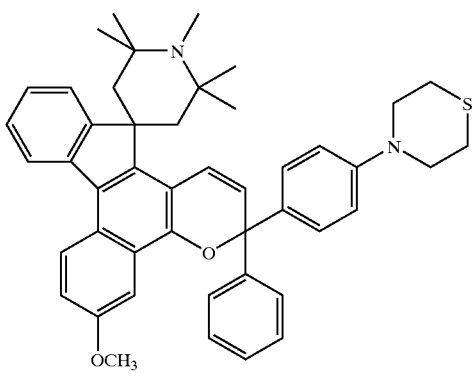

The chromene compound represented by the above general formula (1) of the present invention usually exists as a solid or a viscous liquid which is colorless or is pale yellow at normal temperature and under normal pressure, and can be confirmed by the following means (a) to (c).

(a) A proton nuclear magnetic resonance spectrum ($^1$H-NMR) indicates peaks based on aromatic protons and protons of an alkene near δ 5.0 to 9.0 ppm and peaks based on the protons of an alkyl group and of an alkylene group near δ 1.0 to 4.0 ppm. Further, a comparison of the spectral intensities teaches the number of protons of the bonded groups.

(b) A composition of a corresponding product can be determined by the elemental analysis.

(c) A $^{13}$C-nuclear magnetic resonance spectrum ($^{13}$C-NMR) indicates peaks based on the carbon atoms of an aromatic hydrocarbon group near δ 110 to 160 ppm, peaks based on the carbon atoms of an alkene and an alkyne near δ 80 to 140 ppm, and peaks based on the carbon atoms of an alkyl group and an alkylene group near δ 20 to 80 ppm.

There is no particular limitation on the method of preparing chromene compounds represented by the general formula (1) and any synthesizing method can be employed. Described below are representative methods that are usually favorably employed.

A method of reacting a hydroxy-fluorenone derivative represented by the following general formula (7),

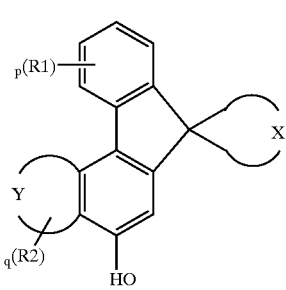 (7)

wherein $R^1$, $R^2$, a cyclic group containing x (corresponds to the cyclic group represented by the above-mentioned general formula (5)), p, q and a group represented by the following formula,

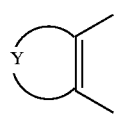 (2)

are as defined in the above-mentioned general formula (1), with a propargyl alcohol derivative represented by the following general formula,

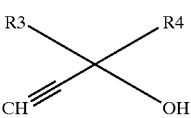 (8)

wherein $R^3$ and $R^4$ are as defined in the above-mentioned general formula (1), in the presence of an acid catalyst.

There is no particular limitation on the method of synthesizing the hydroxy-fluorene derivative represented by the above general formula (7) and on the method of synthesizing the propargyl alcohol derivative represented by the above general formula (8). The hydroxy-fluorene derivative represented by the above general formula (7) can be synthesized by, for example, subjecting a carboxylic acid derivative represented by the following general formula (9),

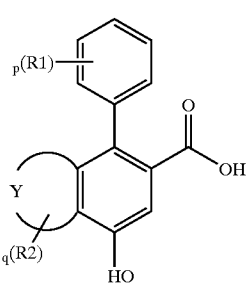 (9)

wherein R¹, R², p, q and a group represented by the following formula

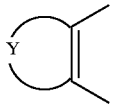

(2)

are as defined in the above-mentioned general formula (1),
to the Curtius rearrangement, to the Hofmann rearrangement or to the Lossen rearrangement to convert the carboxylic acid into an amine, converting a diazonium salt thereof into a bromide thereof through the Sandmeyer reaction, reacting the obtained bromide with magnesium or lithium to prepare an organometallic reagent, reacting the organometallic reagent with a ketone represented by the following formula (10),

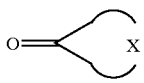

(10)

wherein a cyclic group containing X bonded to the oxygen atom (O) is as defined in the above-mentioned general formula (5),
at −10 to 70° C. for 10 minutes to 4 hours to obtain an alcohol derivative represented by the following formula (11),

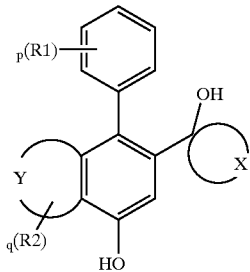

(11)

wherein R¹, R², p, q and groups represented by the following formulas,

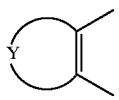 and 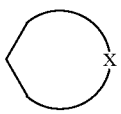

are as defined in the above-mentioned general formula (1),
and reacting the alcohol derivative under a neutral to acidic condition at 10 to 120° C. for 20 minutes to 2 hours to turn the alcohol into a spiro form. Here, when there is used a hydroxy-fluorenone derivative having a substituent on a ring containing Y (hereinafter also called Y-ring) of the hydroxy-fluorenone derivative, there can be synthesized a chromene compound having a substituent on the respective Y-rings.

The reaction ratio of the organometallic reagent that is prepared to the ketone represented by the above formula (10) can be selected over a wide range. Generally, however, the reaction ratio is selected over a range of from 1:10 to 10:1 (molar ratio). The reaction temperature is usually from −10 to 70° C., and the solvent that is used is a nonprotonic organic solvent such as diethyl ether, tetrahydrofurane, benzene or toluene.

Thereafter, the alcohol derivative that is obtained is turned into a spiro form under a neutral to acidic condition. As the acid catalyst, in this case, there can be preferably used acetic acid, hydrochloric acid, sulfuric acid, benzenesulfonic acid, p-toluenesulfonic acid or acidic alumina in an amount of from 0.1 to 10 parts by weight per 100 parts by weight of the alcohol derivative represented by the above formula (11). The reaction temperature is usually 10 to 120° C., and the solvent is, for example, acetic acid, tetrahydrofurane, benzene or toluene.

The propargyl alcohol derivative represented by the above-mentioned general formula (8) can be synthesized by, for example, reacting a ketone derivative corresponding to the above general formula (8) with a metal acetylene compound such as lithium acetylide.

The compound represented by the above general formula (7) is reacted with the compound represented by the general formula (8) in the presence of an acid catalyst in a manner, for example, as described below.

That is, the reaction ratio of these two compounds is selected over a wide range of, generally, from 1:10 to 10:1 (molar ratio). As the acid catalyst, there is used sulfuric acid, benzenesulfonic acid, p-toluenesulfonic acid, or acidic alumina in an amount of from 0.1 to 10 parts by weight per the total amount of 100 parts by weight of the compound represented by the above general formula (7) and the compound (reaction substrate) represented by the general formula (8). The reaction temperature is usually from 0 to 200° C., and the solvent is a nonprotonic organic solvent, such as N-methylpyrrolidone, dimethylformamide, tetrahydrofuran, benzene or toluene.

There is no particular limitation on the method of purifying the product. For example, a silica gel column purifying is conducted, followed by the recrystallization to purify the product.

The chromene compound of the present invention represented by the above general formula (1) dissolves well in a general organic solvent such as toluene, chloroform or tetrahydrofuran. When the chromene compound of the present invention is dissolved in such a solvent, the solvent generally exhibits a favorable photochromic action; i.e., the solvent is nearly colorless and transparent, quickly develops a color when it is irradiated with sunlight or ultraviolet rays, and reversibly and quickly returns to the initial colorless state when the irradiation with light is interrupted.

The above-mentioned photochromic action of the chromene compound of the present invention is similarly exhibited even in a high-molecular solid matrix. Therefore, the chromene compound of the present invention can be favorably used as a photochromic material for imparting photochromic properties to the high-molecular matrix. In particular, the chromene compound of the present invention exhibits a high color-developing sensitivity, a high color density, a large fading rate and a high light resistance even when it is dispersed in the high-molecular matrix having such a high hardness as the Rockwell hardness of 80 to 120, and is superior to the conventional chromene compounds in the above respects. The chromene compound of the present invention is useful as a photochromic material for the optical materials that require a high mechanical strength, such as plastic photochromic lenses for spectacles.

There can be used any high-molecular solid matrix provided it permits the chromene compound of the present invention to be homogeneously dispersed therein. Optically preferred examples include such thermoplastic resins as methyl polyacrylate, ethyl polyacrylate, methyl polymethacrylate, ethyl polymethacrylate, polystyrene, polyacrylonitrile, polyvinyl alcohol, polyacrylamide, poly (2-hydroxyethylmethacrylate), polydimethylsiloxane and polycarbonate.

There can be further exemplified multi-valent acrylic acids and multi-valent methacrylic acid ester compounds, such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl)propane, 2,2-bis(3,5-dibromo-4-methacryloyloxyethoxyphenyl)propane, trimethylolpropane trimethacrylate, and pentaerithritol tetramethacrylate; multi-valent allyl compounds, such as diallyl phthalate, diallyl terephthalate, diallyl isophthalate, diallyl tartarate, diallyl epoxysuccinate, diallyl fumarate, diallyl chloroendoate, diallyl hexaphthalate, diallyl carbonate, and allyl diglycol carbonate; multi-valent thioacrylic acid and multi-valent thiomethacrylic acid ester compounds such as 1,2-bis(methacryloylthio)ethane, bis(2-acryloylthioethyl)ether, and 1,4-bis(methacryloylthiomethyl)benzene; acrylic acid ester compounds and methacrylic acid ester compounds, such as glycidyl acrylate, glycidyl methacrylate, β-methylglicidyl methacrylate, bisphenol A-monoglycidylether methacrylate, 4-glycidyloxy methacrylate, 3-(glicidyl-2-oxyethoxy)-2-hydroxypropyl methacrylate, 3-(glycidyloxy-1-isopropyloxy)-2-hydroxypropyl acrylate, 3-glycidyloxy-2-hydroxypropyloxy)-2-hydroxypropyl acrylate and methoxypolyethylene glycol methacrylate; and thermosetting resins obtained by polymerizing radically polymerizable polyfunctional monomers such as divinyl benzene and the like.

There can be further exemplified copolymers of these monomers with unsaturated carboxylic acids such as acrylic acid, methacrylic acid and maleic anhydride; acrylic acid and methacrylic acid ester compounds such as methyl acrylate, methyl methacrylate, benzyl methacrylate, phenyl methacrylate, and 2-hydroxyethyl methacrylate, methyl ether polyethylene glycol methacrylate and γ-methacryloyloxypropyltrimethoxy silane; fumaric acid ester compounds such as diethyl fumarate and diphenyl fumarate; thioacrylic acid and thiomethacrylic acid ester compounds such as methylthio acrylate, benzylthio acrylate and benzylthio methacrylate; or radically polymerizable monofunctional monomers such as vinyl compounds like styrene, chlorostyrene, methyl styrene, vinyl naphthalene, α-methylstyrene dimer, bromostyrene, and methoxypolyethylene glycol allyl ether.

There is no particular limitation on the method of dispersing the chromene compound of the invention in the high-molecular solid matrix, and any generally employed method can be used. For example, the above thermoplastic resin and the chromene compound are kneaded together in a molten state and are dispersed in a resin. Or, the chromene compound is dissolved in the polymerizable monomer followed by the addition of a polymerization catalyst so as to be polymerized by heat or light, and is dispersed in the resin. Or, the surfaces of the thermoplastic resin and the thermosetting resin are dyed with the chromene compound so that it disperses in the resin.

The chromene compound of the present invention can be used as a photochromic material over a wide range, and is useful as various optical materials inclusive of the above-mentioned plastic photochromic lenses for spectacles. For example, the chromene compound of the invention can be used as various memory materials to substitute for the silver salt photosensitive material, copying material, photosensitive material for printing, memory material for cathode-ray tubes, photosensitive material for laser and photosensitive material for holography. Further, the photochromic material using the chromene compound of the present invention can be used as an optical filter material, a display material, an actinometer, an ornament, a coating film, etc.

When the chromene compound of the present invention is used as a photochromic material, there can be further used additives such as ultraviolet-ray stabilizer, ultraviolet-ray absorber, surfactant, antioxidant, radical-trapping agent, tint-preventing agent, antistatic agent, fluorescent dye, dye, pigment and perfume in order to improve light resistance of the photochromic compound, to improve color-developing rate and to improve color-fading rate. As the additives, known compounds can be used without any limitation. There is, either, no limitation on the form of use. Generally, however, it is desired that the two are used in a liquid medium in which the two dissolve homogeneously to come into favorable contact with each other so that the effect of the additive can be highly exhibited, or are used in the high-molecular matrix obtained by curing the liquid polymerizable monomer in which the two are homogeneously dissolved.

In general, the chromene compound is deteriorated by photo-oxidation. When used in a medium having excellent oxygen permeability or in a thin film in which oxygen easily diffuses, the chromene compound tends to lose its photochromic property. The chromene compound of the present invention exhibits excellent light resistance compared with the conventional chromene compounds. When used in a form described above, however, it is desired to also use an ultraviolet-ray stabilizer. Use of the ultraviolet-ray stabilizer helps obtain a higher light resistance. There is no problem in the light resistance when the chromene compound of the present invention is used being dispersed in a high molecular matrix having a thickness of not smaller than 1 mm. When used being dispersed in the high-molecular matrix having a thickness of smaller than 1 mm, furthermore smaller than 0.1 mm, however, it is desired that the chromene compound of the present invention is used together with the ultraviolet-ray stabilizer.

As the preferred ultraviolet-ray stabilizer, there can be used any known ultraviolet-ray stabilizer without limitation. From the standpoint of improving the light resistance, however, it is desired to use an extinguishing agent of oxygen in a singlet state and a hindered amine photo stabilizer (inclusive of a photo stabilizer having a hindered amine structure and a hindered phenol structure in a molecule).

The extinguishing agent of oxygen in the singlet state that is favorably used in the present invention may be a complex of $Ni^{2+}$ and an organic ligand, a cobalt (III)-tris-di-n-butyldithio carbamate, an iron (III)-diisopropyldithio carbamate and cobalt (II)-diisopropyldithio carbamate. Among these extinguishing agents of oxygen of the singlet state, the complex of $Ni^{2+}$ and the organic ligand is particularly preferred. Concrete examples of the complex include [2,2'-thiobis(4-(1,1,3,3-tetramethylbutyl)phenolato)butylamine] nickel, nickel-bis[o-ethyl(3,5-di-tert-butyl-4-hydroxybenzyl)]phosphonate, nickel-dibutyldithiocarbamate, bis[2,2'-thiobis-4-(1,1,3,3-tetramethylbutyl)phenolato]nickel, and various Ni complexes placed in the market by Ferro Corporation in the trade names of UV-Check AM-105, UV-Check AM-126 and UV-Check AM-205.

Concrete examples of the preferred hindered amine photostabilizer include bis(1,2,2,6,6-pentamethyl-4-piperidyl)sebacate, bis(2,2,6,6-tetramethyl-4-piperidyl)sebacate, 1-[2-{3-(3,5-di-t-butyl-4-hydroxyphenyl)propionyloxy}ethyl]-4-{3-(3,5-di-t-butyl-4-hydroxyphenyl)propionyloxy]-2,2,6,6-tetramethyl piperidine, 2-methyl-acrylic acid 1,2,2,6,6-pentamethyl-piperidine-4-il ester, 2-methyl-acrylic acid 2,2,6,6-tetramethyl-piperidine-4-il ester, succinic acid-bis(2,2,6,6-tetramethyl-4-piperidinyl)ester, 2-(3,5-di-t-butyl-4-hydroxybenzyl)-2-n-butylmalonic acid bis(1,2,2,6,6-pentamethyl-4-piperidyl), propanedionic acid, [(4-methoxyphenyl)-methylene] and bis(1,2,2,6,6-pentamethyl-4-piperidinyl)ester.

As the hindered amine photo stabilizer, there can be exemplified Sumisorb LS-2000 and LS-2001 (trade names) manufactured by Sumitomo Kagaku Co.

Though there is no particular limitation on the ratio of blending the ultraviolet-ray stabilizer, it is desired to use it in an amount of from 0.01 to 10000 parts by weight and, particularly, from 10 to 500 parts by weight per 100 parts by weight of the chromene compound of the present invention.

As the additive other than the ultraviolet-ray stabilizer, the following compounds can be used. That is, the surfactant may be any one of the nonionic type, anionic type or cationic type. As the antioxidant, radical-trapping agent and ultraviolet-ray absorber, there can be favorably used hindered phenol antioxidant, phenol-type radical-trapping agent, sulfur-type antioxidant, benzotriazole compound, and benzophenone compound. These surfactants, antioxidants, radical-trapping agents and ultraviolet-ray absorbers may be used in two or more kinds for the photochromic material of the present invention. It is desired that the surfactants, antioxidants, radical-trapping agents and ultraviolet-ray absorbers are added in amounts of from 0.01 to 10000 parts by weight per 100 parts by weight of the chromene compound of the present invention.

There is no particular limitation on the method of using the photochromic material of the present invention comprising the chromene compound of the present invention as a photochromic lens provided a homogeneous dimming performance is obtained. Examples of the method that can be preferably used include a method according to which a polymer film in which the photochromic material of the present invention is homogeneously dispersed is sandwiched in a lens, a method according to which the photochromic material of the present invention is dispersed in the above-mentioned polymerizable monomer and is polymerized according to a predetermined method, a method according to which a plastic lens is immersed in a solution obtained by dissolving the photochromic material of the present invention in a solvent such as a silicone oil, treated at 150 to 200° C. for 10 to 60 minutes so that the surfaces of the lens is impregnated with the chromene compound and, then, the surfaces are covered with a curable material, and a method according to which a polymer film in which the photochromic material of the present invention is homogeneously dispersed is stuck to the surface of the plastic lens, and the surface is coated with a curable material.

Among the above-mentioned methods, a particularly useful method is the one which cures by polymerization the photochromic curable composition (composition of the present invention) containing a polymerizable monomer and the photochromic material of the present invention, since it makes it possible to stably and efficiently obtain lenses of high quality.

There is no particular limitation on the polymerizable monomer used for the composition of the present invention provided it dissolves the chromene compound of the present invention, and there can be used a mixture of a polyfunctional isocyanate and a polyfunctional mercapto compound, a mixture of a polyfunctional isocyanate and a polyfunctional hydroxy compound, a polyfunctional epoxy compound and a radically polymerizable monomer. Among them, from the standpoint of obtaining optical products such as photochromic plastic lenses, it is desired to use the radically polymerizable monomer and, particularly, the above-mentioned (meth)acrylate radically polymerizable monomer because of its excellent transparency, mechanical strength and photochromic properties of the cured product.

In the composition of the present invention, there is no particular limitation on the amount of adding the photochromic compound. Generally, however, the photochromic compound is added in an amount of from 0.001 to 10 parts by weight per 100 parts by weight of the total polymerizable monomers. When the amount of addition of the photochromic compound is not larger than 0.001 part by weight, the color density often becomes low. When the amount of addition is not smaller than 10 parts by weight, on the other hand, the photochromic compound is not sufficiently dissolved in the polymerizable monomer and becomes inhomogeneous developing shading in the color density.

There is no particular limitation on the method of curing the photochromic polymerizable composition of the present invention, and a known polymerization method can be employed depending upon the kind of the monomer that is used. The polymerization can be initiated by using a radical polymerization initiator such as various peroxides and azo compounds, by the irradiation with ultraviolet rays, α-rays, β-rays or γ-rays, or by utilizing both of them.

There is no particular limitation, either, on the polymerization method when the photochromic polymerizable composition is used as an optical material such as a photochromic lens, however, it is desired to employ the cast polymerization. A-representative cast polymerization method will now be described in detail.

According to this method, the curable composition of the present invention to which the radically polymerizable initiator is added, is poured into between the molds held by an elastomer gasket or a spacer, heated in an air furnace so as to be cured by polymerization, and is taken out therefrom.

There is no particular limitation on the radical polymerization initiator, and known ones can be used. Representative examples include diallyl peroxides such as benzoyl peroxide, p-chlorobenzoyl peroxide, decanoyl peroxide, lauroyl peroxide and acetyl peroxide; peroxy esters such as t-butylperoxy-2-ethyl hexanoate, t-butylperoxy dicarbonate, cumylperoxy neodecanate and t-butylperoxy benzoate; percarbonates such as diisopropylperoxy dicarbonate, di-2-ethylhexylperoxy dicarbonate and di-sec-butyloxy carbonate; and azo compounds such as 2,2'-azobisisobutylonitrile, 2,2'-azobis(4-dimethylvaleronitrile), 2,2'-azobis(2-methylbutylonitrile) and 1,1'-azobis(cyclohexane-1-carbonitrile), etc.

The amount of the radical polymerization initiator varies depending upon the polymerization conditions, kind of the initiator, and kind and composition of the curable composition of the present invention, and cannot be definitely stated. Generally, however, the radical polymerization initiator is used in an amount of from 0.001 to 10 parts by weight per 100 parts by weight of the whole polymerizable monomers.

Among the polymerization conditions, the temperature, in particular, affects the properties of the obtained resin. The temperature conditions vary depending upon the kind and amount of the initiator and the kind of the monomer, and cannot be definitely stated. Generally, however, a so-called tapered two-stage polymerization is conducted by starting the polymerization at a relatively low temperature, slowly raising the temperature and curing the composition at a high temperature at the time when the polymerization has finished.

The polymerization time, too, varies depending upon various factors like the temperature and it is desired to determine an optimum time in advance depending upon the conditions. Generally, however, it is desired to so select the condition that the polymerization is completed in 2 to 40 hours.

Further, the cast polymerization can be similarly conducted even by the known photo polymerization using ultraviolet rays. As the photopolymerization initiator, in this case, there can be used 2,4,6-trimethylbenzoyldiphenylphosphine oxide, bis(2,6-dimethoxybenzoyl)-2,4,4-trimethyl-pentylphosphine oxide, benzoin, benzoinmethyl ether, benzoinbutyl ether, benzophenol, acetophenone 4,4'-dichlorobenzophenone, diethoxyacetophenone, 2-hydroxy-2-methyl-1-phenylpropane-1-one, benzylmethyl ketal, 1-(4-isopropylphenyl)-2-hydroxy-2-methylpropane-1-one, 1-hydroxycyclohexylphenyl ketone, and 2-isopropylthioxanthone. In general, these photopolymerization initiators are used in an amount of from 0.001 to 5 parts by weight per 100 parts by weight of the whole monomers.

The high molecular matrix obtained by curing the photochromic polymerizable monomer of the invention obtained by the method described above can be put to the following treatment depending upon the use. That is, a dying using a dye such as a dispersion dye; a hard-coating treatment by using a hard-coating agent comprising chiefly a silane coupling agent and a sol of an oxide of silicon, zirconium, antimony or aluminum, or a hard-coating agent comprising chiefly an organic high-molecular material; a reflection-preventing treatment by depositing a thin film of a metal oxide such as $SiO_2$, $TiO_2$, or $ZrO_2$ or by applying a thin film of an organic high-molecular material; antistatic treatment; and secondary treatment.

EXAMPLES

The present invention will be described in further detail by way of Examples to which only, however, the invention is in no way limited.

Example 1

1.0 Grams (0.0032 mols) of the following 5-hydroxy-(7H)benzo(c)fluorene derivative

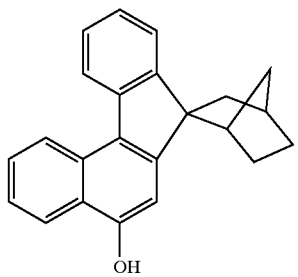

and 0.94 g (0.0032 mols) of the following propargyl alcohol derivative

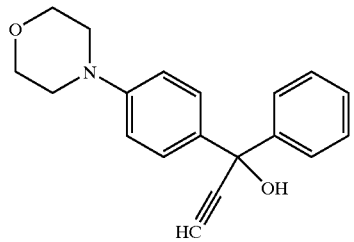

were dissolved in 50 ml of toluene followed by the addition of 0.05 g of p-toluenesulfonic acid, and were heated, refluxed and stirred for 30 minutes. After the reaction, the solvent was removed, and the reaction product was refined by chromatography on silica gel to obtain 0.6 g of a pale yellowish powdery product, yield, 32%.

Elemental analysis of the product showed C 86.05%, H 6.46%, N 2.21%, O 5.28%, which were in very good agreement with the calculated values of C 85.83%, H 6.35%, N 2.38%, O 5.44% of $C_{42}H_{37}NO_2$.

A measurement of a proton nuclear magnetic resonance spectrum indicated, as shown in FIG. 1, peaks of 10H based on a methine and a methylene proton of norbornylidene group near δ 1.0 to 3.0 ppm, peaks of 8H based on a methylene proton of morpholino group near δ 3.0 to 4.0 ppm, and peaks of 19H based on an aromatic proton and an alkene proton near δ 5.6 to 9.0 ppm.

In FIG. 1, highly intense peaks appearing at about δ 7.2 and 1.5 ppm are those stemming from impurities in the $DCCl_3$ used as a solvent.

Further, a measurement of a $^{13}C$— nuclear magnetic resonance spectrum indicated a peak based on a carbon atom of an aromatic ring near δ 110 to 160 ppm, a peak based on a carbon atom of an alkene near δ 80 to 140 ppm, and a peak based on a carbon atom of an alkyl at δ 20 to 60 ppm.

From the above results, it was confirmed that the isolated product was a compound represented by the following structural formula,

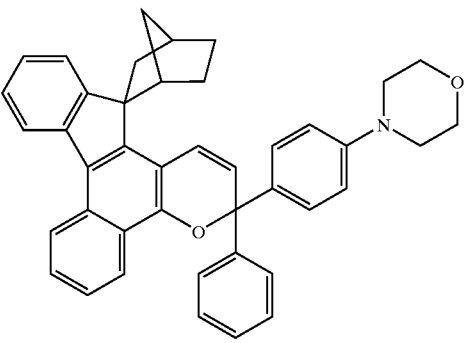

Examples 2 to 84

Chromene compounds shown in Tables 1 to 21 were synthesized in the same manner as in Example 1. The obtained products were analyzed for their structures relying on the same means for confirming structure as that of Example 1. It was confirmed that the obtained products were the compounds represented by the structural formulas shown in Tables 1 to 21. Tables 22 to 27 show values of elemental analysis of these compounds, values calculated from the structural formulas of these compounds, and characteristic spectra in $^1$H-NMR spectra.

TABLE 1
| Ex. No. | Starting material | |
|---|---|---|
| | Benzofluorene derivative | Propargyl alcohol derivative |
| 2 | 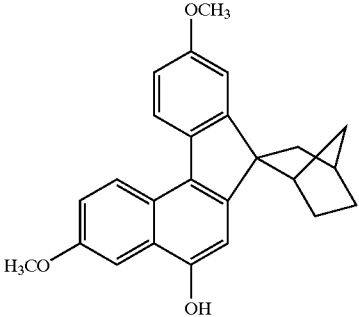 | 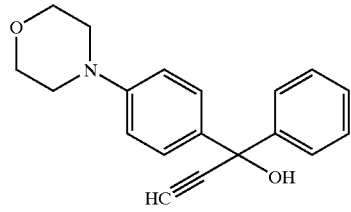 |
| 3 | 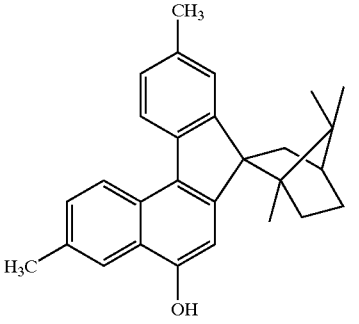 | 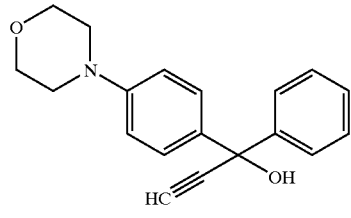 |
| 4 | 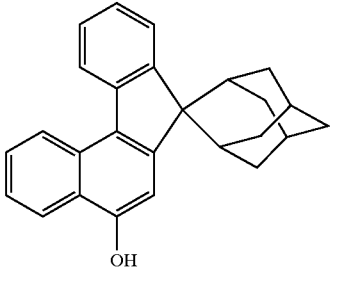 | 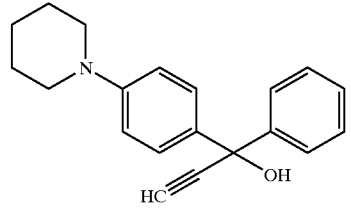 |
| 5 | 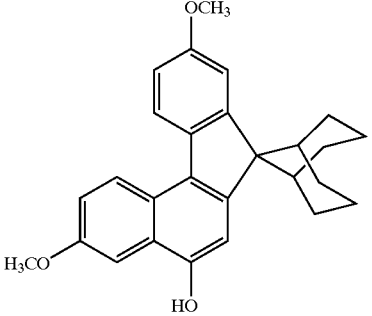 | 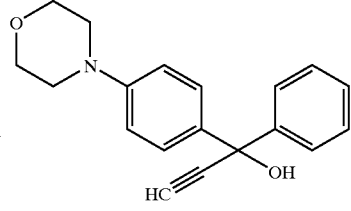 |

TABLE 1-continued
| Ex. No. | product | Yield (%) |
|---|---|---|
| 2 | 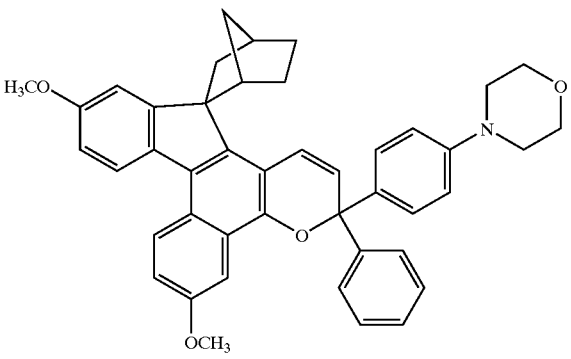 | 30 |
| 3 | 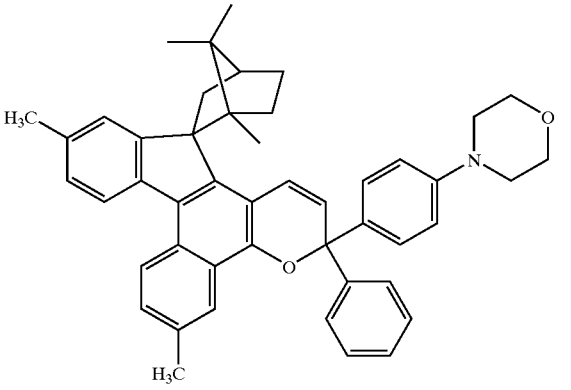 | 32 |
| 4 | 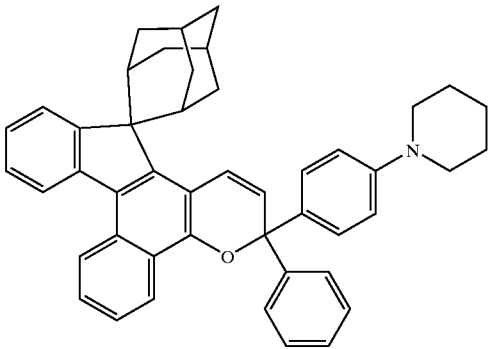 | 28 |
| 5 | 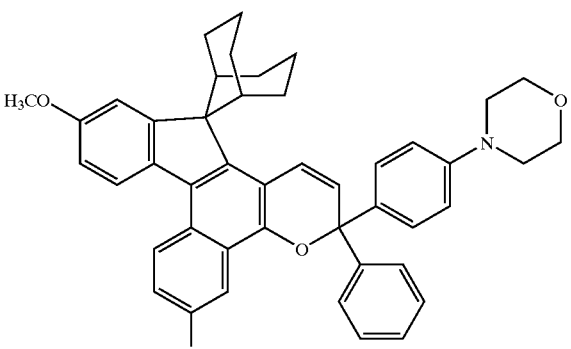 | 26 |

TABLE 2

| Ex. | Starting material | |
|---|---|---|
| No. | Benzofluorene derivative | Propargyl alcohol derivative |
| 6 | | |
| 7 | | |
| 8 | | |
| 9 | | |

TABLE 2-continued

| Ex. No. | product | Yield (%) |
|---|---|---|
| 6 | (structure: indeno-fused naphthopyran with norbornyl group, 4-morpholinophenyl and 4-methoxyphenyl substituents) | 36 |
| 7 | (structure: indeno-fused naphthopyran with adamantyl group, 4-(dimethylamino)phenyl and phenyl substituents) | 31 |
| 8 | (structure: indeno-fused naphthopyran with bicyclic group, 4-piperidinophenyl and phenyl substituents) | 34 |
| 9 | (structure: indeno-fused naphthopyran with tricyclic group, 4-indolinylphenyl and phenyl substituents) | 29 |

TABLE 3

| Ex. No. | Starting material | |
|---|---|---|
| | Benzofluorene derivative | Propargyl alcohol derivative |
| 10 | | |
| 11 | | |
| 12 | | |
| 13 | | |

TABLE 3-continued

| Ex. No. | product | Yield (%) |
|---|---|---|
| 10 | | 30 |
| 11 | | 35 |
| 12 | | 29 |
| 13 | | 31 |

TABLE 4
| Ex. No. | Starting material | |
|---|---|---|
| | Benzofluorene derivative | Propargyl alcohol derivative |
| 14 | 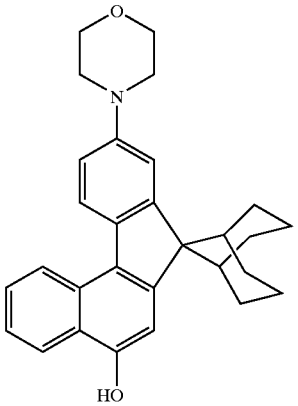 | 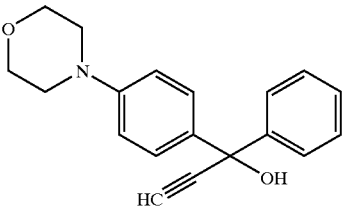 |
| 15 | 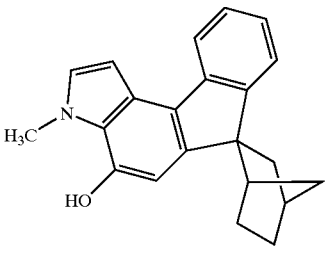 | 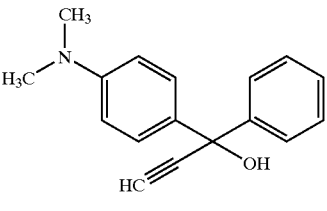 |
| 16 | 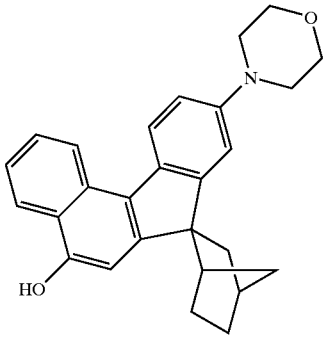 | 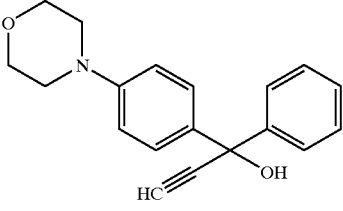 |
| 17 | 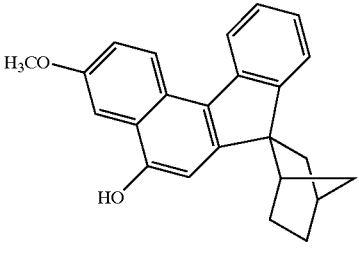 | 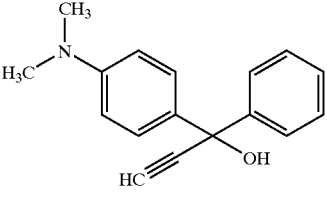 |

TABLE 4-continued
| Ex. No. | product | Yield (%) |
|---|---|---|
| 14 | 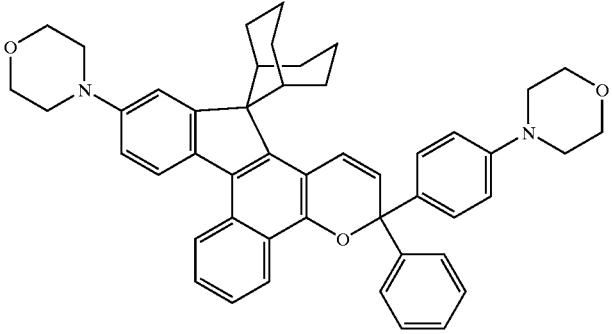 | 32 |
| 15 | 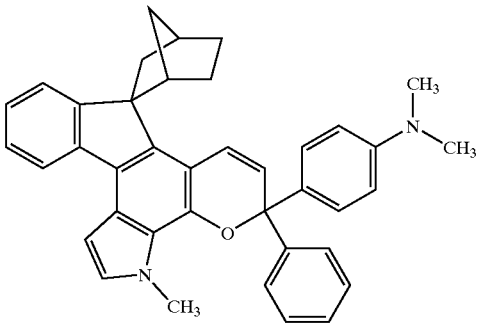 | 13 |
| 16 | 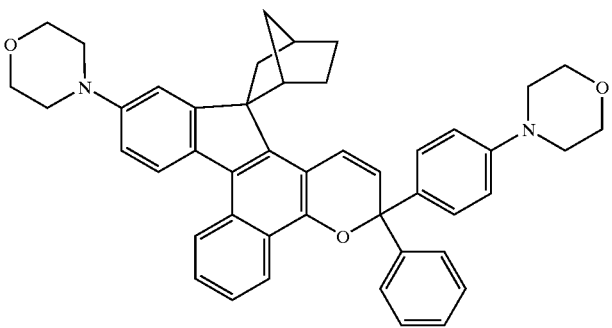 | 25 |
| 17 | 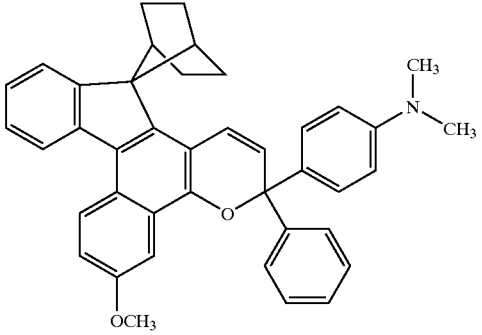 | 33 |

TABLE 5

| Ex. No. | Starting material | |
|---|---|---|
| | Benzofluorene derivative | Propargyl alcohol derivative |
| 18 | [structure: 2,3-dimethoxy-benzofluorene with OH and norbornyl substituents] | [structure: 4-(dimethylamino)phenyl phenyl propargyl alcohol] |
| 19 | [structure: tetramethoxy benzofluorene with OH and norbornyl] | [structure: 4-piperidinophenyl phenyl propargyl alcohol] |
| 20 | [structure: dimethoxy-benzofluorene with OH and norbornyl] | [structure: 4-(dimethylamino)phenyl phenyl propargyl alcohol] |
| 21 | [structure: methoxy-benzofluorene with OH and norbornyl] | [structure: 4-(dimethylamino)phenyl 4-methoxyphenyl propargyl alcohol] |

| Ex. No. | product | Yield (%) |
|---|---|---|
| 18 | [structure of chromene product with dimethoxy, dimethylamino-phenyl, phenyl, and norbornyl substituents] | 14 |

TABLE 5-continued
| | | |
|---|---|---|
| 19 | 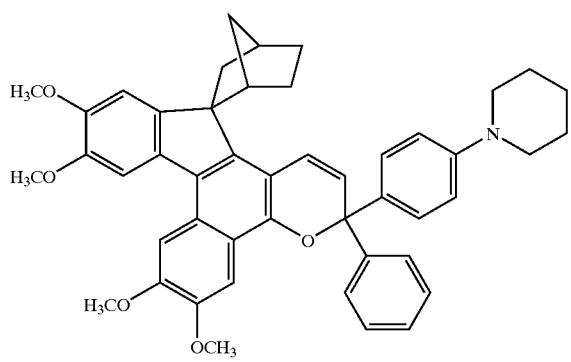 | 22 |
| 20 | 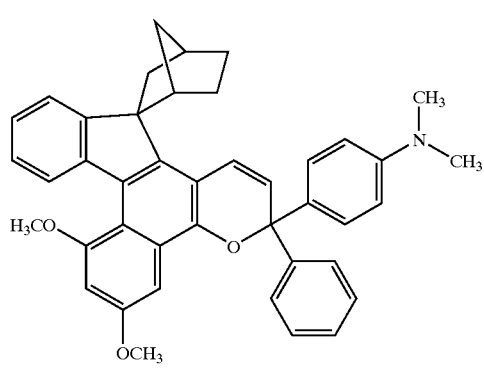 | 15 |
| 21 | 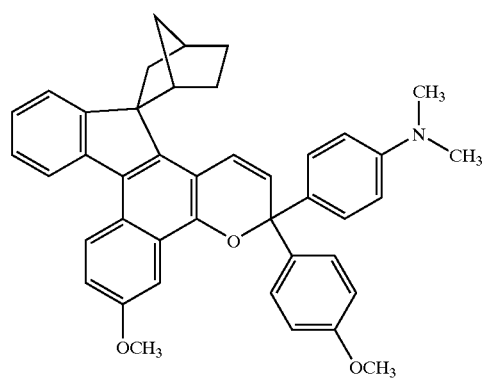 | 22 |
TABLE 6
| Ex. | Starting material | |
|---|---|---|
| No. | Benzofluorene derivative | Propargyl alcohol derivative |
| 22 | 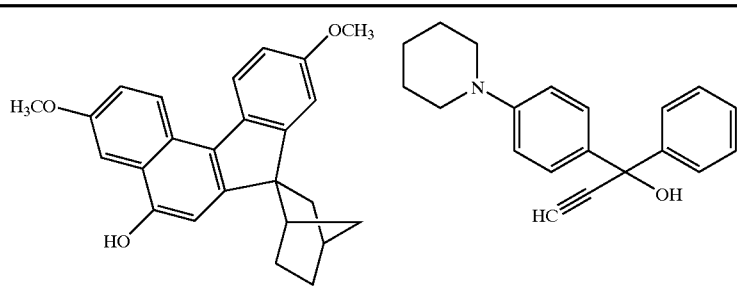 | |

TABLE 6-continued
| | | |
|---|---|---|
| 23 | 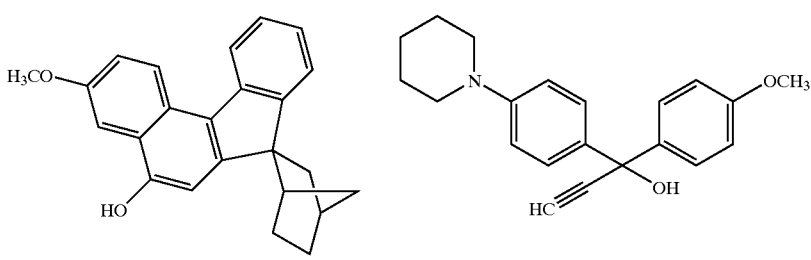 | |
| 24 | 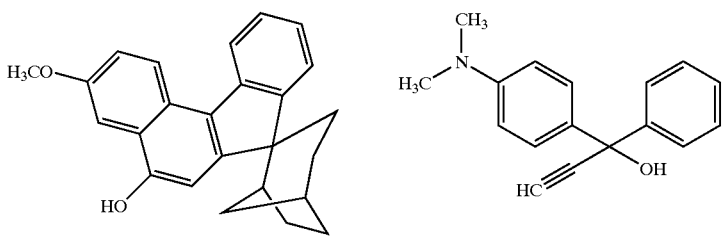 | |
| 25 | 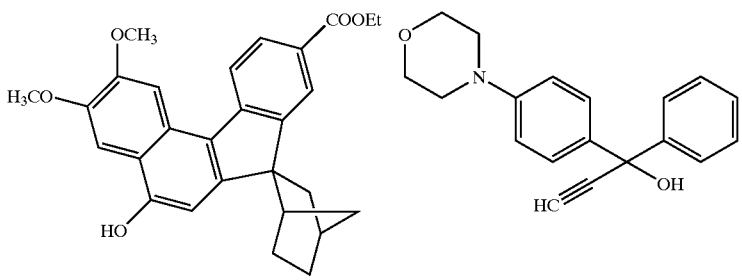 | |
| Ex. No. | product | Yield (%) |
|---|---|---|
| 22 | 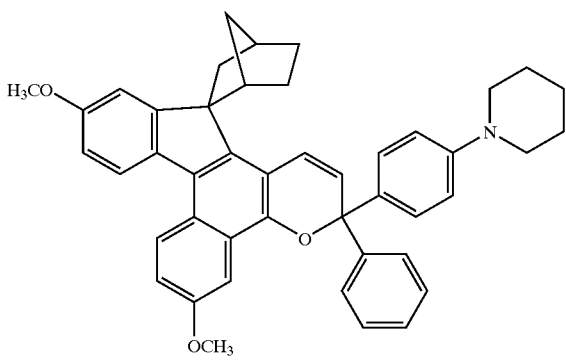 | 14 |
| 23 | 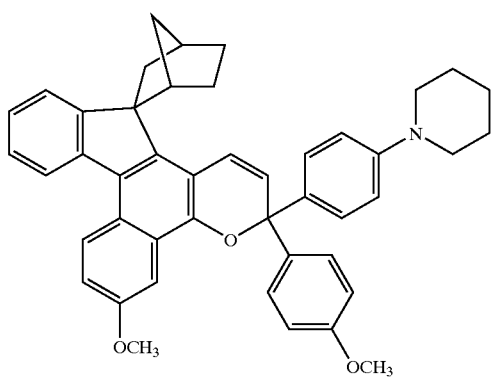 | 18 |

TABLE 6-continued
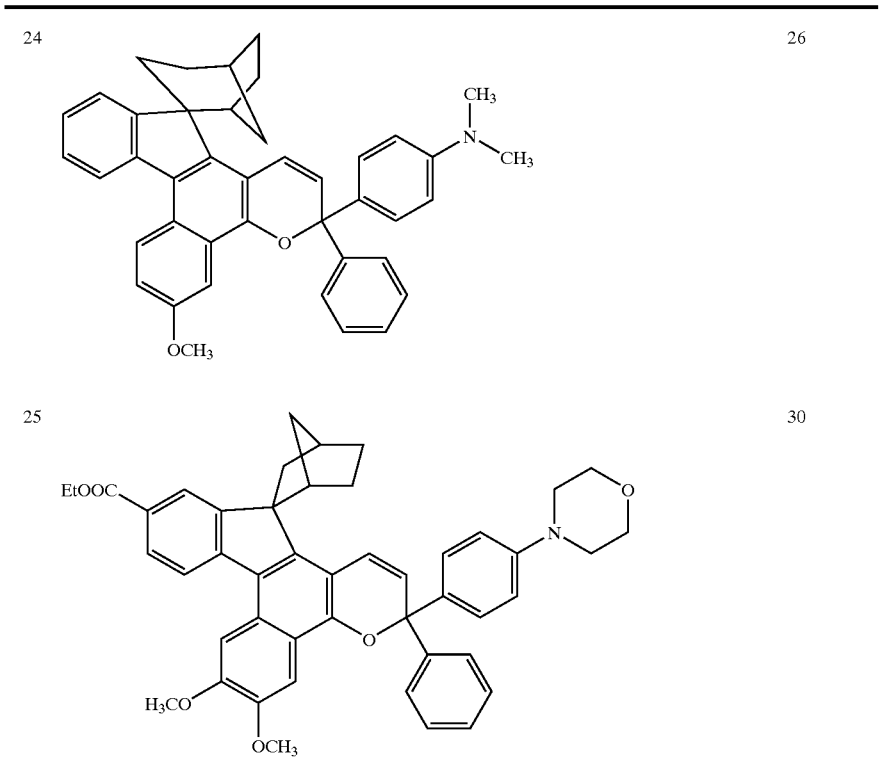
| | |
|---|---|
| 24 | 26 |
| 25 | 30 |
TABLE 7
| Ex. No. | Starting material | |
|---|---|---|
| | Benzofluorene derivative | Propargyl alcohol derivative |
| 26 | 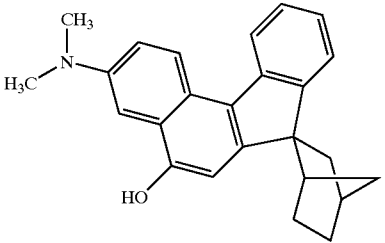 | 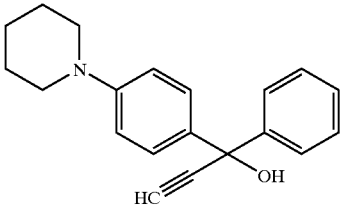 |
| 27 | 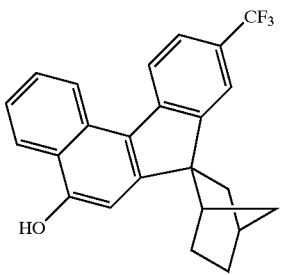 | 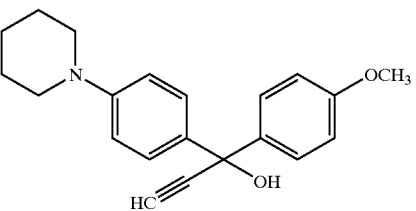 |

TABLE 7-continued
| 28 | 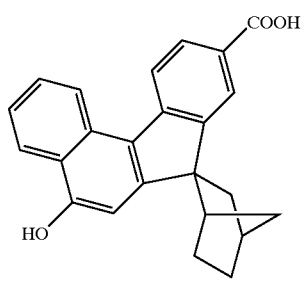 | 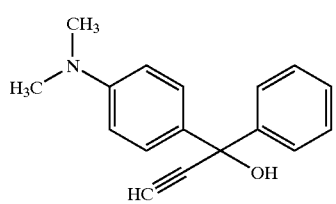 |
| 29 | 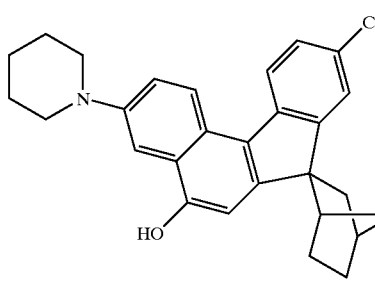 | 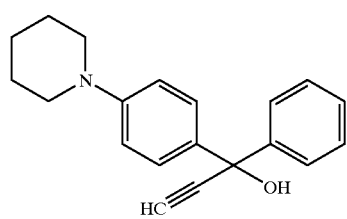 |
| Ex. No. | product | Yield (%) |
| --- | --- | --- |
| 26 | 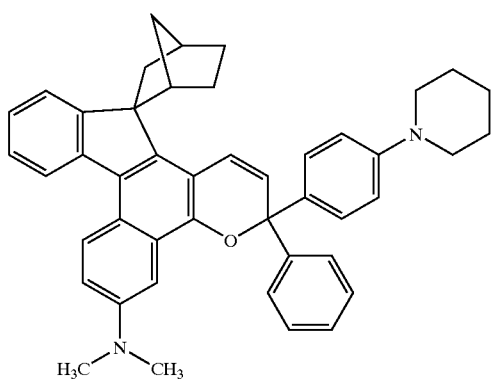 | 14 |
| 27 | 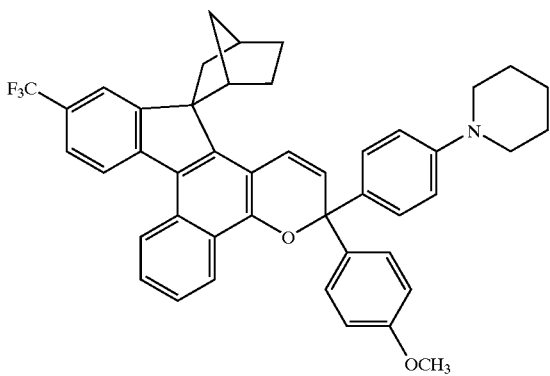 | 33 |

TABLE 7-continued
28 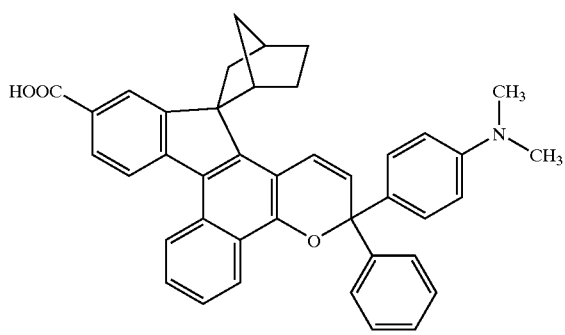 26
29 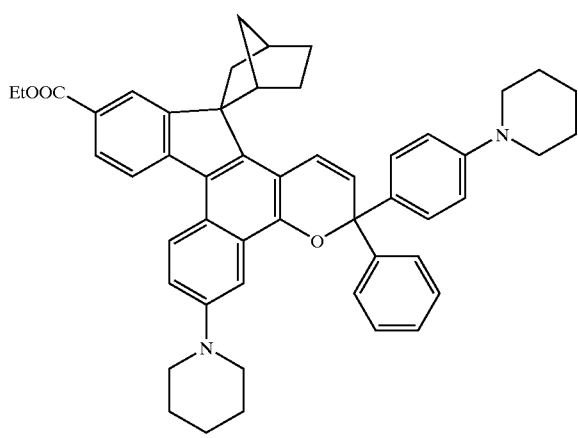 29
TABLE 8
| Ex. | Starting material | |
|---|---|---|
| No. | Benzofluorene derivative | Propargyl alcohol derivative |
| 30 | 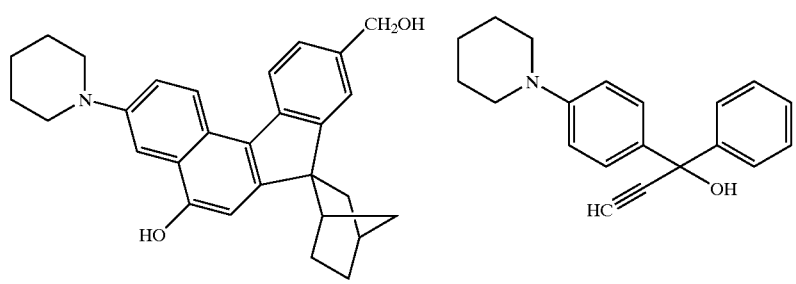 | |
| 31 | 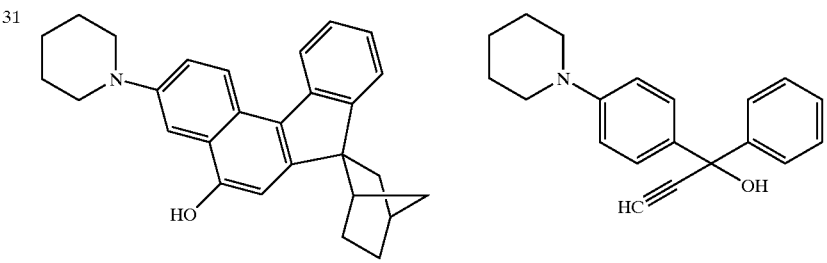 | |

TABLE 8-continued
| 32 | 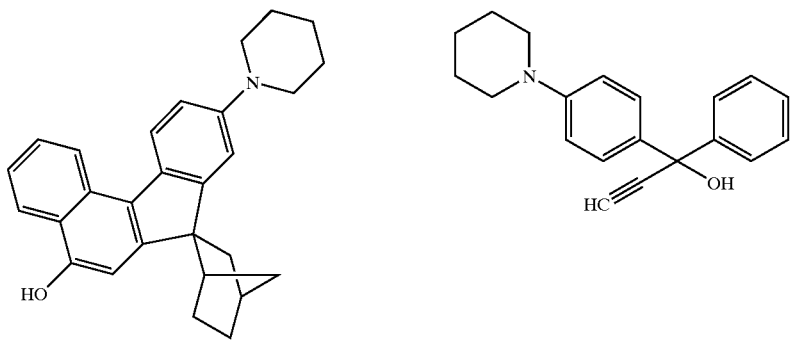 |
| 33 | 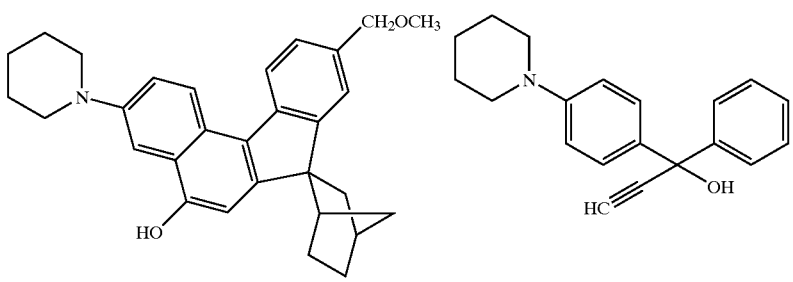 |
| Ex. No. | product | Yield (%) |
| --- | --- | --- |
| 30 | 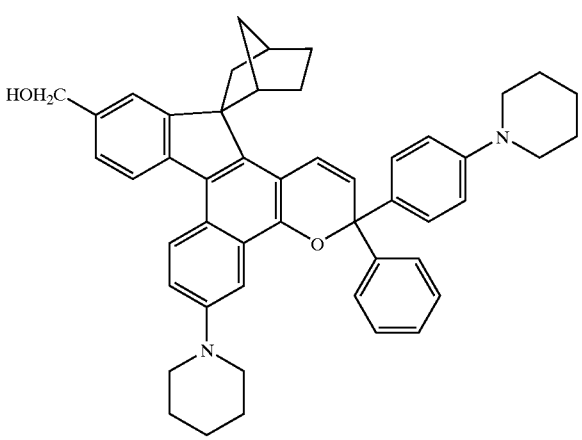 | 12 |
| 31 | 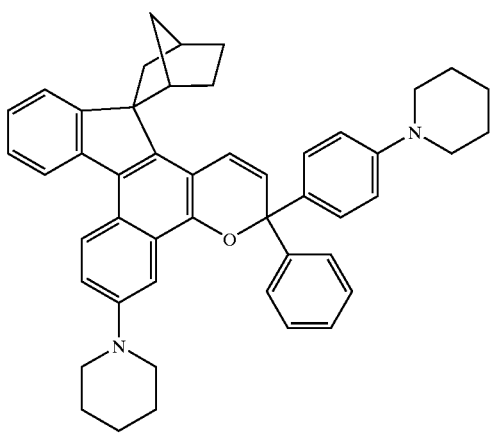 | 35 |

TABLE 8-continued

| Ex. No. | Structure | (col) |
|---|---|---|
| 32 | [structure] | 11 |
| 33 | [structure] | 16 |

TABLE 9

| Ex. No. | Starting material | |
|---|---|---|
| | Benzofluorene derivative | Propargyl alcohol derivative |
| 34 | [structure] | [structure] |
| 35 | [structure] | [structure] |

TABLE 9-continued
| 36 | 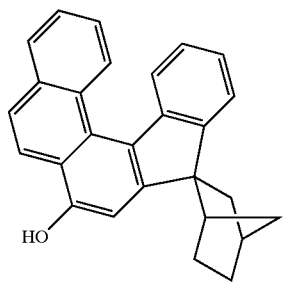 | 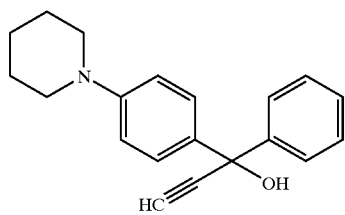 |
| 37 | 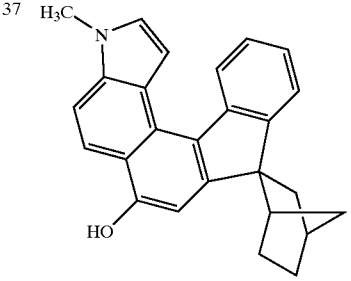 | 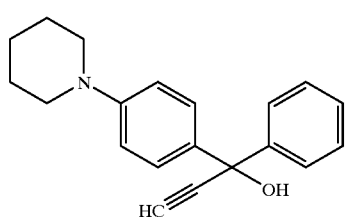 |
| Ex. No. | product | Yield (%) |
| --- | --- | --- |
| 34 | 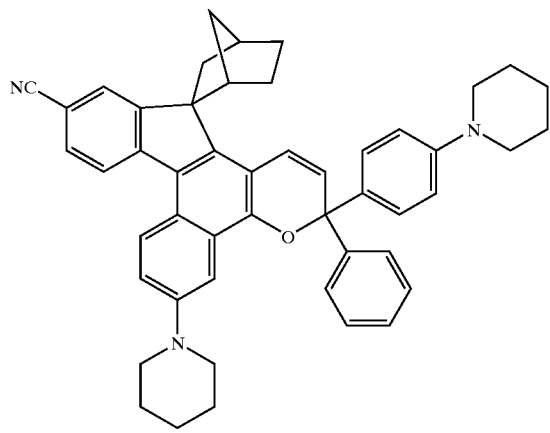 | 8 |
| 35 | 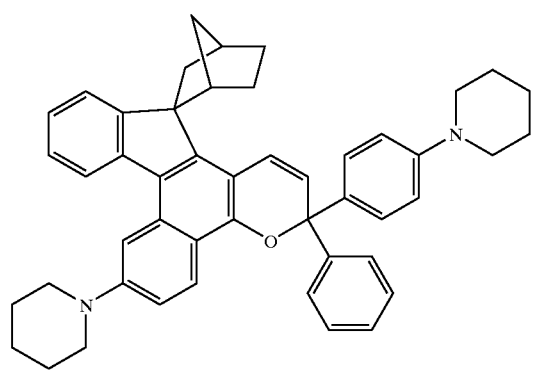 | 22 |

TABLE 9-continued
36 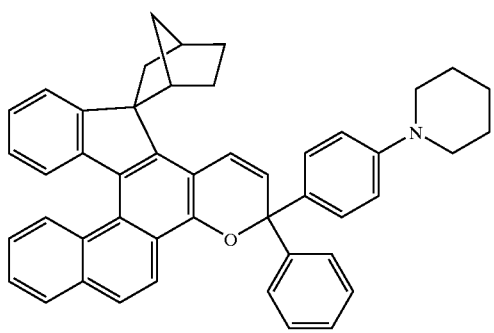 16
37 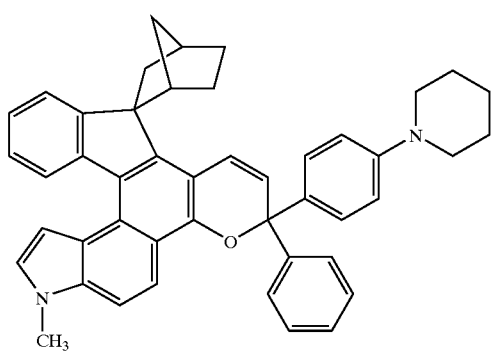 22
TABLE 10
| Ex. | Starting material | |
|---|---|---|
| No. | Benzofluorene derivative | Propargyl alcohol derivative |
| 38 | 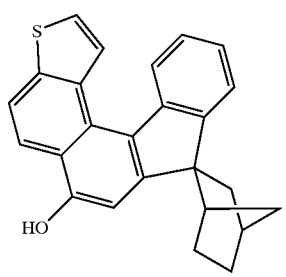 | 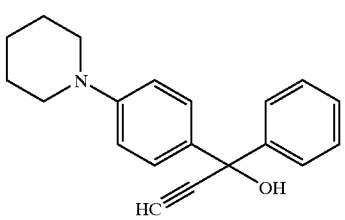 |
| 39 | 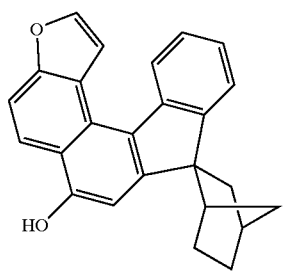 | 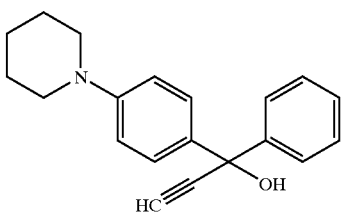 |

TABLE 10-continued
| 40 | 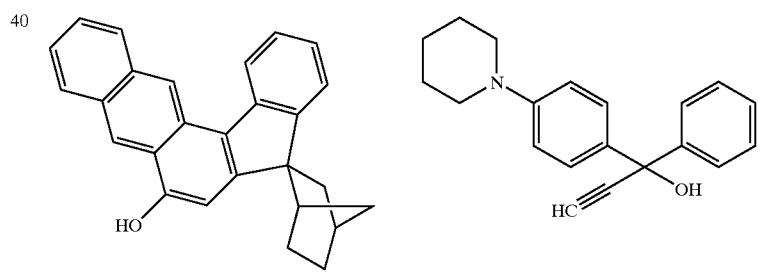 | 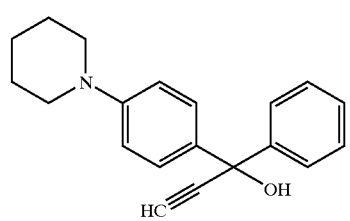 |
| 41 | 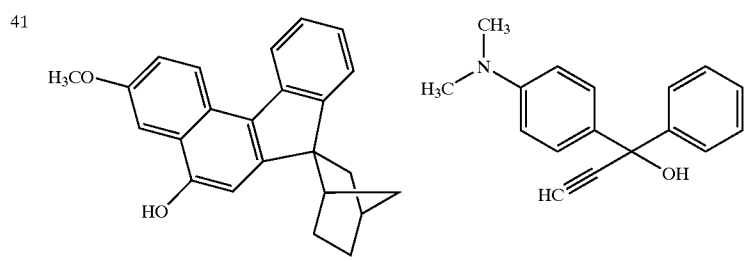 | 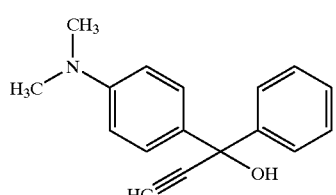 |
| Ex. No. | product | Yield (%) |
|---|---|---|
| 38 | 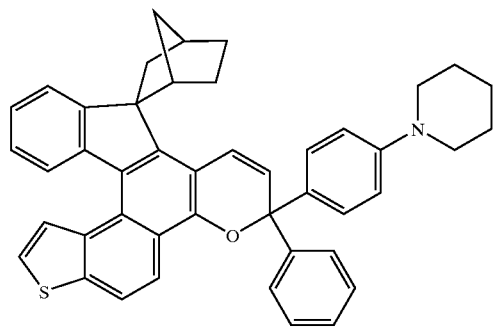 | 30 |
| 39 | 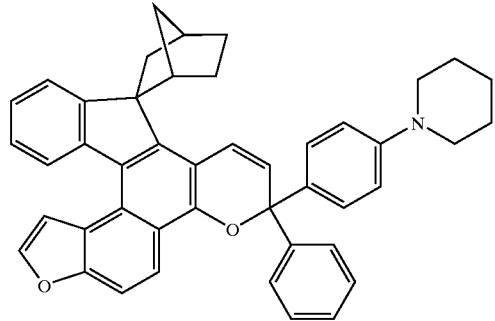 | 9 |

TABLE 10-continued
| 40 | 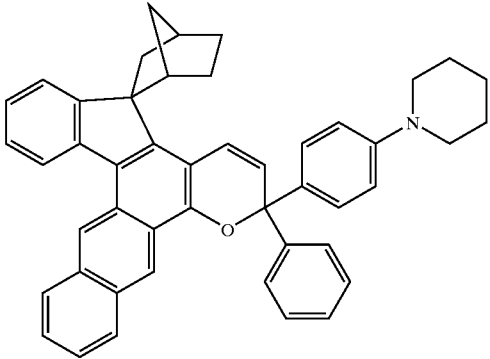 | 5 |
| 41 | 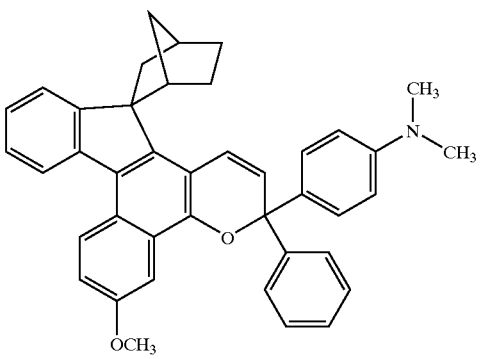 | 15 |
TABLE 11
| Ex. | Starting material | |
|---|---|---|
| No. | Benzofluorene derivative | Propargyl alcohol derivative |
| 42 | 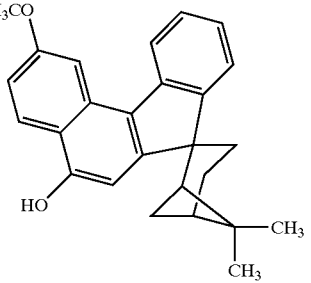 | 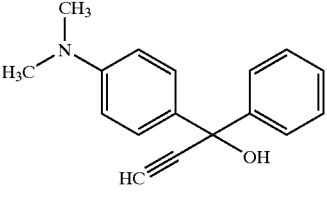 |
| 43 | 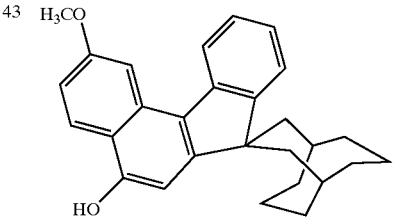 | 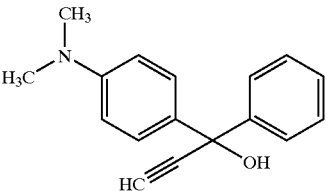 |

TABLE 11-continued
| 44 | 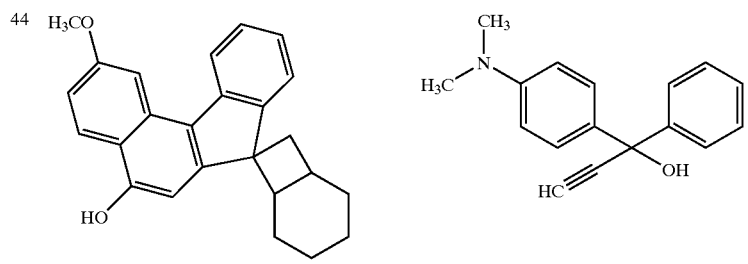 |
| --- | --- |
| 45 | 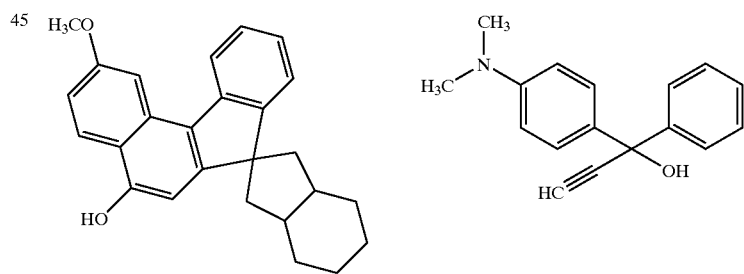 |
| Ex. No. | product | Yield (%) |
| --- | --- | --- |
| 42 | 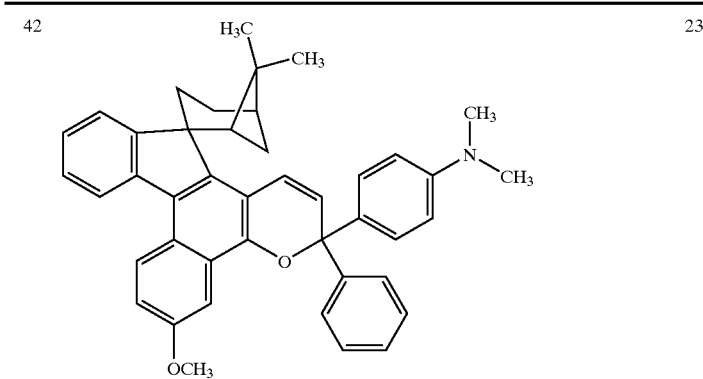 | 23 |
| 43 | 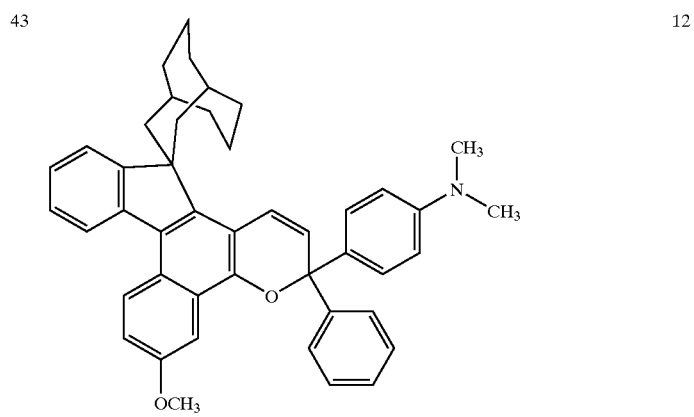 | 12 |

TABLE 11-continued
| | | |
|---|---|---|
| 44 | 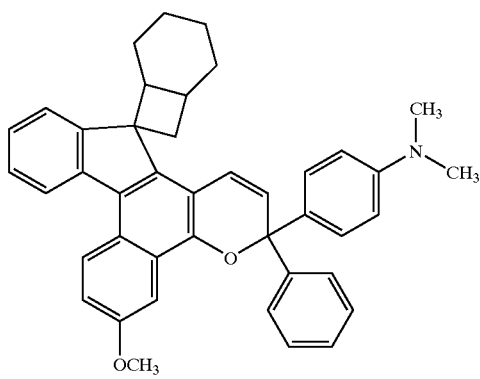 | 9 |
| 45 | 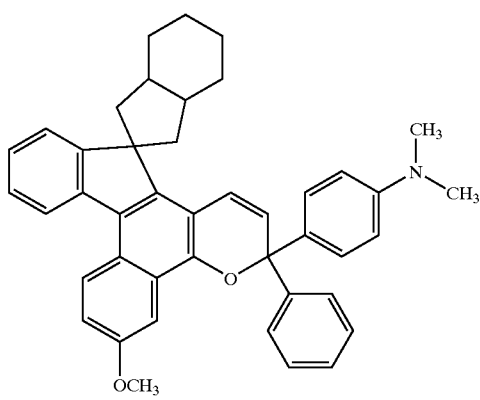 | 13 |
TABLE 12
| Ex. No. | Starting material | |
|---|---|---|
| | Benzofluorene derivative | Propargyl alcohol derivative |
| 46 | 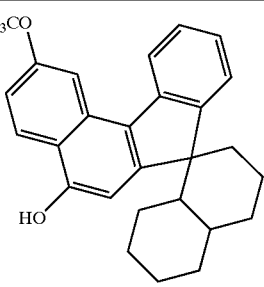 | 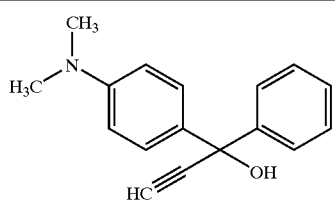 |
| 47 | 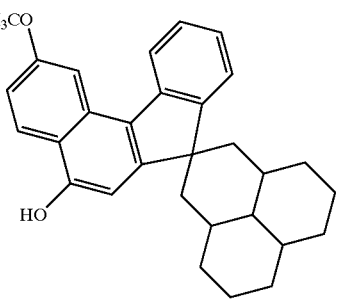 | 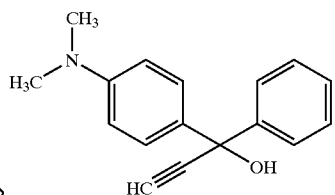 |

TABLE 12-continued
| 48 | 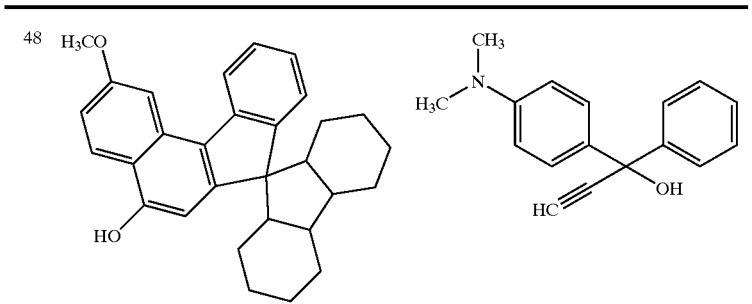 |
| 49 | 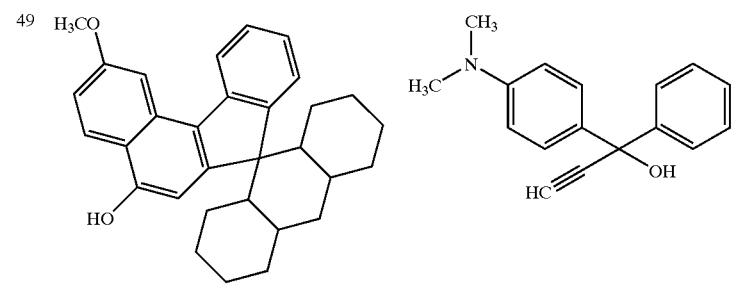 |
| Ex. No. | product | Yield (%) |
| --- | --- | --- |
| 46 | 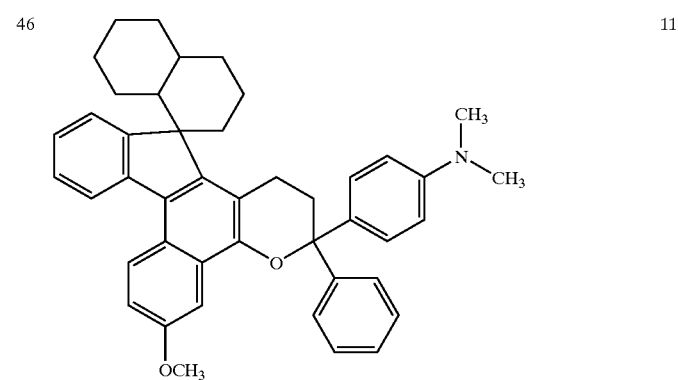 | 11 |
| 47 | 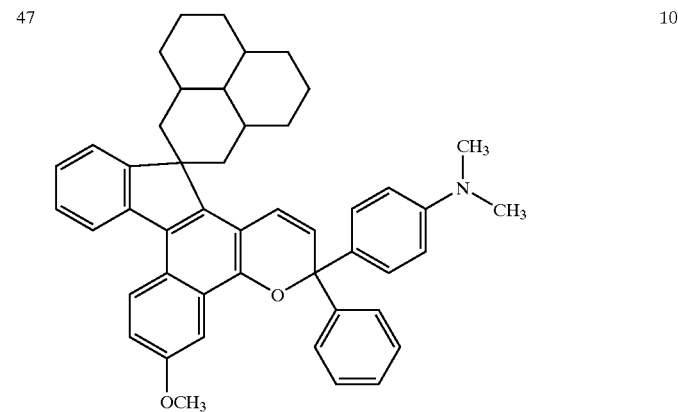 | 10 |

TABLE 12-continued
| | | |
|---|---|---|
| 48 | 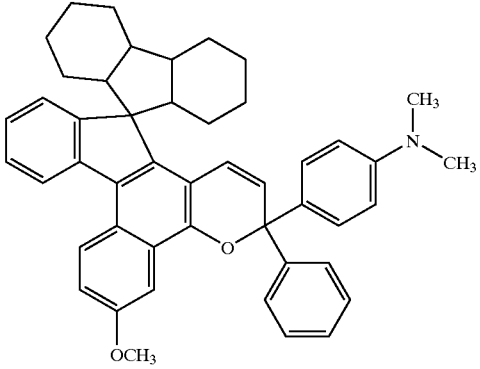 | 5 |
| 49 | 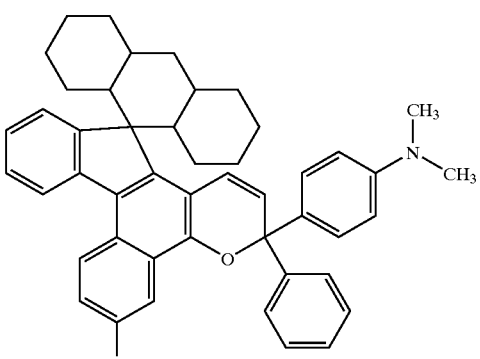 | 17 |
TABLE 13
| Ex. | Starting material | |
|---|---|---|
| No. | Benzofluorene derivative | Propargyl alcohol derivative |
| 50 | 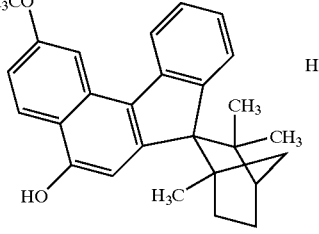 | 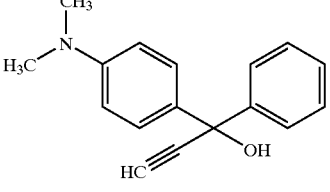 |
| 51 | 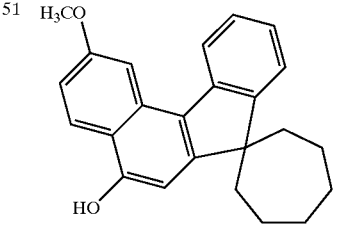 | 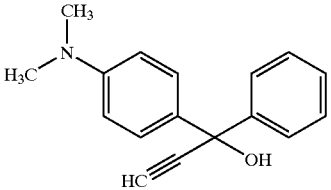 |

TABLE 13-continued
| 52 | 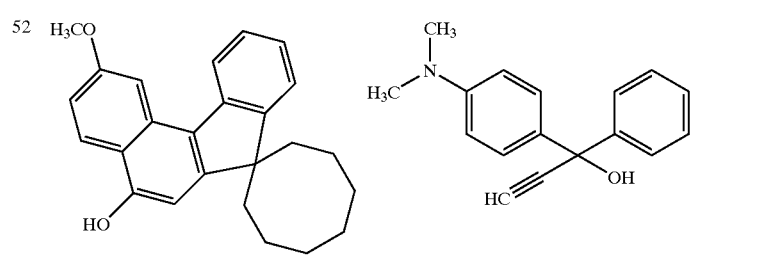 |
| 53 | 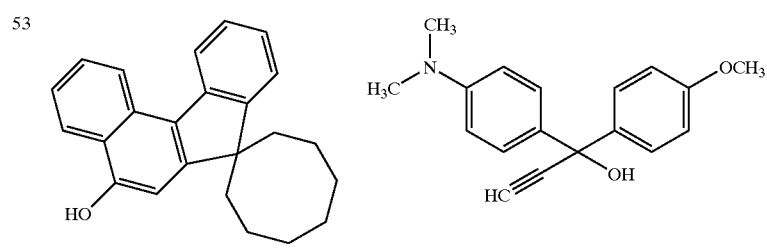 |
| Ex. No. | product | Yield (%) |
| --- | --- | --- |
| 50 | 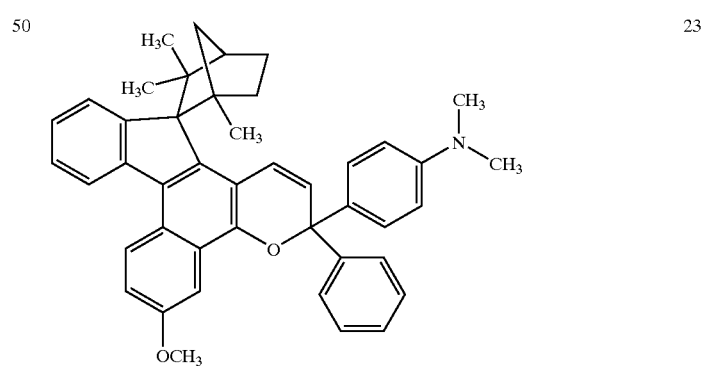 | 23 |
| 51 | 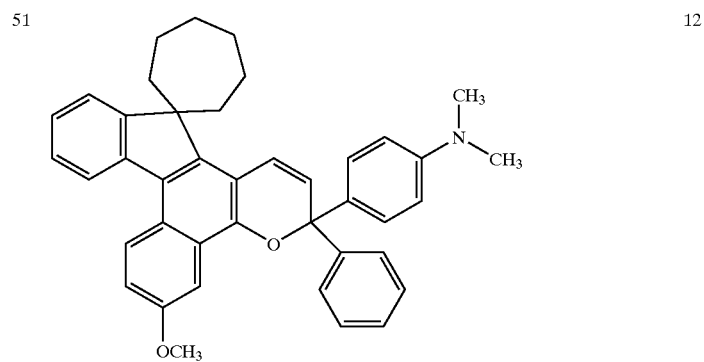 | 12 |

TABLE 13-continued

| No. | Structure | Value |
|---|---|---|
| 52 | (chemical structure) | 9 |
| 53 | (chemical structure) | 12 |

TABLE 14

| Ex. No. | Starting material | |
|---|---|---|
| | Benzofluorene derivative | Propargyl alcohol derivative |
| 54 | (chemical structure) | (chemical structure) |
| 55 | (chemical structure) | (chemical structure) |

TABLE 14-continued
| 56 | 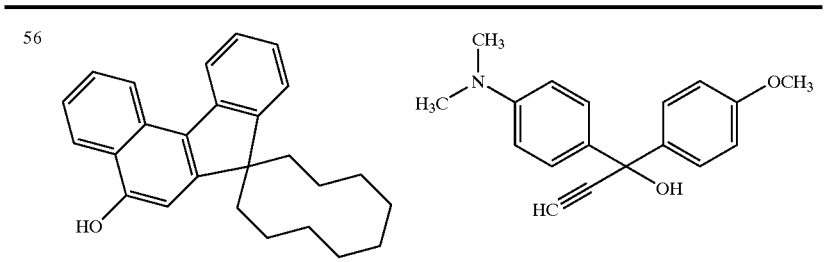 |
| --- | --- |
| 57 | 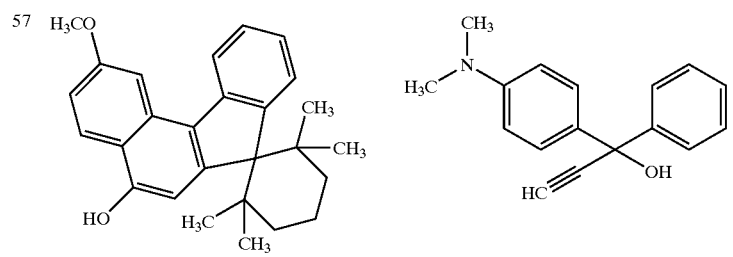 |
| Ex. No. | product | Yield (%) |
| --- | --- | --- |
| 54 | 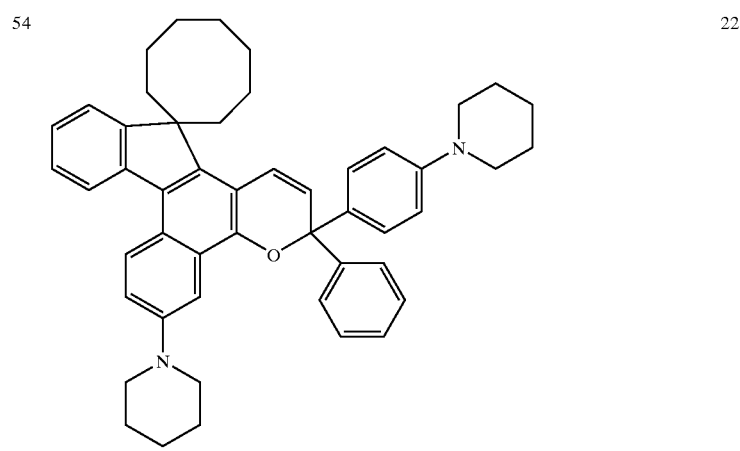 | 22 |
| 55 | 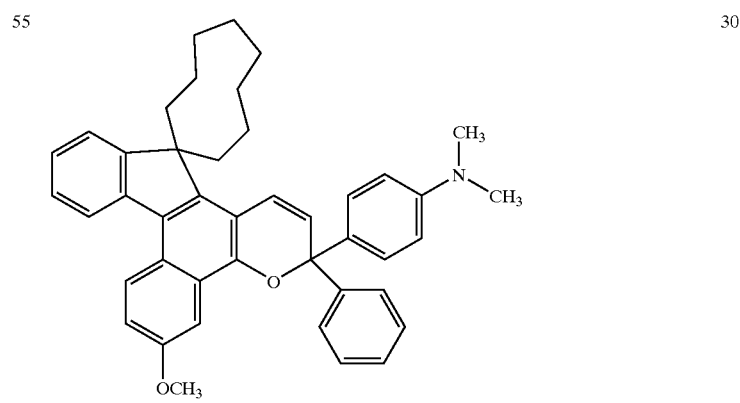 | 30 |

TABLE 14-continued
| | | |
|---|---|---|
| 56 | 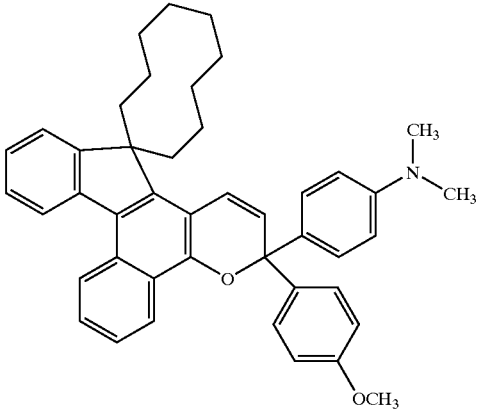 | 8 |
| 57 | 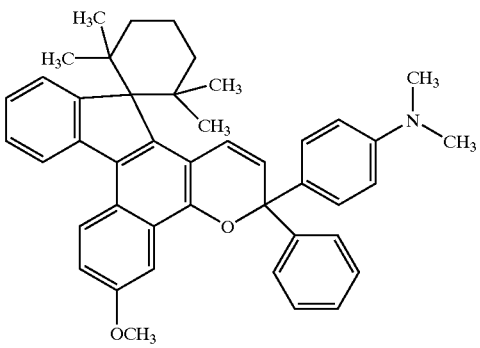 | 7 |
TABLE 15
| Ex. No. | Starting material | |
|---|---|---|
| | Benzofluorene derivative | Propargyl alcohol derivative |
| 58 | 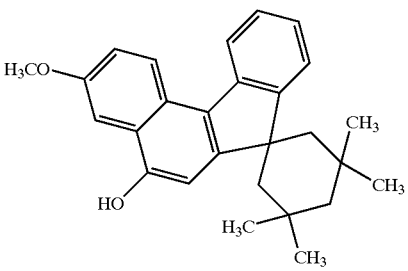 | 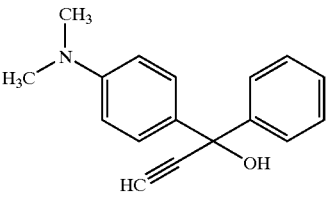 |
| 59 | 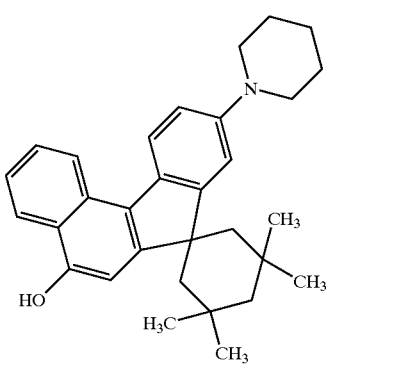 | 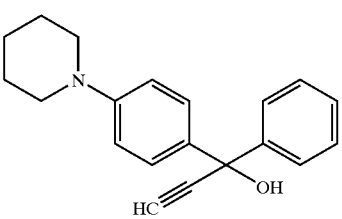 |

TABLE 15-continued
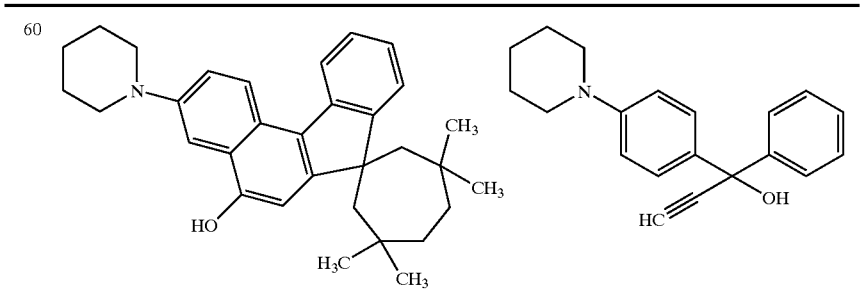
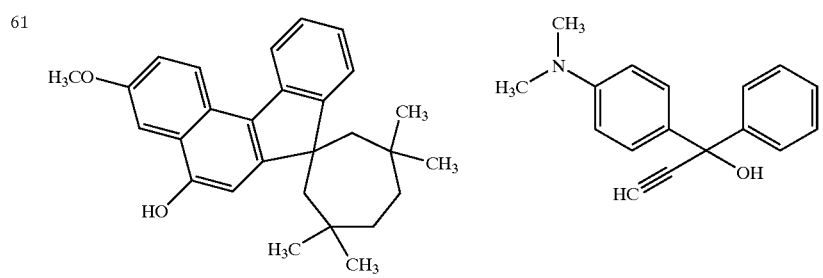
| Ex. No. | product | Yield (%) |
|---|---|---|
| 58 | 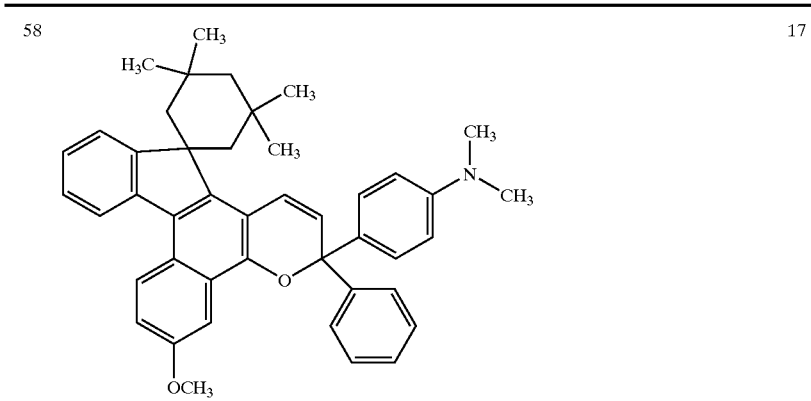 | 17 |
| 59 | 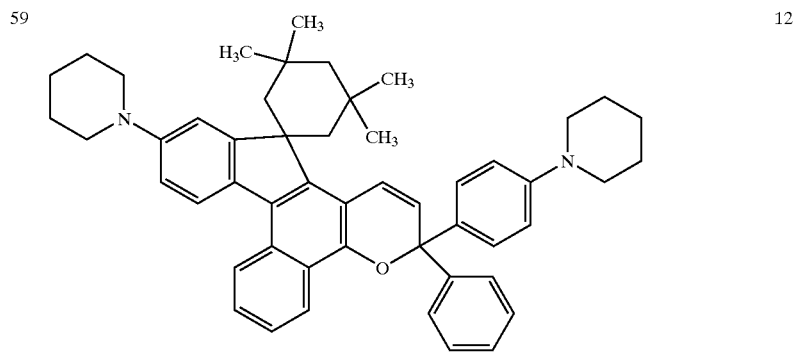 | 12 |

TABLE 15-continued

| Ex. No. | Structure | |
|---|---|---|
| 60 | [structure] | 16 |
| 61 | [structure] | 9 |

TABLE 16

| Ex. No. | Starting material | |
|---|---|---|
| | Benzofluorene derivative | Propargyl alcohol derivative |
| 62 | [structure] | [structure] |
| 63 | [structure] | [structure] |

TABLE 16-continued
| | | |
|---|---|---|
| 64 | 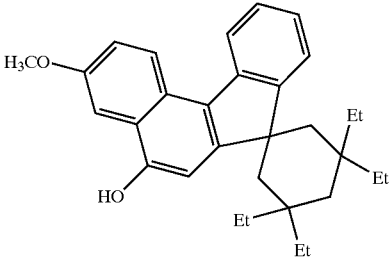 | 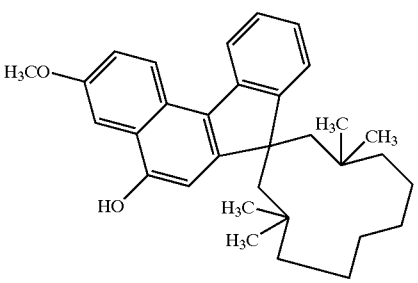 |
| 65 | 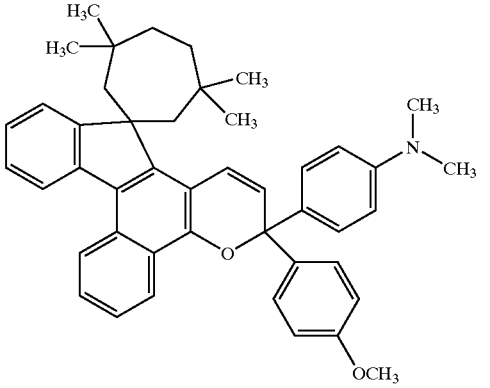 | 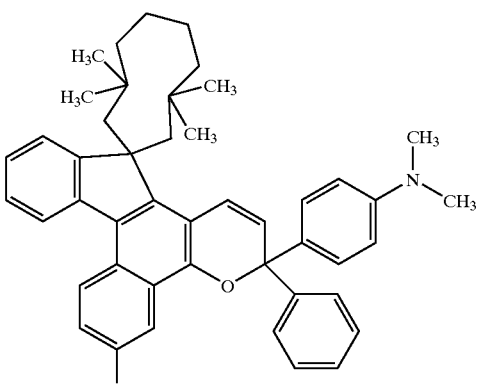 |
| Ex. No. | product | Yield (%) |
|---|---|---|
| 62 | | 25 |
| 63 | | 14 |

TABLE 16-continued

| 64 | [structure] | 9 |
| 65 | [structure] | 15 |
| | | 35 |

TABLE 17

| Ex. No. | Starting material | |
|---|---|---|
| | Benzofluorene derivative | Propargyl alcohol derivative |
| 66 | [structure] | [structure] |
| 67 | [structure] | [structure] |

TABLE 17-continued
68 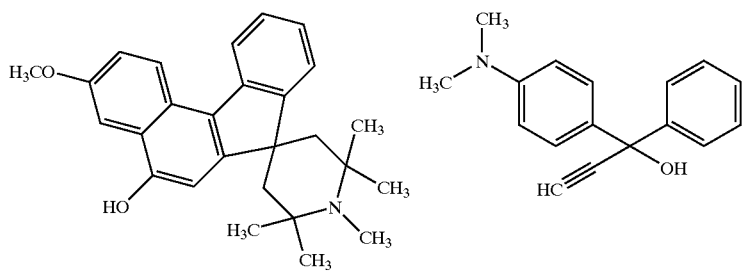
69 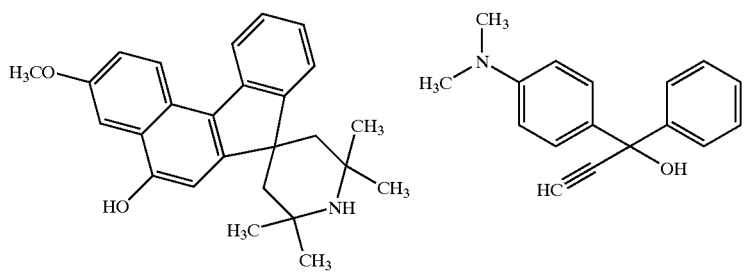
| Ex. No. | product | Yield (%) |
|---|---|---|
| 66 | 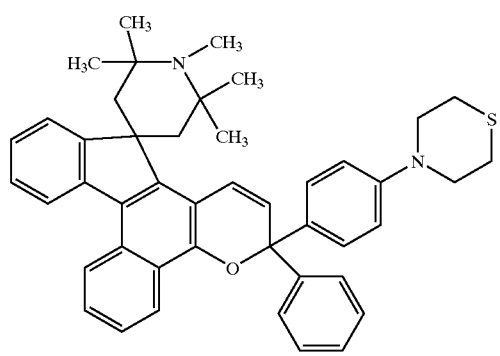 | 20 |
| 67 | 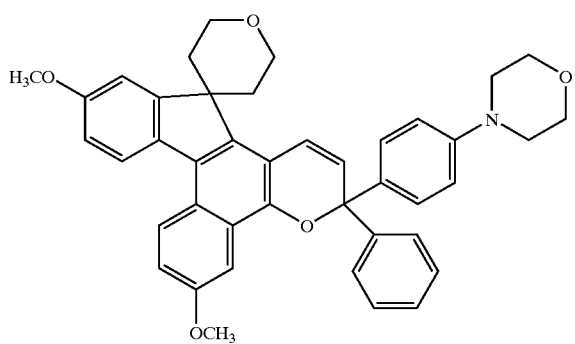 | 22 |

TABLE 17-continued
| | | |
|---|---|---|
| 68 | 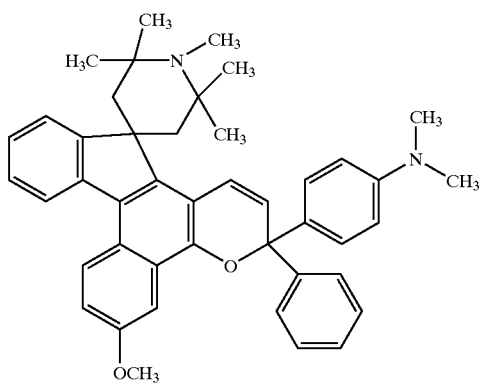 | 7 |
| 69 | 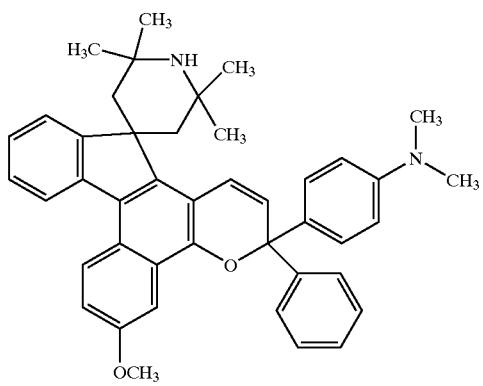 | 2 |
TABLE 18
| Ex. No. | Starting material | |
|---|---|---|
| | Benzofluorene derivative | Propargyl alcohol derivative |
| 70 | 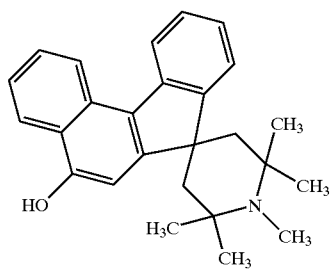 | 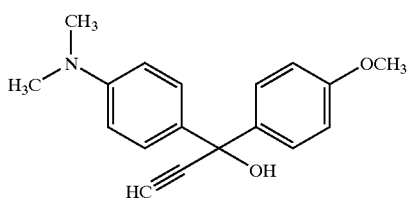 |
| 71 | 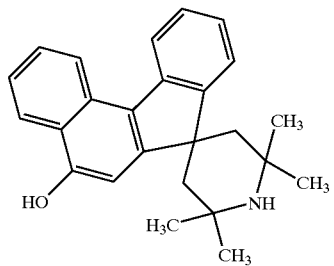 | 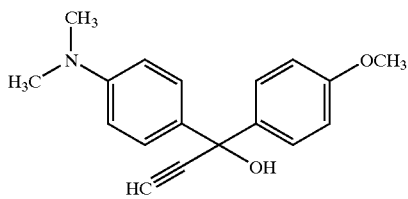 |

TABLE 18-continued
| 72 | 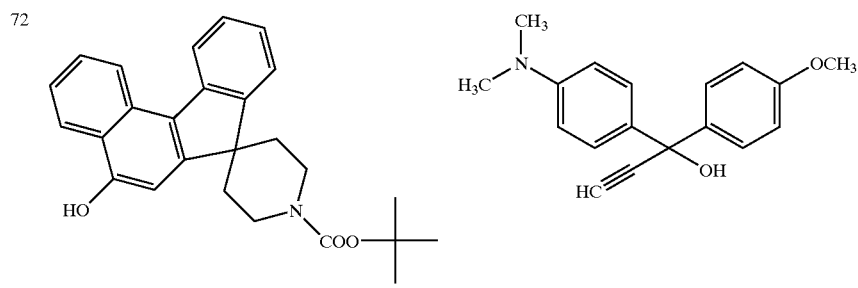 |
| 73 | 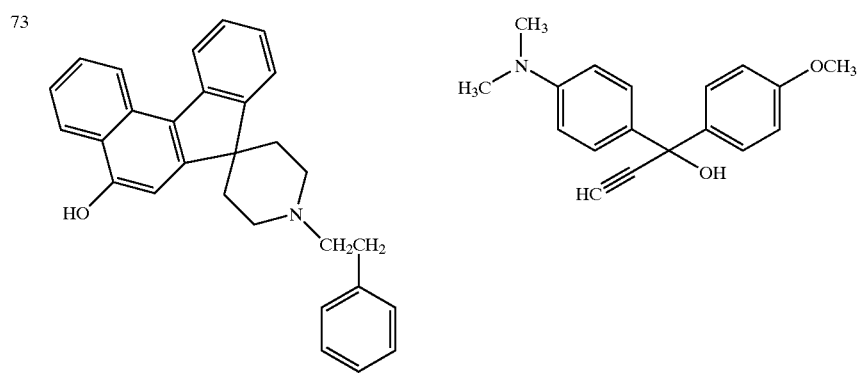 |
| Ex. No. | product | Yield (%) |
| --- | --- | --- |
| 70 | 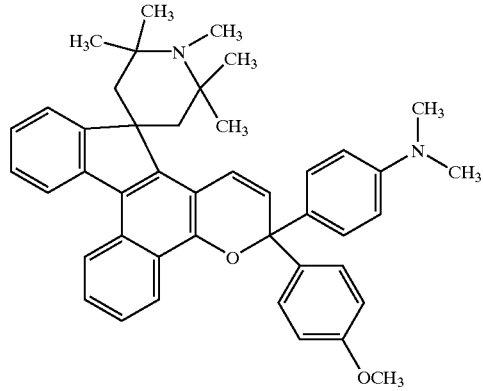 | 15 |
| 71 | 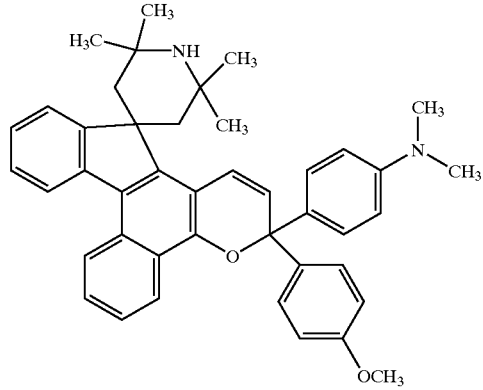 | 12 |

TABLE 18-continued

| 72 | [structure: spirofluorene-piperidine with N-COO-tBu, fused to naphthopyran bearing 4-(dimethylamino)phenyl and 4-methoxyphenyl substituents] | 7 |
| 73 | [structure: spirofluorene-piperidine with N-CH₂CH₂-phenyl, fused to naphthopyran bearing 4-(dimethylamino)phenyl and 4-methoxyphenyl substituents] | 13 |

TABLE 19

| Ex. No. | Starting material | |
|---|---|---|
| | Benzofluorene derivative | Propargyl alcohol derivative |
| 74 | [structure: hydroxy-benzofluorene spiro-piperidine with N-phenyl] | [structure: 1-(4-dimethylaminophenyl)-1-(4-methoxyphenyl)-2-propyn-1-ol] |
| 75 | [structure: hydroxy-benzofluorene spiro-piperidine with N-COOH] | [structure: 1-(4-dimethylaminophenyl)-1-(4-methoxyphenyl)-2-propyn-1-ol] |

TABLE 19-continued
| 76 | 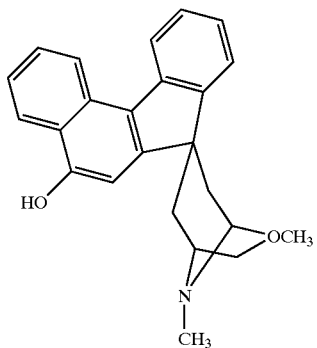 | 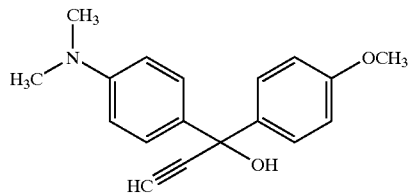 |
| 77 | 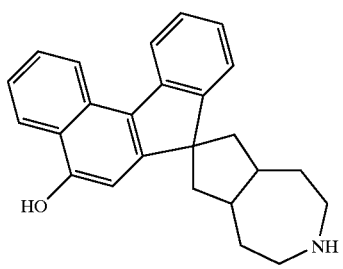 | 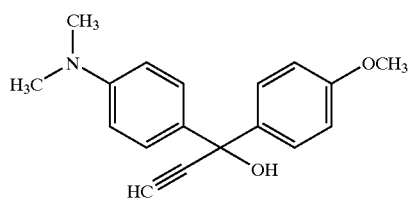 |
| Ex. No. | product | Yield (%) |
|---|---|---|
| 74 | 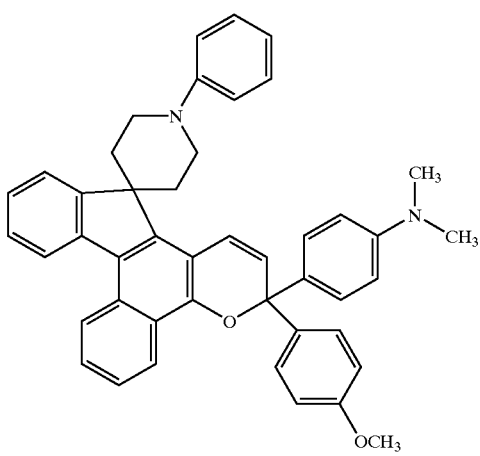 | 20 |
| 75 | 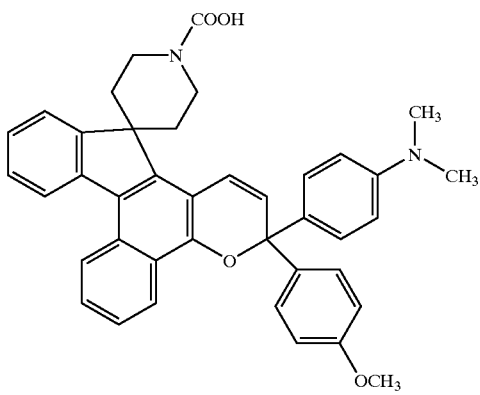 | 14 |

TABLE 19-continued
| 76 | 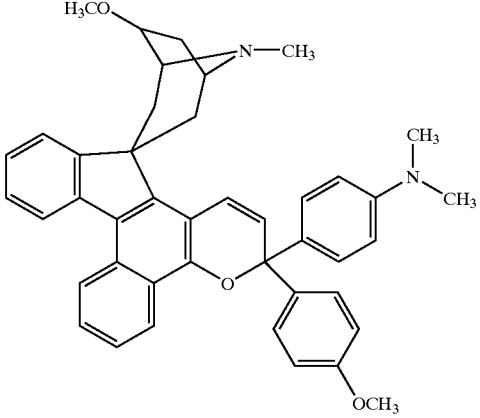 | 11 |
| --- | --- | --- |
| 77 | 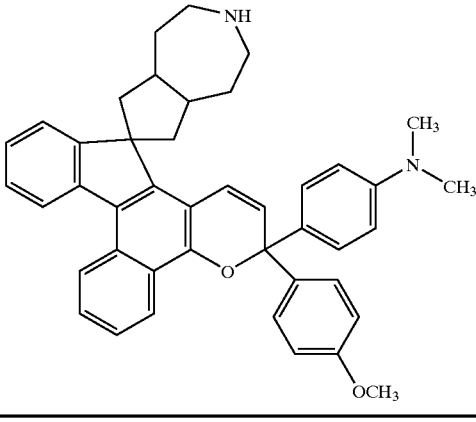 | 14 |
TABLE 20
| Ex. | Starting material | |
| --- | --- | --- |
| No. | Benzofluorene derivative | Propargyl alcohol derivative |
| 78 | 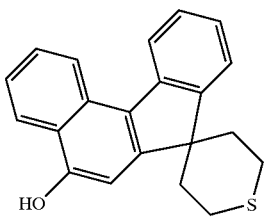 | 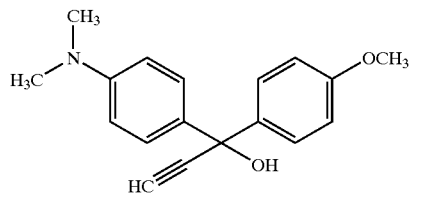 |
| 79 | 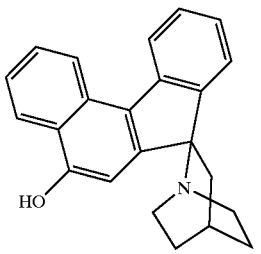 | 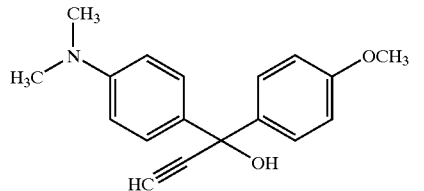 |

TABLE 20-continued
| 80 | 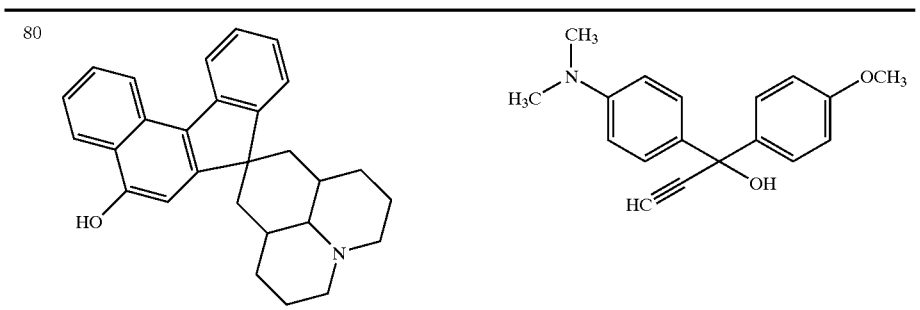 |
| 81 | 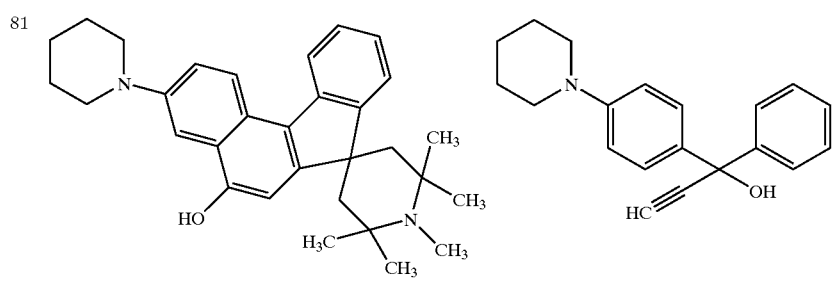 |
| Ex. No. | product | Yield (%) |
|---|---|---|
| 78 | 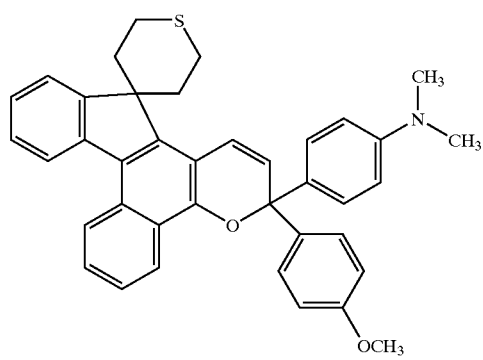 | 25 |
| 79 | 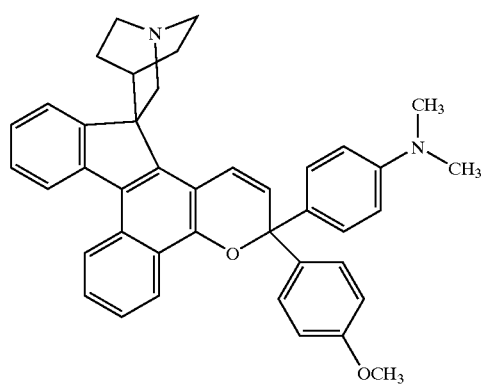 | 10 |

TABLE 20-continued
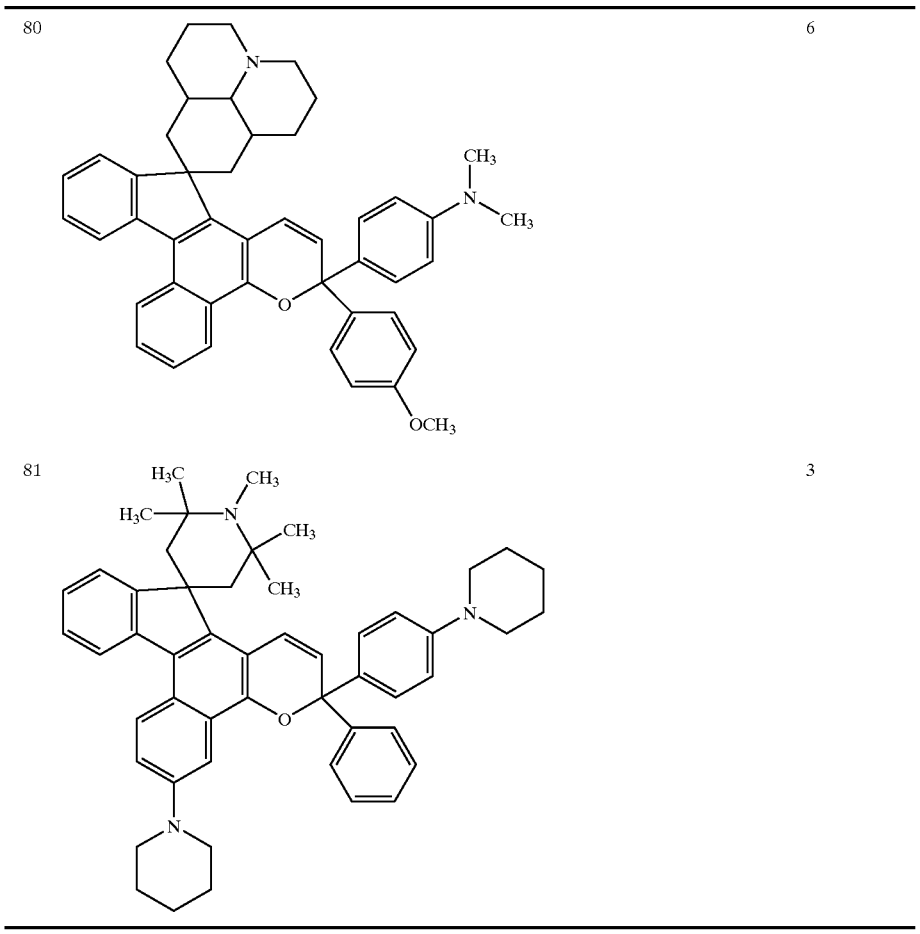
TABLE 21
| Ex. No. | Starting material | | product | Yield (%) |
|---|---|---|---|---|
| | Benzofluorene derivative | Propargyl alcohol derivative | | |
| 82 | | | | 19 |

TABLE 21-continued

| Ex. No. | Starting material | | product | Yield (%) |
|---|---|---|---|---|
| | Benzofluorene derivative | Propargyl alcohol derivative | | |
| 83 | | | | 17 |
| 84 | | | | 22 |

TABLE 22

| Ex. No. | Elemental analysis | | | | | | | | | | 1H-NMR (ppm) |
|---|---|---|---|---|---|---|---|---|---|---|---|
| | Found | | | | | Calculated | | | | | |
| | C | H | N | O | Others | C | H | N | O | Others | |
| 2 | 81.61 | 6.39 | 2.15 | 9.85 | | 81.58 | 6.38 | 2.16 | 9.88 | | δ5.6~9.0:17H<br>δ1.5~4.5:24H |
| 3 | 85.83 | 7.22 | 2.11 | 4.84 | | 85.81 | 7.20 | 2.13 | 4.86 | | δ5.6~9.0:17H<br>δ1.5~4.5:30H |
| 4 | 88.31 | 6.95 | 2.22 | 2.53 | | 88.28 | 6.93 | 2.24 | 2.56 | | δ5.6~9.0:19H<br>δ1.5~4.5:24H |
| 5 | 81.78 | 6.72 | 2.06 | 9.44 | | 81.75 | 6.71 | 2.07 | 9.47 | | δ5.6~9.0:17H<br>δ1.5~4.5:28H |
| 6 | 83.62 | 6.38 | 2.25 | 7.75 | | 83.60 | 6.36 | 2.27 | 7.77 | | δ5.6~9.0:18H<br>δ1.5~4.5:21H |
| 7 | 83.20 | 6.73 | 2.37 | 2.70 | | 88.17 | 6.71 | 2.39 | 2.73 | | δ5.6~9.0:19H<br>δ1.5~4.5:24H |
| 8 | 88.15 | 6.91 | 2.32 | 2.65 | | 88.11 | 6.89 | 2.34 | 2.67 | | δ5.6~9.0:19H<br>δ1.5~4.5:22H |
| 9 | 89.24 | 6.28 | 2.11 | 2.39 | | 89.19 | 6.26 | 2.12 | 2.42 | | δ5.6~9.0:23H<br>δ1.5~4.5:18H |
| 10 | 85.04 | 5.81 | | 3.04 | S6.11 | 85.02 | 5.79 | | 3.06 | S6.13 | δ5.6~9.0:18H<br>δ1.5~4.5:12H |
| 11 | 85.57 | 7.20 | 2.20 | 5.03 | | 85.54 | 7.18 | 2.22 | 5.06 | | δ5.6~9.0:19H<br>δ1.5~4.5:26H |
| 12 | 81.79 | 6.28 | 2.05 | 7.08 | F2.83 | 81.75 | 6.26 | 2.07 | 7.10 | F3.81 | δ5.6~9.0:17H<br>δ1.5~4.5:29H |
| 13 | 81.22 | 6.52 | | 12.25 | | 81.20 | 6.50 | | 12.29 | | δ5.6~9.0:16H<br>δ1.5~4.5:26H |
| 14 | 82.28 | 6.92 | 3.98 | 6.82 | | 82.25 | 6.90 | 4.00 | 6.85 | | δ5.6~9.0:18H<br>δ1.5~4.5:30H |
| 15 | 85.50 | 6.49 | 5.05 | 2.85 | | 85.37 | 6.61 | 5.11 | 2.92 | | δ5.6~9.0:17H<br>δ1.5~4.5:19H |

TABLE 23

| Ex. No. | Found C | H | N | O | Others | Calculated C | H | N | O | Others | 1H-NMR (ppm) |
|---|---|---|---|---|---|---|---|---|---|---|---|
| 16 | 82.14 | 6.60 | 4.15 | 7.10 | | 82.11 | 6.59 | 4.16 | 7.13 | | δ5.6~9.0:18H<br>δ1.5~4.5:26H |
| 17 | 85.26 | 7.00 | 2.35 | 5.39 | | 85.24 | 6.98 | 2.37 | 5.41 | | δ5.6~9.0:18H<br>δ1.5~4.5:23H |
| 18 | 83.30 | 6.51 | 2.29 | 7.89 | | 83.27 | 6.49 | 2.31 | 7.92 | | δ5.6~9.0:17H<br>δ1.5~4.5:22H |
| 19 | 80.00 | 6.72 | 1.97 | 11.30 | | 79.97 | 6.71 | 1.98 | 11.33 | | δ5.6~9.0:15H<br>δ1.5~4.5:32H |
| 20 | 83.29 | 6.51 | 2.29 | 7.90 | | 83.27 | 6.49 | 2.31 | 7.92 | | δ5.6~9.0:17H<br>δ1.5~4.5:22H |
| 21 | 83.30 | 6.51 | 2.29 | 7.89 | | 83.27 | 6.49 | 2.31 | 7.92 | | δ5.6~9.0:17H<br>δ1.5~4.5:22H |
| 22 | 83.73 | 6.73 | 2.15 | 7.41 | | 83.69 | 6.71 | 2.17 | 7.43 | | δ5.6~9.0:17H<br>δ1.5~4.5:26H |
| 23 | 83.74 | 6.73 | 2.16 | 7.40 | | 83.69 | 6.71 | 2.17 | 7.43 | | δ5.6~9.0:18H<br>δ1.5~4.5:25H |
| 24 | 85.27 | 7.17 | 2.30 | 5.26 | | 85.25 | 7.15 | 2.31 | 5.28 | | δ5.6~9.0:18H<br>δ1.5~4.5:12H |
| 25 | 78.45 | 6.32 | 1.93 | 13.31 | | 78.42 | 6.30 | 1.95 | 13.34 | | δ5.6~9.0:16H<br>δ1.5~4.5:29H |
| 26 | 85.99 | 7.07 | 4.43 | 2.52 | | 85.95 | 7.05 | 4.45 | 2.54 | | δ5.6~9.0:18H<br>δ1.5~4.5:26H |
| 27 | 79.06 | 5.92 | 2.03 | 4.64 | F8.35 | 79.04 | 5.90 | 2.05 | 4.68 | F8.34 | δ5.6~9.0:17H<br>δ1.5~4.5:23H |
| 28 | 83.53 | 6.00 | 2.36 | 8.11 | | 83.50 | 5.98 | 2.38 | 8.14 | | δ5.6~9.0:18H<br>δ1.5~4.5:27H |
| 29 | 82.70 | 7.09 | 3.76 | 6.45 | | 82.67 | 7.07 | 3.78 | 6.48 | | δ5.6~9.0:17H<br>δ1.5~4.5:35H |

TABLE 24

| Ex. No. | Found C | H | N | O | Others | Calculated C | H | N | O | Others | 1H-NMR (ppm) |
|---|---|---|---|---|---|---|---|---|---|---|---|
| 30 | 84.23 | 7.22 | 4.00 | 4.55 | | 84.20 | 7.21 | 4.01 | 4.58 | | δ5.6~9.0:17H<br>δ1.5~4.5:33H |
| 31 | 86.21 | 7.25 | 4.17 | 2.37 | | 86.19 | 7.23 | 4.19 | 2.39 | | δ5.6~9.0:18H<br>δ1.5~4.5:30H |
| 32 | 86.22 | 7.25 | 4.17 | 2.36 | | 86.19 | 7.23 | 4.19 | 2.39 | | δ5.6~9.0:18H<br>δ1.5~4.5:30H |
| 33 | 84.26 | 7.36 | 3.92 | 4.46 | | 84.23 | 7.35 | 3.93 | 4.49 | | δ5.6~9.0:17H<br>δ1.5~4.5:35H |
| 34 | 84.83 | 6.85 | 6.04 | 2.29 | | 84.81 | 6.83 | 6.06 | 2.31 | | δ5.6~9.0:17H<br>δ1.5~4.5:30H |
| 35 | 86.22 | 7.25 | 4.17 | 2.36 | | 86.19 | 7.23 | 4.19 | 2.39 | | δ5.6~9.0:18H<br>δ1.5~4.5:30H |
| 36 | 88.82 | 6.52 | 2.18 | 2.50 | | 88.78 | 6.50 | 2.20 | 2.52 | | δ5.6~9.0:21H<br>δ1.5~4.5:20H |
| 37 | 86.53 | 6.65 | 4.38 | 2.47 | | 86.48 | 6.63 | 4.39 | 2.50 | | δ5.6~9.0:19H<br>δ1.5~4.5:23H |
| 38 | 84.23 | 6.14 | 2.17 | 2.47 | S5.01 | 84.21 | 6.12 | 2.18 | 2.49 | S5.00 | δ5.6~9.0:19H<br>δ1.5~4.5:20H |
| 39 | 86.40 | 6.30 | 2.22 | 5.08 | | 86.37 | 6.28 | 2.24 | 5.11 | | δ5.6~9.0:19H<br>δ1.5~4.5:20H |
| 40 | 88.92 | 6.58 | 2.22 | 2.46 | | 88.78 | 6.50 | 2.20 | 2.52 | | δ5.6~9.0:21H<br>δ1.5~4.5:20H |
| 41 | 85.27 | 7.17 | 2.22 | 5.24 | | 85.25 | 7.15 | 2.31 | 5.28 | | δ5.6~9.0:18H<br>δ1.5~4.5:25H |
| 42 | 85.29 | 7.34 | 2.24 | 5.13 | | 85.26 | 7.32 | 2.26 | 5.16 | | δ5.6~9.0:18H<br>δ1.5~4.5:27H |
| 43 | 85.31 | 7.64 | 2.14 | 4.91 | | 85.28 | 7.62 | 2.16 | 4.94 | | δ5.6~9.0:18H<br>δ1.5~4.5:31H |

TABLE 25

| Ex. No. | Found C | H | N | O | Others | Calculated C | H | N | O | Others | 1H-NMR (ppm) |
|---|---|---|---|---|---|---|---|---|---|---|---|
| 44 | 85.28 | 7.16 | 2.30 | 5.25 | | 85.25 | 7.15 | 2.31 | 5.58 | | δ5.6~9.0:18H<br>δ1.5~4.5:25H |
| 45 | 85.28 | 7.34 | 2.24 | 5.14 | | 85.26 | 7.32 | 2.26 | 5.16 | | δ5.6~9.0:18H<br>δ1.5~4.5:27H |
| 46 | 85.57 | 7.04 | 2.25 | 5.15 | | 85.54 | 7.02 | 2.27 | 5.18 | | δ5.6~9.0:18H<br>δ1.5~4.5:25H |
| 47 | 85.84 | 7.21 | 2.12 | 4.83 | | 85.81 | 7.20 | 2.13 | 4.86 | | δ5.6~9.0:18H<br>δ1.5~4.5:29H |
| 48 | 85.83 | 7.22 | 2.11 | 4.84 | | 85.81 | 7.20 | 2.13 | 4.86 | | δ5.6~9.0:18H<br>δ1.5~4.5:29H |
| 49 | 85.83 | 7.37 | 2.06 | 4.73 | | 85.80 | 7.35 | 2.08 | 4.76 | | δ5.6~9.0:18H<br>δ1.5~4.5:31H |
| 50 | 85.31 | 7.49 | 2.19 | 5.03 | | 85.27 | 7.47 | 2.21 | 5.05 | | δ5.6~9.0:18H<br>δ1.5~4.5:29H |
| 51 | 85.28 | 6.82 | 2.41 | 5.51 | | 85.23 | 6.80 | 2.42 | 5.54 | | δ5.6~9.0:18H<br>δ1.5~4.5:21H |
| 52 | 85.26 | 7.00 | 2.36 | 5.39 | | 85.24 | 6.98 | 2.37 | 5.41 | | δ5.6~9.0:18H<br>δ1.5~4.5:23H |
| 53 | 85.32 | 6.87 | 2.39 | 5.53 | | 85.24 | 6.98 | 2.37 | 5.41 | | δ5.6~9.0:18H<br>δ1.5~4.5:23H |
| 54 | 85.96 | 7.67 | 4.07 | 2.32 | | 85.92 | 7.65 | 4.09 | 2.34 | | δ5.6~9.0:18H<br>δ1.5~4.5:34H |
| 55 | 85.27 | 7.17 | 2.29 | 5.24 | | 85.25 | 7.15 | 2.31 | 5.28 | | δ5.6~9.0:18H<br>δ1.5~4.5:25H |
| 56 | 85.29 | 7.34 | 2.24 | 5.13 | | 85.26 | 7.32 | 2.26 | 5.16 | | δ5.6~9.0:18H<br>δ1.5~4.5:27H |
| 57 | 85.09 | 7.23 | 2.21 | 5.07 | | 85.26 | 7.32 | 2.26 | 5.16 | | δ5.6~9.0:18H<br>δ1.5~4.5:27H |

TABLE 26

| Ex. No. | Found C | H | N | O | Others | Calculated C | H | N | O | Others | 1H-NMR (ppm) |
|---|---|---|---|---|---|---|---|---|---|---|---|
| 58 | 85.29 | 7.33 | 2.25 | 5.13 | | 85.26 | 7.32 | 2.26 | 5.16 | | δ5.6~9.0:18H<br>δ1.5~4.5:27H |
| 59 | 85.93 | 7.94 | 3.91 | 2.22 | | 85.91 | 7.92 | 3.93 | 2.24 | | δ5.6~9.0:18H<br>δ1.5~4.5:38H |
| 60 | 85.94 | 8.06 | 3.83 | 2.17 | | 85.91 | 8.04 | 3.85 | 2.20 | | δ5.6~9.0:18H<br>δ1.5~4.5:40H |
| 61 | 85.30 | 7.48 | 2.20 | 5.02 | | 85.27 | 7.47 | 2.21 | 5.05 | | δ5.6~9.0:18H<br>δ1.5~4.5:29H |
| 62 | 85.29 | 7.49 | 2.19 | 5.03 | | 85.27 | 7.47 | 2.21 | 5.05 | | δ5.6~9.0:18H<br>δ1.5~4.5:29H |
| 63 | 84.95 | 8.13 | 2.14 | 4.72 | | 85.04 | 8.18 | 2.07 | 4.72 | | δ5.6~9.0:18H<br>δ1.5~4.5:33H |
| 64 | 85.33 | 7.92 | 2.05 | 4.71 | | 85.29 | 7.90 | 2.07 | 4.73 | | δ5.6~9.0:18H<br>δ1.5~4.5:35H |
| 65 | 85.35 | 8.05 | 2.02 | 4.61 | | 85.30 | 8.03 | 2.03 | 4.64 | | δ5.6~9.0:18H<br>δ1.5~4.5:37H |
| 66 | 81.54 | 6.99 | 4.21 | 2.36 | S4.90 | 81.53 | 6.99 | 4.23 | 2.41 | S4.84 | δ5.6~9.0:23H<br>δ1.5~4.5:23H |
| 67 | 79.13 | 6.18 | 2.18 | 12.51 | | 79.10 | 6.16 | 2.20 | 12.54 | | δ5.6~9.0:15H<br>δ1.5~4.5:22H |
| 68 | 83.28 | 7.32 | 4.39 | 5.02 | | 83.24 | 7.30 | 4.41 | 5.04 | | δ5.6~9.0:18H<br>δ1.5~4.5:28H |
| 69 | 83.21 | 7.16 | 4.49 | 5.11 | | 83.19 | 7.14 | 4.51 | 5.15 | | δ5.6~9.0:18H<br>δ1.5~4.5:26H |
| 70 | 83.27 | 7.32 | 4.39 | 5.01 | | 83.24 | 7.30 | 4.41 | 5.04 | | δ5.6~9.0:18H<br>δ1.5~4.5:28H |
| 71 | 83.22 | 7.16 | 4.49 | 5.12 | | 83.19 | 7.14 | 4.51 | 5.15 | | δ5.6~9.0:18H<br>δ1.5~4.5:26H |

TABLE 27

| Ex. No. | Found | | | | | Calculated | | | | | 1H-NMR (ppm) |
|---|---|---|---|---|---|---|---|---|---|---|---|
| | C | H | N | O | Others | C | H | N | O | Others | |
| 72 | 79.52 | 6.68 | 4.20 | 9.60 | | 79.49 | 6.67 | 4.21 | 9.63 | | δ5.6~9.0:18H<br>δ1.5~4.5:26H |
| 73 | 84.42 | 6.65 | 4.17 | 4.76 | | 84.40 | 6.63 | 4.19 | 4.78 | | δ5.6~9.0:18H<br>δ1.5~4.5:26H |
| 74 | 84.37 | 6.31 | 4.35 | 4.96 | | 84.34 | 6.29 | 4.37 | 4.99 | | δ5.6~9.0:23H<br>δ1.5~4.5:17H |
| 75 | 78.95 | 5.97 | 4.59 | 10.48 | | 78.92 | 5.96 | 4.60 | 10.51 | | δ5.6~9.0:18H<br>δ1.5~4.5:18H |
| 76 | 81.22 | 7.14 | 4.28 | 7.35 | | 81.20 | 7.12 | 4.30 | 7.37 | | δ5.6~9.0:18H<br>δ1.5~4.5:28H |
| 77 | 83.49 | 6.86 | 4.51 | 5.14 | | 83.46 | 6.84 | 4.53 | 5.17 | | δ5.6~9.0:18H<br>δ1.5~4.5:24H |
| 78 | 80.56 | 6.08 | 2.39 | 5.48 | S5.52 | 80.52 | 6.06 | 2.41 | 5.50 | S5.51 | δ5.6~9.0:18H<br>δ1.5~4.5:17H |
| 79 | 83.18 | 7.00 | 4.61 | 5.24 | | 83.13 | 6.98 | 4.62 | 5.27 | | δ5.6~9.0:18H<br>δ1.5~4.5:24H |
| 80 | 83.87 | 7.06 | 4.24 | 4.84 | | 83.85 | 7.04 | 4.25 | 4.86 | | δ5.6~9.0:18H<br>δ1.5~4.5:28H |
| 81 | 84.17 | 7.91 | 5.75 | 2.17 | | 84.14 | 7.89 | 5.77 | 2.20 | | δ5.6~9.0:18H<br>δ1.5~4.5:39H |
| 82 | 85.82 | 8.31 | 3.76 | 2.14 | | 85.78 | 8.29 | 3.78 | 2.16 | | δ5.6~9.0:18H<br>δ1.5~4.5:43H |
| 83 | 87.74 | 8.09 | 2.03 | 2.21 | | 87.72 | 8.07 | 1.97 | 2.25 | | δ5.6~9.0:17H<br>δ1.5~4.5:40H |
| 84 | 87.32 | 8.37 | 2.02 | 2.30 | | 87.29 | 8.35 | 2.04 | 2.33 | | δ5.6~9.0:18H<br>δ1.5~4.5:37H |

Example 85

0.05 Parts by weight of the chromene compound obtained in Example 1 were added to 10 parts by weight of a tetraethylene glycol dimethacrylate, 50 parts by weight of a 2,2-bis[4-(methacryloxyethoxy)phenyl]propane, 10 parts by weight of a methyl ether nonaethylene glycol methacrylate, 20 parts by weight of a trimethylolpropane trimethacrylate and 10 parts by weight of a glycidyl methacrylate. Then, 1 part by weight of a t-butylperoxy-2-ethyl hexanate was added thereto as a polymerization initiator, and the mixture was mixed together to a sufficient degree. The mixture solution was poured into a mold constituted by glass plates and gaskets of an ethylene/vinyl acetate copolymer, and was cast-polymerized. The polymerization was conducted by using an air furnace, gradually elevating the temperature from 30° C. to 90° C. over 18 hours and maintaining the temperature of 90° C. for 2 hours. After the polymerization, the polymer was removed from the glass mold.

The obtained polymer (2 mm thick) was irradiated with light by using a xenon lamp L-2480 (300W) SHL-100 manufactured by Hamamatsu Photonics Co. through an aeromass filter (manufactured by Coning Co.) at 20±1° C. at beam intensities on the polymer surface of 365 nm=2.4 mW/cm$^2$ and 245 nm=24 μW/cm$^2$ for 120 seconds to develop color and to measure the photochromic properties. The photochromic properties were evaluated in a manner as described below.

① Maximum absorption wavelength (λmax): A maximum absorption wavelength after the development of color as found by using a spectrophotometer (instantaneous multi-channel photodetector MCPD 1000) manufactured by Otsuka Denshi Co. The maximum absorption wavelength is related to the color tone at the time when the color is developed.

② Initial color {ϵ(0)}: Absorbency in a state of not being irradiated with light at the maximum absorption wavelength. In an optical material such as spectacle lenses, it can be said that the lower this value is, the more excellent the photochromic properties are.

③ Color density {ϵ(120)−ϵ(0)}: A difference between an absorbency {ϵ(120)} after irradiated with light for 120 seconds at the maximum absorption wavelength and the above absorbency ϵ(0). It can be said that the higher this value is, the more excellent the photochromic properties are.

④ Color-developing sensitivity (sec.): The time until the absorbency of the sample irradiated with light of the above maximum wavelength reaches the saturation. It can be said that the shorter the time is, the more excellent the color-developing sensitivity is.

⑤ Fading rate [$t_{1/2}$ (min)]: The time until the absorbency of a sample at the maximum wavelength drops down to one-half the {ϵ(120)−ϵ(0)} from when the sample is no longer irradiated with light after it was irradiated with light for 120 seconds. It can be said that the shorter the time is, the more excellent the photochromic properties are.

⑥ Remaining ratio (%)={($A_{200}/A_0$)×100}: The following deterioration promotion testing was conducted in order to evaluate the light resistance of color against the irradiation with light. That is, the obtained polymer (sample) was deteriorated for 200 hours by using a xenon weather meter X25 manufactured by Suga Shikenki Co. The densities of color were evaluated before and after the testing; i.e., the color density ($A_0$) was measured before the testing and the color density ($A_{200}$) was measured after the testing, and a value {($A_{200}/A_0$)×100} was regarded to be a remaining ratio (%) and was used as an index of light resistance of color. The higher the remaining ratio is, the higher the light resistance of color is.

⑦ Change in the coloring degree (ΔYI)=YI(200)−YI(0): In order to evaluate the light resistance of color tone of when not irradiated with light, the samples before and after the deterioration promotion testing were measured for their color difference by using a color-difference meter (SM-4) manufactured by Suga Shikenki Co. A change in the coloring degree (ΔYI) due to deterioration was found by subtracting a value {YI(0)} of coloring degree of before the testing from a value {YI(200)} of coloring degree of after the testing to evaluate the light resistance. The smaller the value ΔYI is, the higher the light resistance of color tone of when not irradiated with light is.

As a result, the curve of absorbency was bimodal having two absorption peaks, the wavelengths (λmax) of the peaks were 460 and 562 nm, and ΔYI was 1.5. At the wavelength of 460 nm, ε(0) was 0.03, ε(120)−ε(0) was 0.45, the color-developing sensitivity was 55 seconds, $\tau_{1/2}$ was 0.8 minutes, and the remaining ratio was 95%. Further, at the wavelength 562 nm, ε(0) was 0.03, ε(120) −ε(0) was 0.86, the color-developing sensitivity was 55 seconds, $\tau_{1/2}$ was 0.8 minutes, and the remaining ratio was 95%.

Further, the samples were held in a room maintained at 25° C. for one day and were measured for their L-scale Rockwell hardness to be 95 by using the Akashi Rockwell hardness tester (model, AR-10).

Examples 86 to 168

Photochromic polymers were obtained in the same manner as described in Example 85 but using, as chromene compounds, the compounds obtained in Examples 2 to 84, to evaluate their properties. The results were as shown in Tables 28 to 33.

TABLE 28

| Ex. No. | Compound No. | λ max (nm) | Initial color ε (0) | Color density ε (120) − ε (0) | Color-developing sensitivity (sec.) | Fading rate τ/1/2 (min.) | Light resistance ΔYI | Remaining ratio (%) |
|---|---|---|---|---|---|---|---|---|
| 85 | 1 | 460 | 0.03 | 0.45 | 55 | 0.8 | 1.5 | 95 |
|  |  | 562 | 0.03 | 0.86 | 55 | 0.8 |  | 95 |
| 86 | 2 | 470 | 0.03 | 0.50 | 60 | 1.0 | 1.5 | 95 |
|  |  | 572 | 0.03 | 0.92 | 60 | 1.0 |  | 95 |
| 87 | 3 | 468 | 0.04 | 0.46 | 60 | 1.0 | 2 | 94 |
|  |  | 560 | 0.04 | 0.80 | 60 | 1.0 |  | 94 |
| 88 | 4 | 470 | 0.04 | 0.42 | 65 | 0.9 | 2.6 | 94 |
|  |  | 570 | 0.04 | 0.76 | 65 | 0.9 |  | 94 |
| 89 | 5 | 472 | 0.04 | 0.40 | 55 | 0.8 | 2.5 | 93 |
|  |  | 576 | 0.04 | 0.86 | 55 | 0.8 |  | 93 |
| 90 | 6 | 464 | 0.03 | 0.47 | 60 | 0.8 | 2.0 | 94 |
|  |  | 570 | 0.03 | 0.89 | 60 | 0.8 |  | 94 |
| 91 | 7 | 474 | 0.04 | 0.41 | 60 | 0.8 | 2.0 | 93 |
|  |  | 586 | 0.03 | 0.74 | 60 | 0.8 |  | 93 |
| 92 | 8 | 476 | 0.05 | 0.42 | 60 | 0.9 | 3.0 | 92 |
|  |  | 574 | 0.03 | 0.86 | 60 | 0.9 |  | 92 |
| 93 | 9 | 468 | 0.03 | 0.40 | 60 | 1.0 | 2.0 | 91 |
|  |  | 572 | 0.03 | 0.88 | 60 | 1.0 |  | 91 |
| 94 | 10 | 470 | 0.04 | 0.48 | 50 | 0.8 | 3.0 | 92 |
|  |  | 576 | 0.04 | 0.90 | 50 | 0.8 |  | 92 |
| 95 | 11 | 460 | 0.04 | 0.40 | 65 | 0.9 | 3.0 | 92 |
|  |  | 564 | 0.04 | 0.82 | 65 | 0.9 |  | 92 |
| 96 | 12 | 466 | 0.04 | 0.46 | 60 | 0.8 | 2.0 | 94 |
|  |  | 572 | 0.04 | 0.92 | 60 | 0.8 |  | 94 |
| 97 | 13 | 456 | 0.04 | 0.48 | 60 | 1.0 | 2.0 | 93 |
|  |  | 558 | 0.04 | 0.89 | 60 | 1.0 |  | 93 |
| 98 | 14 | 466 | 0.04 | 0.42 | 60 | 1.0 | 2.0 | 94 |
|  |  | 568 | 0.04 | 0.88 | 60 | 1.0 |  | 94 |
| 99 | 15 | 440 | 0.03 | 0.48 | 55 | 1.0 | 2.9 | 90 |
|  |  | 600 | 0.03 | 0.89 | 55 | 1.0 |  | 90 |

TABLE 29

| Ex. No. | Compound No. | λ max (nm) | Initial color ε (0) | Color density ε (120) − ε (0) | Color-developing sensitivity (sec.) | Fading rate τ/1/2 (min.) | Light resistance ΔYI | Remaining ratio (%) |
|---|---|---|---|---|---|---|---|---|
| 100 | 16 | 490 | 0.03 | 0.58 | 60 | 1.1 | 2 | 95 |
|  |  | 610 | 0.03 | 1.10 | 60 | 1.1 |  | 95 |
| 101 | 17 | 470 | 0.03 | 0.55 | 60 | 0.6 | 2.2 | 94 |
|  |  | 606 | 0.03 | 1.20 | 60 | 0.6 |  | 94 |
| 102 | 18 | 472 | 0.03 | 0.46 | 60 | 0.6 | 2.3 | 95 |
|  |  | 615 | 0.03 | 1.05 | 60 | 0.6 |  | 95 |

TABLE 29-continued

| Ex. No. | Compound No. | λ max (nm) | Initial color $\epsilon(0)$ | Color density $\epsilon(120) - \epsilon(0)$ | Color-developing sensitivity (sec.) | Fading rate $\tau/1/2$ (min.) | Light resistance ΔYI | Light resistance Remaining ratio (%) |
|---|---|---|---|---|---|---|---|---|
| 103 | 19 | 500 | 0.04 | 0.44 | 65 | 1.3 | 1.9 | 95 |
|     |    | 630 | 0.04 | 0.98 | 65 | 1.3 |     | 95 |
| 104 | 20 | 472 | 0.03 | 0.38 | 60 | 0.6 | 2.2 | 95 |
|     |    | 606 | 0.03 | 0.86 | 60 | 0.6 |     | 95 |
| 105 | 21 | 476 | 0.03 | 0.44 | 60 | 0.5 | 1.9 | 95 |
|     |    | 610 | 0.03 | 0.87 | 60 | 0.5 |     | 95 |
| 106 | 22 | 474 | 0.03 | 0.44 | 70 | 0.8 | 2.1 | 94 |
|     |    | 590 | 0.03 | 0.89 | 70 | 0.8 |     | 94 |
| 107 | 23 | 476 | 0.03 | 0.42 | 65 | 0.7 | 2.9 | 93 |
|     |    | 590 | 0.03 | 0.88 | 65 | 0.7 |     | 93 |
| 108 | 24 | 474 | 0.03 | 0.40 | 60 | 0.5 | 2.2 | 96 |
|     |    | 608 | 0.03 | 0.88 | 60 | 0.5 |     | 96 |
| 109 | 25 | 470 | 0.04 | 0.66 | 60 | 0.8 | 3.0 | 90 |
|     |    | 588 | 0.04 | 0.97 | 60 | 0.8 |     | 90 |
| 110 | 26 | 470 | 0.04 | 0.64 | 65 | 0.9 | 3.0 | 90 |
|     |    | 620 | 0.04 | 0.89 | 65 | 0.9 |     | 90 |
| 111 | 27 | 466 | 0.02 | 0.46 | 60 | 1.2 | 2.0 | 94 |
|     |    | 588 | 0.02 | 0.97 | 60 | 1.2 |     | 94 |
| 112 | 28 | 460 | 0.04 | 0.48 | 60 | 0.8 | 2.2 | 90 |
|     |    | 578 | 0.04 | 0.83 | 60 | 0.8 |     | 90 |
| 113 | 29 | 470 | 0.03 | 0.68 | 65 | 1.3 | 2.4 | 90 |
|     |    | 616 | 0.03 | 0.89 | 65 | 1.3 |     | 90 |
| 114 | 30 | 468 | 0.04 | 0.64 | 60 | 1.5 | 2.5 | 90 |
|     |    | 616 | 0.04 | 0.92 | 60 | 1.5 |     | 90 |

TABLE 30

| Ex. No. | Compound No. | λ max (nm) | Initial color $\epsilon(0)$ | Color density $\epsilon(120) - \epsilon(0)$ | Color-developing sensitivity (sec.) | Fading rate $\tau/1/2$ (min.) | Light resistance ΔYI | Light resistance Remaining ratio (%) |
|---|---|---|---|---|---|---|---|---|
| 115 | 31 | 470 | 0.03 | 0.68 | 65 | 1.2 | 2.2 | 90 |
|     |    | 618 | 0.03 | 0.98 | 65 | 1.2 |     | 90 |
| 116 | 32 | 470 | 0.03 | 0.60 | 60 | 1.2 | 2.3 | 90 |
|     |    | 616 | 0.03 | 0.92 | 60 | 1.2 |     | 90 |
| 117 | 33 | 470 | 0.04 | 0.73 | 60 | 1.4 | 2.3 | 90 |
|     |    | 620 | 0.04 | 0.98 | 60 | 1.4 |     | 90 |
| 118 | 34 | 470 | 0.04 | 0.62 | 65 | 1.6 | 2.9 | 89 |
|     |    | 622 | 0.04 | 0.76 | 65 | 1.6 |     | 89 |
| 119 | 35 | 472 | 0.04 | 0.54 | 60 | 1.7 | 2.2 | 93 |
|     |    | 600 | 0.04 | 0.88 | 60 | 1.7 |     | 93 |
| 120 | 36 | 470 | 0.03 | 0.47 | 55 | 1.1 | 2.0 | 90 |
|     |    | 618 | 0.03 | 1.00 | 55 | 1.1 |     | 90 |
| 121 | 37 | 470 | 0.03 | 0.46 | 50 | 1.1 | 3.0 | 89 |
|     |    | 606 | 0.03 | 0.88 | 50 | 1.2 |     | 89 |
| 122 | 38 | 476 | 0.03 | 0.47 | 50 | 1.1 | 2.8 | 90 |
|     |    | 600 | 0.03 | 0.88 | 50 | 1.2 |     | 90 |
| 123 | 39 | 470 | 0.03 | 0.42 | 50 | 1.3 | 3.0 | 90 |
|     |    | 596 | 0.03 | 0.85 | 50 | 1.3 |     | 90 |
| 124 | 40 | 470 | 0.04 | 0.48 | 50 | 1.7 | 2.0 | 90 |
|     |    | 618 | 0.04 | 1.01 | 50 | 1.7 |     | 90 |
| 125 | 41 | 470 | 0.03 | 0.55 | 65 | 0.5 | 3.0 | 92 |
|     |    | 606 | 0.03 | 1.20 | 65 | 0.5 |     | 92 |
| 126 | 42 | 466 | 0.03 | 0.56 | 65 | 0.6 | 3.0 | 90 |
|     |    | 606 | 0.03 | 1.14 | 65 | 0.6 |     | 90 |
| 127 | 43 | 470 | 0.04 | 0.54 | 60 | 0.6 | 2.0 | 93 |
|     |    | 606 | 0.04 | 1.17 | 60 | 0.6 |     | 93 |
| 128 | 44 | 470 | 0.04 | 0.44 | 60 | 0.6 | 2.2 | 94 |
|     |    | 606 | 0.04 | 1.05 | 60 | 0.6 |     | 94 |
| 129 | 45 | 470 | 0.04 | 0.46 | 60 | 0.5 | 2.5 | 94 |
|     |    | 606 | 0.04 | 1.07 | 60 | 0.5 |     | 95 |

TABLE 31

| Ex. No. | Compound No. | λ max (nm) | Initial color ε (0) | Color density ε (120) − ε (0) | Color-developing sensitivity (sec.) | Fading rate τ/1/2 (min.) | Light resistance ΔYI | Remaining ratio (%) |
|---|---|---|---|---|---|---|---|---|
| 130 | 46 | 470 | 0.03 | 0.52 | 60 | 0.6 | 2.2 | 95 |
|  |  | 606 | 0.03 | 1.08 | 60 | 0.6 |  | 95 |
| 131 | 47 | 470 | 0.03 | 0.44 | 60 | 0.6 | 2.2 | 94 |
|  |  | 606 | 0.03 | 0.92 | 60 | 0.6 |  | 94 |
| 132 | 48 | 468 | 0.04 | 0.46 | 60 | 0.6 | 2.2 | 90 |
|  |  | 606 | 0.04 | 0.92 | 60 | 0.6 |  | 90 |
| 133 | 49 | 470 | 0.04 | 0.42 | 60 | 0.5 | 2.3 | 90 |
|  |  | 606 | 0.04 | 0.94 | 60 | 0.5 |  | 90 |
| 134 | 50 | 472 | 0.04 | 0.44 | 60 | 0.5 | 2.2 | 93 |
|  |  | 606 | 0.04 | 0.92 | 60 | 0.5 |  | 93 |
| 135 | 51 | 470 | 0.03 | 0.55 | 70 | 2.0 | 2.2 | 94 |
|  |  | 606 | 0.03 | 1.51 | 70 | 2.0 |  | 94 |
| 136 | 52 | 472 | 0.03 | 0.52 | 65 | 1.8 | 2.0 | 92 |
|  |  | 606 | 0.03 | 1.43 | 65 | 1.8 |  | 92 |
| 137 | 53 | 484 | 0.03 | 0.36 | 60 | 1.1 | 2.2 | 91 |
|  |  | 596 | 0.03 | 0.94 | 60 | 1.1 |  | 91 |
| 138 | 54 | 470 | 0.03 | 0.56 | 60 | 1.5 | 2.4 | 90 |
|  |  | 616 | 0.03 | 0.92 | 60 | 1.5 |  | 90 |
| 139 | 55 | 470 | 0.04 | 0.50 | 60 | 1.8 | 2.6 | 90 |
|  |  | 606 | 0.04 | 1.33 | 60 | 1.8 |  | 90 |
| 140 | 56 | 470 | 0.04 | 0.42 | 65 | 1.5 | 2.3 | 90 |
|  |  | 606 | 0.04 | 0.88 | 65 | 1.5 |  | 90 |
| 141 | 57 | 468 | 0.03 | 0.40 | 60 | 2.5 | 2.2 | 93 |
|  |  | 606 | 0.03 | 0.90 | 60 | 2.5 |  | 93 |
| 142 | 58 | 470 | 0.03 | 0.44 | 60 | 0.4 | 2.0 | 93 |
|  |  | 606 | 0.03 | 1.08 | 60 | 0.4 |  | 93 |
| 143 | 59 | 470 | 0.04 | 0.55 | 60 | 0.8 | 2.0 | 90 |
|  |  | 616 | 0.04 | 1.02 | 60 | 0.8 |  | 90 |
| 144 | 60 | 470 | 0.03 | 0.62 | 60 | 0.8 | 2.0 | 94 |
|  |  | 616 | 0.03 | 1.02 | 60 | 0.8 |  | 95 |

TABLE 32

| Ex. No. | Compound No. | λ max (nm) | Initial color ε (0) | Color density ε (120) − ε (0) | Color-developing sensitivity (sec.) | Fading rate τ/1/2 (min.) | Light resistance ΔYI | Remaining ratio (%) |
|---|---|---|---|---|---|---|---|---|
| 145 | 61 | 470 | 0.03 | 0.44 | 60 | 0.4 | 2 | 94 |
|  |  | 606 | 0.03 | 1.03 | 60 | 0.4 |  | 94 |
| 146 | 62 | 470 | 0.03 | 0.40 | 60 | 0.4 | 2.2 | 90 |
|  |  | 606 | 0.03 | 0.92 | 60 | 0.4 |  | 90 |
| 147 | 63 | 468 | 0.03 | 0.46 | 60 | 0.4 | 2.2 | 92 |
|  |  | 606 | 0.03 | 1.00 | 60 | 0.4 |  | 92 |
| 148 | 64 | 470 | 0.04 | 0.43 | 60 | 0.4 | 2.3 | 90 |
|  |  | 606 | 0.04 | 0.98 | 60 | 0.4 |  | 90 |
| 149 | 65 | 470 | 0.03 | 0.42 | 60 | 0.4 | 2.2 | 94 |
|  |  | 606 | 0.03 | 0.99 | 60 | 0.4 |  | 94 |
| 150 | 66 | 466 | 0.03 | 0.80 | 60 | 2.5 | 2.0 | 92 |
|  |  | 570 | 0.03 | 1.20 | 60 | 2.5 |  | 92 |
| 151 | 67 | 488 | 0.03 | 0.95 | 60 | 2.5 | 3.0 | 88 |
|  |  | 594 | 0.03 | 1.33 | 60 | 2.5 |  | 88 |
| 152 | 68 | 472 | 0.03 | 0.44 | 60 | 0.9 | 2.2 | 96 |
|  |  | 606 | 0.03 | 1.03 | 60 | 0.9 |  | 96 |
| 153 | 69 | 468 | 0.03 | 0.43 | 60 | 1.0 | 2.0 | 94 |
|  |  | 606 | 0.03 | 1.00 | 60 | 1.0 |  | 94 |
| 154 | 70 | 470 | 0.04 | 0.44 | 60 | 0.9 | 2.4 | 96 |
|  |  | 604 | 0.04 | 0.98 | 60 | 0.9 |  | 96 |
| 155 | 71 | 470 | 0.04 | 0.44 | 60 | 0.9 | 2.4 | 95 |
|  |  | 604 | 0.04 | 0.96 | 60 | 0.9 |  | 95 |
| 156 | 72 | 468 | 0.03 | 0.43 | 60 | 1.6 | 2.0 | 90 |
|  |  | 602 | 0.03 | 0.97 | 60 | 1.6 |  | 90 |
| 157 | 73 | 470 | 0.03 | 0.41 | 60 | 1.8 | 2.4 | 93 |
|  |  | 600 | 0.03 | 0.94 | 60 | 1.8 |  | 93 |
| 158 | 74 | 468 | 0.04 | 0.43 | 60 | 1.7 | 2.3 | 90 |
|  |  | 600 | 0.04 | 0.88 | 60 | 1.7 |  | 90 |
| 159 | 75 | 460 | 0.04 | 0.44 | 60 | 1.6 | 2.3 | 90 |
|  |  | 602 | 0.04 | 0.88 | 60 | 1.6 |  | 90 |

TABLE 33

| Ex. No. | Compound No. | Initial λ max (nm) | Color color ε (0) | Color density ε (120) − ε (0) | Color-developing sensitivity (sec.) | Fading rate τ/1/2 (min.) | Light resistance ΔYI | Remaining ratio (%) |
|---|---|---|---|---|---|---|---|---|
| 160 | 76 | 466 | 0.03 | 0.52 | 60 | 0.9 | 2.8 | 90 |
|  |  | 606 | 0.03 | 1.06 | 60 | 0.9 |  | 90 |
| 161 | 77 | 470 | 0.03 | 0.48 | 60 | 1.0 | 2.8 | 90 |
|  |  | 606 | 0.03 | 0.98 | 60 | 1.0 |  | 90 |
| 162 | 78 | 468 | 0.04 | 0.46 | 60 | 2.0 | 2.3 | 90 |
|  |  | 604 | 0.04 | 0.88 | 60 | 2.0 |  | 90 |
| 163 | 79 | 470 | 0.03 | 0.38 | 60 | 0.9 | 2.6 | 93 |
|  |  | 606 | 0.03 | 0.88 | 60 | 0.9 |  | 93 |
| 164 | 80 | 472 | 0.03 | 0.40 | 60 | 0.9 | 2.5 | 93 |
|  |  | 606 | 0.03 | 0.88 | 60 | 0.9 |  | 93 |
| 165 | 81 | 464 | 0.03 | 0.65 | 60 | 0.6 | 2.5 | 90 |
|  |  | 618 | 0.03 | 0.98 | 60 | 0.6 |  | 90 |
| 166 | 82 | 474 | 0.03 | 0.43 | 60 | 0.6 | 2.9 | 90 |
|  |  | 614 | 0.03 | 0.86 | 60 | 0.6 |  | 90 |
| 167 | 83 | 476 | 0.03 | 0.32 | 60 | 0.6 | 2.9 | 90 |
|  |  | 628 | 0.03 | 0.80 | 60 | 0.6 |  | 90 |
| 168 | 84 | 468 | 0.03 | 0.40 | 60 | 0.5 | 2.2 | 94 |
|  |  | 572 | 0.03 | 0.88 | 60 | 0.5 |  | 94 |
| 169 | 1 | 460 | 0.05 | 0.47 | 65 | 1.0 | 1.5 | 95 |
|  |  | 562 | 0.05 | 0.92 | 65 | 1.0 |  | 95 |

Example 169

Three parts by weight of the chromene compound obtained in Example 1 was added to 10 parts by weight of a tetraethylene glycol dimethacrylate, 50 parts by weight of a 2,2-bis[4-(methacryloxyethoxy)phenyl]propane, 10 parts by weight of a methyl ether nonaethylene glycol methacrylate, 20 parts by weight of a trimethylolpropane trimethacrylate and 10 parts by weight of a glycidyl methacrylate, and was mixed to a sufficient degree. To the mixture were added 3 parts by weight of a bis(1,2,2,6,6-pentamethyl-4-piperidyl) sebacate as an ultraviolet-ray stabilizer, 0.02 parts by weight of a 2,4,6-trimethylbenzoyldiphenylphosphine oxide as a photopolymerization initiator, and 0.5 parts by weight of a t-butylperoxy-2-ethyl hexanate as a thermal polymerization initiator, followed by stirring to a sufficient degree and deaeration under reduced pressure. The mixture solution was poured into a mold constituted by using a glass plate, an ADC resin plate (2.0 mm thick) and a gasket of an ethylene-vinyl acetate copolymer, irradiated on both surfaces thereof with active energy rays using a 1.5-kw metal halide lamp (with a heat ray-cutting filter) from a distance of 25 cm for one minutes to conduct the polymerization. Thereafter, the mixture solution was cured in a polymerizing furnace at 110° C. for one hour, and was parted from the glass mold to obtain an ADC resin having a photochromic polymer of a thickness of 0.1 mm laminated on one surface thereof. The photochromic properties of the optical material were evaluated by the same method as that of Example 85. The results were as shown in Table 33.

Despite of this thickness which was as small as 0.1 mm, the photochromic polymer of Example 169 exhibited a high color-developing density and a large light resistance like the photochromic polymer having a thickness of 2 mm obtained in Example 85.

Comparative Examples 1 to 4

For the purpose of comparison, the photochromic polymers were similarly obtained by using the compounds represented by the following formulas (A), (B), (C) and (D),

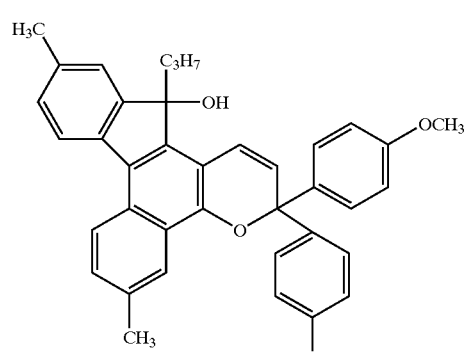

(A)

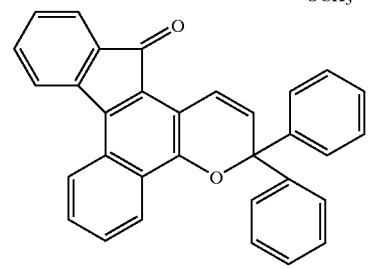

(B)

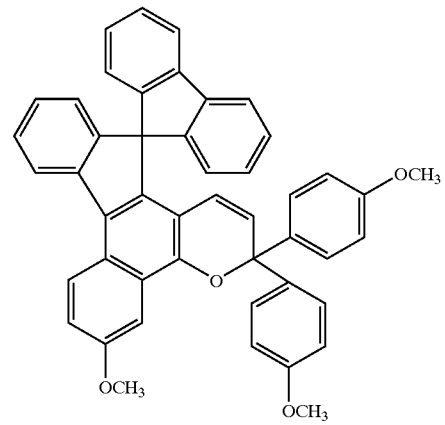

(C)

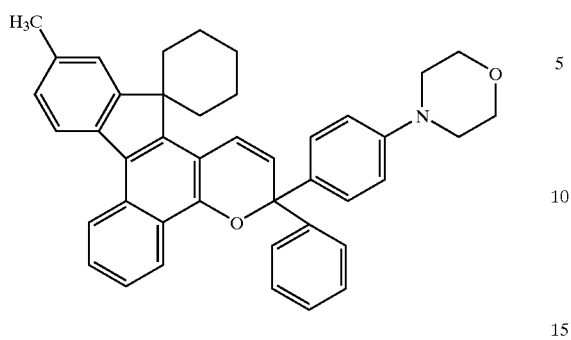

(D)

to evaluate their properties. The results were as shown in Table 34.

TABLE 34

| Comp. Ex. No. | Compound No. | Initial λ max (nm) | Color color ε (0) | Color-developing density ε (120) − ε (0) | Fading rate sensitivity (sec.) | Light resistance τ/1/2 (min.) | ΔYI | Remaining ratio (%) |
|---|---|---|---|---|---|---|---|---|
| 1 | (A) | 440 | 0.03 | 0.40 | 125 | 10.0 | 8 | 73 |
|   |     | 570 | 0.03 | 0.5  | 125 | 10.0 |   | 73 |
| 2 | (B) | 425 | 0.05 | 0.20 | 150 | 15.0 | 15 | 70 |
|   |     | 536 | 0.03 | 0.3  | 150 | 15.0 |   | 70 |
| 3 | (C) | 460 | 0.03 | 0.70 | 140 | 5.0  | 3 | 90 |
|   |     | 575 | 0.03 | 1.1  | 140 | 5.0  |   | 90 |
| 4 | (D) | 460 | 0.03 | 0.50 | 90  | 13.0 | 1.2 | 93 |
|   |     | 566 | 0.03 | 1.18 | 90  | 13.0 |   | 92 |

The photochromic polymers of Examples 85 to 169 using the chromene compounds of the present invention are all superior to the photochromic polymers of Comparative Examples 1 and 2 with respect to the color-developing sensitivity, fading rate and light resistance in the photochromic properties. Besides, the photochromic polymers of the present invention exhibit fading rates larger than that of Comparative Example 3.

Industrial Applicability

The chromene compounds of the present invention exhibit excellent light resistance in addition to exhibiting excellent photochromic properties such as small initial color, high color-developing sensitivity and high color density when dispersed in a high-molecular matrix and, particularly, in a high-molecular matrix having a high hardness, as well as large fading rates when dispersed in a solution or in a high-molecular solid matrix.

By using the chromene compounds of the present invention, therefore, it is allowed to obtain photochromic lenses which develop color quickly and densely when they are brought to the outdoors, which quickly fade to return to the initial color tone when brought back to the indoors from the outdoors, which exhibit a large light resistance even after used for extended periods of time, and which exhibit excellent strength.

What is claimed is:

1. A chromene compound represented by the following general formula (1),

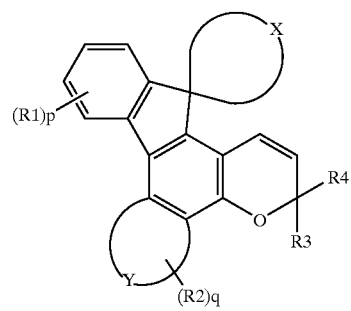

(1)

wherein a group represented by the following formula (2),

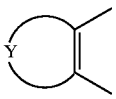

(2)

is an aromatic hydrocarbon group or an unsaturated heterocyclic group;

$R^1$ is a hydroxyl group, an alkyl group, a trifluoromethyl group, an alkoxy, an alkoxycarbonyl group, a carboxyl group, an alkoxymethyl group, a hydroxymethyl group, an aralkoxy group, an amino group, a substituted amino group, a cyano group, a nitro group, a halogen atom, an aralkyl group, a substituted or unsubstituted aryl group, a substituted or unsubstituted heteroaryl group, a substituted or unsubstituted heterocyclic group having a nitrogen atom as a hetero atom and in which the nitrogen atom and an indene ring are coupled together, or a condensed heterocyclic group in which the heterocyclic group is condensed with an aromatic hydrocarbon ring or an aromatic heterocyclic ring, and p is an interger of 0 to 3;

$R_2$ is a hydroxyl group, an alkyl group, a trifluoromethyl group, an alkoxy group, an alkoxycarbonyl group, a carboxyl group, an alkoxymethyl group, a hydroxymethyl group, an aralkoxy group, an amino group, a substituted amino group, a cyano group, a nitro group, a halogen atom, an aralkyl group, a substituted or unsubstituted aryl group, a substituted or unsubstituted heteroaryl group, a substituted or unsubstituted heterocyclic group having a nitrogen aton as a hetero atom and in which the nitrogen atom and a ring of the group represented by the above formula (2) are bonded together, or a condensed heterocyclic group in which the heterocyclic group is condensed with an aromatic hydrocarbon ring or an aromatic heterocyclic ring, and q is an integer of 0 to 3;

$R^3$ and $R^4$ are, independently from each other, groups represented by the following formula (3),

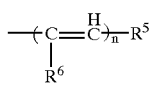
(3)

wherein $R^5$ is a substituted or unsubstituted aryl group, or a substituted or unsubstituted heteroaryl group, $R^6$ is a hydrogen atom, an alkyl group or a halogen atom, and n is an integer of 1 to 3, a group represented by the following formula (4),

(4)

wherein $R^7$ is substituted or unsubstituted aryl group, or a substituted or unsubstituted heteroaryl group, and m is an integer of 1 to 3, a substituted or unsubstituted aryl group, a substituted or unsubstituted heteroaryl group, or an alkyl group, or $R^3$ and $R^4$ together may constitute an aliphatic hydrocarbon ring or an aromatic hydrocarbon ring; and a cyclic group represented by the following formula (5) which is spiro-bonded to the indene skeleton of the general formula (1) at the 1-position,

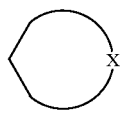
(5)

is (a) an alicyclic hydrocarbon group consisting of an unsubstituted monocyclic ring formed by 7 to 20 carbon atoms, (b) an alicyclic hydrocarbon group consisting of a monocyclic ring of 4 to 20 skeleton carbon atoms having at least one substituent selected from alkyl group, alkoxy group, amino group, substituted amino group, substituted or unsubstituted aralkyl group and substituted or unsubstituted aryl group, (c) a bridge structured or a spiran structured polycyclic hydrocarbon group consistion of a cyclic ring of 4 to 20 skeleton carbon atoms, which may have at least one substituent selected from the group consistion of alkyl group, alkoxy group, amino group, substituted amino group, substituted or unsubstituted aralky group and substituted or unsubstituted aryl group, and (d) a substituted or unsubstituted cyclic group having a ring which has 4 to 20 carbon atoms therein and has any one of the following groups in a number of 1 to 2 or more but does not have two oxy groups therein,

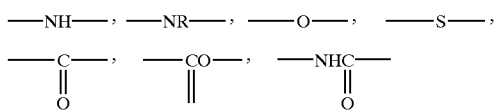

wherein R is an alkyl group, a substituted or unsubstituted aryl group, a substituted or unsubstituted aralkyl group, a carboxyl group or an alkoxycarbonyl group with the proviso that said cyclic group of (d) have no aromatic or hetero aromatic ring which is annelated thereto.

2. A chromene compound according to claim 1, wherein said cyclic group represented by the formula (5) in the general formula (1) is (a') an alicyclic hydrocarbon group consisting of an unsubstituted monocyclic ring formed by 7 to 15 carbon atoms or (b') an alicyclic hydrocarbon group consisting of a substituted monocyclic ring of 4 to 15 skeleton carbon atoms having at least one substituent selected from the group consisting of alkyl group, alkoxy group, amino group, substituted amino group, substituted or substituted aralkyl group and substituted or unsubstituted aryl group.

3. A chromene compound according to claim 1, wherein said cyclic group represented by the formula (5) in the general formula (1) is (b") an alicyclic hydrocarbon group consisting of a substituted monocyclic ring of 4 to 15 skeleton carbon atoms having at least one substituent selected from the group consisting of alkyl group, alkoxy group, amino group, substituted amino group, substituted or unsubstituted aralkyl group and substituted or unsubstituted aryl group at the β-position of the spiro carbon.

4. A chromene compound according to claim 1, wherein said cyclic group represented by the formula (5) in the general formula (1) is (c') a bicyclic of tricyclic group formed by 4to 15 skeleton carbon atoms having at least one substituent selected form the group consisting of alkyl group, alkoxy group, amino group, substituted amino group, substituted or unsubstituted aralkyl group and substituted or unsubstituted aryl group.

5. A chromene compound according to claim 1, wherein said cyclic group represented by the formula (5) in the general formula (1) is (d') a substituted or unsubstituted cyclic group having a ring which has 4 to 15 carbon atoms therein and has one or two of at least one kind of group selected from the group consisting of —NH— group, —NR— group (where R is an alkyl group, a substituted or unsubstituted aryl group, substituted or unsubstituted aralkyl group, a carboxyl group or an alkoxycarbonyl group), —S— group, —O— group, —C(=O)— group, —C(=O)O— group and —NHC(=O)— group, but does not have two oxy groups therein.

6. A chromene compound according to claim 5, wherein said alicyclic group (d') is (d") a substituted or unsubstituted monocyclic group, or a saturated or unsaturated bridge structured polycyclic group.

7. A photochromic material for an optical article use comprising a high-molecular matrix and the chromene compound of claim 1 dispersed therein.

8. A photochromic material according to claim 7, wherein the high-molecular matrix has a Rockwell hardness of 80 to 120.

9. A photochromic laminated lens comprising a lens, a polymer film covering at least one surface of the lens and the chromene compound of claim 1 dispersing the film.

10. A photochromic composition comprising the chromene compound of claim 1.

11. A photochromic composition according to claim 10, further comprising a polymerizable monomer.

12. A photochromic composition according to claim 10, further comprising an ultraviolet-ray stabilizer.

* * * * *